United States Patent
Zhu et al.

(10) Patent No.: US 12,138,316 B2
(45) Date of Patent: Nov. 12, 2024

(54) ANTI-B7H3 ANTIBODY-DRUG CONJUGATE AND USE THEREOF

(71) Applicant: Duality Biologics (Suzhou) Co., Ltd., Shanghai (CN)

(72) Inventors: Zhongyuan Zhu, Shanghai (CN); Chen Zhong, Shanghai (CN); Yu Zhang, Shanghai (CN); Chenggang Li, Shanghai (CN)

(73) Assignee: Duality Biologics (Suzhou) Co., Ltd., Shanghai (CN)

( * ) Notice: Subject to any disclaimer, the term of this patent is extended or adjusted under 35 U.S.C. 154(b) by 0 days.

(21) Appl. No.: 18/511,591

(22) Filed: Nov. 16, 2023

(65) Prior Publication Data
US 2024/0148892 A1 May 9, 2024

Related U.S. Application Data

(63) Continuation of application No. PCT/CN2023/098596, filed on Jun. 6, 2023.

(51) Int. Cl.
*A61K 47/68* (2017.01)
*A61P 35/00* (2006.01)

(52) U.S. Cl.
CPC ...... *A61K 47/6849* (2017.08); *A61K 47/6803* (2017.08); *A61K 47/6889* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,225,539 A | 7/1993 | Winter |
| 5,530,101 A | 6/1996 | Queen et al. |
| 5,585,089 A | 12/1996 | Queen et al. |
| 5,693,762 A | 12/1997 | Queen et al. |
| 6,180,370 B1 | 1/2001 | Queen et al. |
| 7,112,421 B2 | 9/2006 | Ambrose et al. |
| 2012/0294796 A1 | 11/2012 | Johnson et al. |

FOREIGN PATENT DOCUMENTS

| | | |
|---|---|---|
| CN | 109641962 A | 4/2019 |
| WO | 2018161872 A1 | 9/2018 |
| WO | 2019024911 A1 | 2/2019 |
| WO | 2020063673 A1 | 4/2020 |
| WO | 2020063676 A1 | 4/2020 |
| WO | 2021190586 A1 | 9/2021 |
| WO | 2022068878 A1 | 4/2022 |

OTHER PUBLICATIONS

Shin et al., Cancer Cell Int. 2023; 23: 172 (Year: 2023).*

(Continued)

*Primary Examiner* — Karl J Puttlitz
(74) *Attorney, Agent, or Firm* — Honigman LLP

(57) ABSTRACT

The present invention provides an antibody-drug conjugate specifically binding to B7H3 and a pharmaceutical composition comprising the same. A method for using the antibody-drug conjugate of the present invention and use thereof are also provided herein.

25 Claims, 13 Drawing Sheets
Specification includes a Sequence Listing.

Gel info: NuPAGE, Novex 4-12% Bis-Tris Gel

(56) References Cited

OTHER PUBLICATIONS

Al-Lazikani, Bissan et al. "Standard conformations for the canonical structures of immunoglobulins." Journal of molecular biology 273 4 (1997): 927-48.

Almagro, Juan Carlos. "Identification of differences in the specificity—determining residues of antibodies that recognize antigens of different size: implications for the rational design of antibody repertoires." Journal of Molecular Recognition 17 (2004): n. pag.

Ausubel F et al.(editor) Current Protocols in Molecular Biology, John Wiley & Sons, New York, 2000.

Better, Marc D et al. "*Escherichia coli* secretion of an active chimeric antibody fragment." Science 240 4855 (1988): 1041-3.

Chothia, Cyrus et al. "Conformations of immunoglobulin hypervariable regions." Nature 342 (1989): 877-883.

Chothia, Cyrus et al. "Canonical structures for the hypervariable regions of immunoglobulins." Journal of molecular biology 196 4 (1987): 901-17.

Dunbar, James and Charlotte M. Deane. "ANARCI: antigen receptor numbering and receptor classification." Bioinformatics 32 (2015): 298-300.

Edelman, Gerald M et al. "The covalent structure of an entire gammaG immunoglobulin molecule." Proceedings of the National Academy of Sciences of the United States of America 63 1 (1969): 78-85.

Genebank accession No. NP_001019907 (human).

Genebank accession No. NP_001316557 (human).

Genebank accession No. NP_001316558 (human).

Genebank accession No. NP_079516 (human).

Genebank accession No. NP_598744 (mouse).

Lefranc, Marie-Paule et al. "IMGT, the international ImMunoGeneTics database." Nucleic acids research 27 1 (1999): 209-12.

Jones, Peter T et al. "Replacing the complementarity-determining regions in a human antibody with those from a mouse." Nature 321 (1986): 522-525.

Kabat, Elvin A.. "Sequences of proteins of immunological interest." (1991).

Lefranc, Marie-Paule et al. "IMGT unique numbering for immunoglobulin and T cell receptor variable domains and Ig superfamily V-like domains." Developmental and comparative immunology 27 1 (2003): 55-77.

Lefranc, Marie-Paule. "Unique database numbering system for immunogenetic analysis." Immunology today 18 11 (1997): 509.

Giudicelli, Veronique et al. "IMGT, the International ImMunoGeneTics Database: a New Design for Immunogenetics Data Access." Studies in health technology and informatics 52 Pt 1 (1998): 351-5.

Liu, Alvin Y et al. "Chimeric mouse-human lgG1 antibody that can mediate lysis of cancer cells." Proceedings of the National Academy of Sciences of the United States of America 84 10 (1987): 3439-43.

Martin A, "Antibody bioinformatics website of Dr. Andrew Martin's lab at UCL", last updated on Jul. 31, 2018.

Remington, Joseph Price and Alfonso R. Gennaro. "Remington's pharmaceutical sciences." (2016).

Uniprot ID: Q5ZPR3 (human 4lgB7H3).

Giudicelli V et al., "IMGT, the international ImMunoGeneTics database", Nucleic Acids Research, 1997, vol. 25, No. 1, pp. 206-211.

Verhoeyen M et al., Reshaping human antibodies: grafting an antilysozyme activity, Science, 1988, vol. 239 (4847): 1534-1536.

\* cited by examiner

VH regions of W301088-1.145.16-xIgG1KV320 ("1") and
W301088-1.145.16-z3-p1-uIgG1KV320 ("2")

```
1    1 DVQLQESGPGLVKPSQSLSLTCTVT DYSITGDYAWN WIRQFPGNKLEWMG    50
       .|||||||||||||||||:|||||||||||||||||||.||..|||:|
2    1 QVQLQESGPGLVKPSQTLSLTCTVT DYSITGDYAWN WIRQHPGKGLEWIG    50

1   51 YISYSGSTSYNPSLQS RISITRDTSKNQFFLQLNSVTSEDTATYFCAR SL    100
       ||||||||||||||||::|:|||||||.|:|:|||:.|||.||||||
2   51 YISYSGSTSYNPSLQS RVTISRDTSKNQFSLKLSSVTAADTAVYFCAR SL    100

1  101 GRRWYFVV WGAGTTVTVSA    119
       ||||||||.|||||||:
2  101 GRRWYFVV WGQGTTVTVSS    119
```

VL regions of W301088-1.145.16-xIgG1KV320 ("1") and
W301088-1.145.16-z3-p1-uIgG1KV320 ("2")

ANTI-B7H3 ANTIBODY-DRUG CONJUGATE AND USE THEREOF

CROSS-REFERENCE TO RELATED APPLICATIONS

This application is a Continuation of Patent Cooperation Treaty application PCT/CN2023/098596, filed Jun. 6, 2023, which claims the benefit of Chinese Patent Application No. 202310391084.5, filed Apr. 12, 2023, and Chinese Patent Application No. 202210638941.2, filed Jun. 7, 2022. Priority is claimed to all of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "P1562_PF 230274PCT_seql.xml." is 18,689 bytes in size and was created on Jun. 6, 2023, and filed electronically herewith.

TECHNICAL FIELD

The present invention provides an antibody-drug conjugate specifically binding to B7H3 and a composition comprising the same. A method for using the antibody-drug conjugate of the present invention and use thereof are also provided.

BACKGROUND

B7H3, also known as CD276, B7RP-2 and B7-H3, is a member of the B7 family and has 20% to 27% amino acid sequence homology with the other members of the B7 family. Although the B7H3 transcript is widely expressed, its expression is limited and maintained at low levels on normal tissues and immune cells, and it is overexpressed in a variety of human malignancies, including melanoma, breast cancer, prostate cancer, etc. It has been reported that B7-H3 is expressed in the cell membrane and the cytoplasm, or within the nuclei of cancer cells, and also on the tumor-associated vascular system. B7H3 is not constitutively expressed on T cells and NK cells, but is constitutively under-expressed on some APCs such as DCs, and GM-CSF, IFNγ, etc. can induce its expression on APCs. B7-H3 is a very promising anti-cancer target. Although the exact functions of B7-H3 are unclear, its diverse immune functions have been demonstrated, including stimulation, inhibition of T cell proliferation, and inhibition of NK cell functions. It is considered that there are different receptors on immune cells, and these receptors may competitively bind to B7H3 on tumors. In addition to its immune checkpoint function, it has been reported that the high levels of B7H3 expression are associated with poor cancer prognosis and enhance cell proliferation, migration, invasion, angiogenesis, metastatic ability and anti-cancer drug resistance.

Similar to the other molecules of the B7 family, B7H3 is a type I transmembrane glycoprotein whose extracellular domain comprises an IgV-IgC domain. Unlike the mouse B7H3 gene, which has only one IgV-IgC domain, human B7H3 has two subtypes, one of which contains one copy of the IgV-IgC domain (designated 2IgB7H3) and the other of which contains two IgV-IgC domains (designated 4IgB7H3), as a result of gene duplication and differential splicing. 4IgB7H3, instead of 2IgB7H3, is the major subtype expressed on immune and malignant cells, which suggests that 4IgB7H3 may play a unique important role in tumor development and tumor immunology.

As B7H3 is overexpressed on many tumor cells, therapeutic molecules against B7H3 are currently being developed to treat relevant indications. However, there is still room for improvement and a clinical need for the development of novel anti-B7H3 antibodies, or antibody-drug conjugates.

SUMMARY

The present application provides an anti-B7H3 antibody-drug conjugate or a pharmaceutically acceptable salt thereof, which may have one or more effects selected from the group consisting of: (1) having inhibitory activity against in vitro proliferation of tumor cells; (2) having better affinity for human B7H3; (3) having plasma stability; (4) having an in vivo anti-tumor effect; (5) having a bystander effect; (6) having the capacity to inhibit transport by transporters; (7) having the capacity to target tumors in vivo; and (8) having good in vivo safety.

In one aspect, the present application provides an antibody-drug conjugate, which comprises: a B7H3-targeting antibody or an antigen-binding fragment thereof, a linker unit and a cytotoxic drug, wherein the B7H3-targeting antibody or the antigen-binding fragment thereof comprises: HCDR1 comprising an amino acid sequence as set forth in SEQ ID NO: 1, HCDR2 comprising an amino acid sequence as set forth in SEQ ID NO: 2, HCDR3 comprising an amino acid sequence as set forth in SEQ ID NO: 3, LCDR1 comprising an amino acid sequence as set forth in SEQ ID NO: 4 or 7, LCDR2 comprising an amino acid sequence as set forth in SEQ ID NO: 5, and LCDR3 comprising an amino acid sequence as set forth in SEQ ID NO: 6.

In some embodiments, in the antibody-drug conjugate provided herein, the antibody or the antigen-binding fragment thereof comprises:
 (I) a heavy chain variable region comprising an amino acid sequence as set forth in SEQ ID NO: 8 and a light chain variable region comprising an amino acid sequence as set forth in SEQ ID NO: 9; or a heavy chain variable region comprising an amino acid sequence as set forth in SEQ ID NO: 10 and a light chain variable region comprising an amino acid sequence as set forth in SEQ ID NO: 11; or
 (II) a heavy chain variable region having at least 95%, 96%, 97%, 98%, or 99% identity to SEQ ID NO: 8 and a light chain variable region having at least 95%, 96%, 97%, 98%, or 99% identity to SEQ ID NO: 9; or a heavy chain variable region having at least 95%, 96%, 97%, 98%, or 99% identity to SEQ ID NO: 10 and a light chain variable region having at least 95%, 96%, 97%, 98%, or 99% identity to SEQ ID NO: 11; or
 (III) a heavy chain variable region having one or more (e.g., 1, 2, 3, 4, 5, 6, 7, 8, 9, or 10) amino acid additions, deletions and/or substitutions in a framework region thereof as compared to SEQ ID NO: 8 or 10, and a light chain variable region having one or more (e.g., 1, 2, 3, 4, 5, 6, 7, 8, 9, or 10) amino acid additions, deletions and/or substitutions in a framework region thereof as compared to SEQ ID NO: 9 or 11.

In some embodiments, in the antibody-drug conjugate provided herein, the antibody is selected from the group consisting of: a human antibody, a humanized antibody, a chimeric antibody, a multispecific antibody, a monoclonal antibody, and a polyclonal antibody.

In some embodiments, in the antibody-drug conjugate provided herein, the antibody or the antigen-binding fragment thereof is a humanized antibody or an antigen-binding fragment thereof.

In some embodiments, in the antibody-drug conjugate described herein, the antibody is a monoclonal antibody.

In some embodiments, in the antibody-drug conjugate provided herein, the antibody is a full-length antibody or an antigen-binding fragment thereof, the antigen-binding fragment being, for example, selected from the group consisting of: an Fab, an Fab', an F(ab')$_2$, an Fv, an ScFv, an Fab'-SH, an sdAb, a VHH, a bispecific antibody, and a linear antibody.

In some embodiments, in the antibody-drug conjugate provided herein, the antibody comprises an immunoglobulin constant region, the immunoglobulin constant region being a human IgG constant region, e.g., a human IgG1 constant region.

In some embodiments, in the antibody-drug conjugate provided herein, the antibody is an antibody in IgG1 form, an antibody in IgG2 form, an antibody in IgG3 form, or an antibody in IgG4 form.

In some embodiments, in the antibody-drug conjugate provided herein, the antibody or the antigen-binding fragment thereof comprises:

(I) a heavy chain comprising an amino acid sequence as set forth in SEQ ID NO: 12 and a light chain comprising an amino acid sequence as set forth in SEQ ID NO: 13; or a heavy chain comprising an amino acid sequence as set forth in SEQ ID NO: 14 and a light chain comprising an amino acid sequence as set forth in SEQ ID NO: 15; or (II) a heavy chain having at least 95%, 96%, 97%, 98%, or 99% identity to SEQ ID NO: 12 and a light chain having at least 95%, 96%, 97%, 98%, or 99% identity to SEQ ID NO: 13; or a heavy chain having at least 95%, 96%, 97%, 98%, or 99% identity to SEQ ID NO: 14 and a light chain having at least 95%, 96%, 97%, 98%, or 99% identity to SEQ ID NO: 15.

In some embodiments, the antibody of the present invention is the anti-B7H3 antibody WBP301088.

In certain preferred embodiments of the present invention, in the antibody-drug conjugate described herein, certain groups in the compounds of formulas (A-1), (A-2), (A-1a) and (A-1b) or pharmaceutically acceptable salts thereof are defined as follows, and groups not mentioned are as described in any one of the solutions of the present application ("in some embodiments" for short).

In some embodiments, in the antibody-drug conjugate provided herein, the cytotoxic drug comprises or is selected from the group consisting of the following structures: a structure shown as formula (A-1), and a tautomer, an enantiomer, a diastereoisomer and a mixture of isomers thereof, and a pharmaceutically acceptable salt and a solvate thereof,

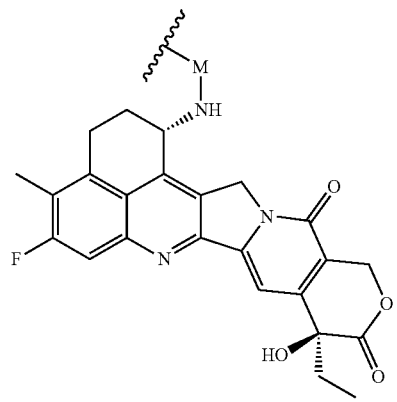

(A-1)

wherein,
M is —L$^2$—L$^1$—C(O)—;
L$^2$ is —O— or —S—;
L$^1$ is —(C(R$^{1a}$)(R$^{1b}$))$_m$—CH$_2$—, C$_3$-C$_6$ saturated cycloalkyl, or 3- to 6-membered saturated heterocyclyl, wherein the C$_3$-C$_6$ saturated cycloalkyl and the 3- to 6-membered saturated heterocyclyl are each independently optionally substituted with one or more R$^{2a}$;
m is selected from the group consisting of 1, 2, 3, and 4;
the 3- to 6-membered saturated heterocyclyl comprises 1-3 heteroatoms selected from the group consisting of N, O, and S;
each R$^{1a}$ is independently selected from the group consisting of hydrogen, halogen, hydroxy, amino, and C$_1$-C$_6$ alkyl, wherein the C$_1$-C$_6$ alkyl is optionally substituted with one or more R;
R$^{1b}$ and R$^{2a}$ are each independently selected from the group consisting of hydrogen, halogen, hydroxy, amino, and C$_1$-C$_6$ alkyl, wherein the C$_1$-C$_6$ alkyl is optionally substituted with one or more R;
each R is independently hydrogen or halogen.

In some embodiments, in the antibody-drug conjugate provided herein, the L$^1$ is —(C(R$^{1a}$)(R$^{1b}$))$_m$—CH$_2$—, wherein R$^{1a}$ is selected from the group consisting of: hydrogen, halogen, and C$_1$-C$_6$ alkyl; R$^{1b}$ is selected from the group consisting of: hydrogen, halogen, and C$_1$-C$_6$ alkyl. In some embodiments, in the antibody-drug conjugate provided herein, the L$^1$ is —(C(R$^{1a}$)(R$^{1b}$))$_m$—CH$_2$—, wherein R$^{1a}$ is hydrogen or —CH$_3$; R$^{1b}$ is selected from the group consisting of: hydrogen and —CH$_3$; for example, R$^{1a}$ is —CH$_3$; R$^{1b}$ is selected from the group consisting of: hydrogen and —CH$_3$.

In some embodiments, in the antibody-drug conjugate provided herein, L$^1$ is —(C(R$^{1a}$)(R$^{1b}$))$_m$—CH$_2$—, wherein m is 1 or 2.

In some embodiments, in the antibody-drug conjugate provided herein, L$^1$ is selected from the group consisting of:

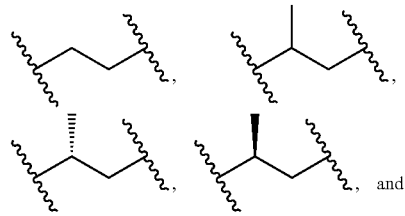

and

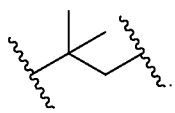

In some embodiments, in the antibody-drug conjugate provided herein, $L^1$ is $C_3$-$C_6$ saturated cycloalkyl or 3- to 6-membered saturated heterocyclyl, wherein the $C_3$-$C_6$ saturated cycloalkyl and the 3- to 6-membered saturated heterocyclyl are each independently optionally substituted with one or more $R^{2a}$, wherein each $R^{2a}$ is independently selected from the group consisting of: hydrogen, halogen, and $C_1$-$C_6$ alkyl.

In some embodiments, in the antibody-drug conjugate provided herein, $L^1$ is $C_3$-$C_6$ saturated cycloalkyl optionally substituted with one or more $R^{2a}$, wherein each $R^{2a}$ is independently selected from the group consisting of: hydrogen, halogen, and $C_1$-$C_6$ alkyl. In some embodiments, in the antibody-drug conjugate provided herein, $L^1$ is $C_3$-$C_6$ saturated cycloalkyl.

In some embodiments, in the antibody-drug conjugate provided herein, $L^1$ is:

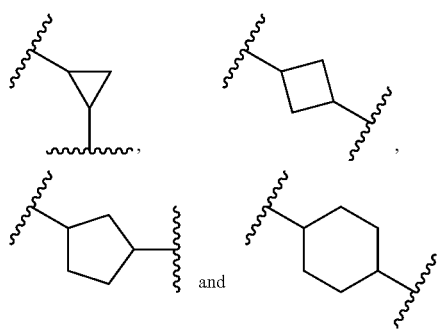

optionally substituted with 1, 2, or 3 $R^{2a}$, wherein each $R^{2a}$ is independently selected from the group consisting of: hydrogen, halogen, and $C_1$-$C_6$ alkyl.

In some embodiments, in the antibody-drug conjugate provided herein, $L^1$ is selected from the group consisting of:

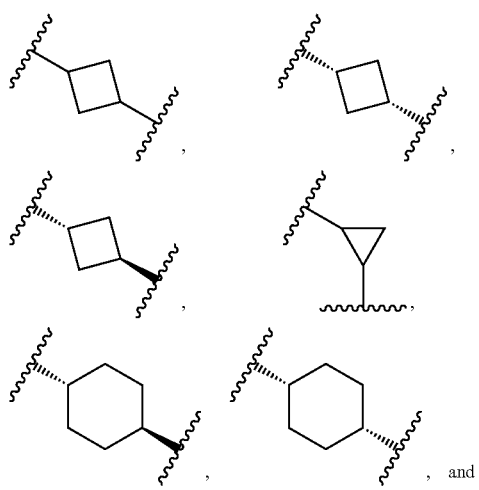

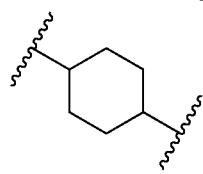

In some embodiments, in the antibody-drug conjugate provided herein, the -M- is selected from the group consisting of:

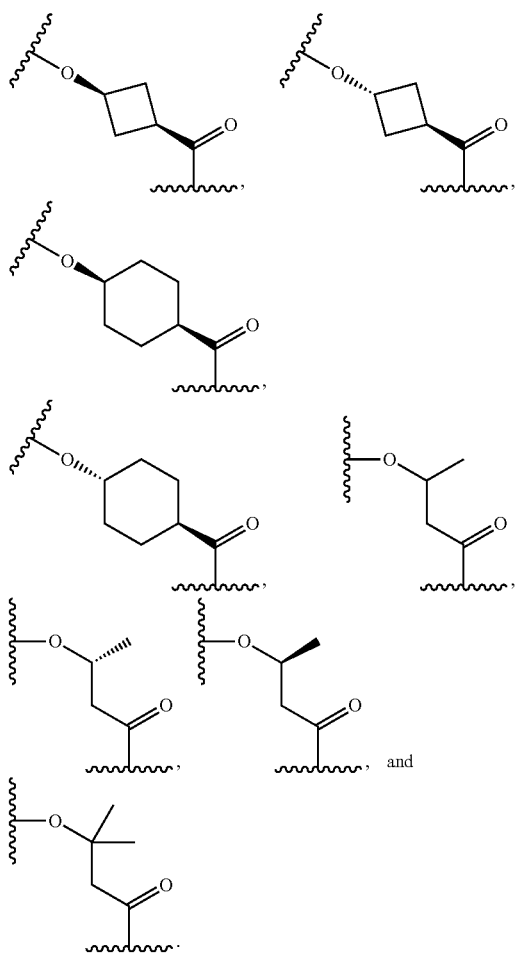

In some embodiments, in the anti-B7H3 antibody-drug conjugate provided herein, isomers thereof, a pharmaceutically acceptable salt thereof, or a mixture thereof, the —M— is:

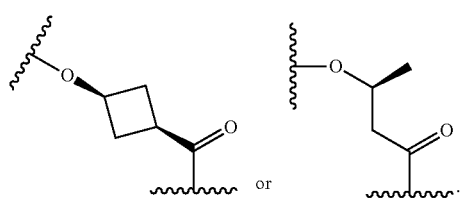

In some embodiments, in the anti-B7H3 antibody-drug conjugate provided herein, the cytotoxic drug
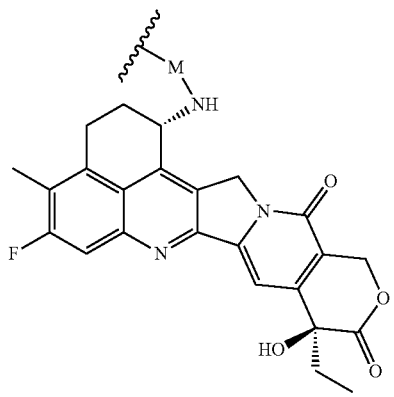
is of any one of the following structures:
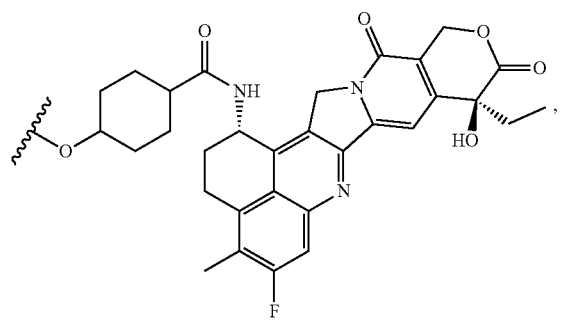
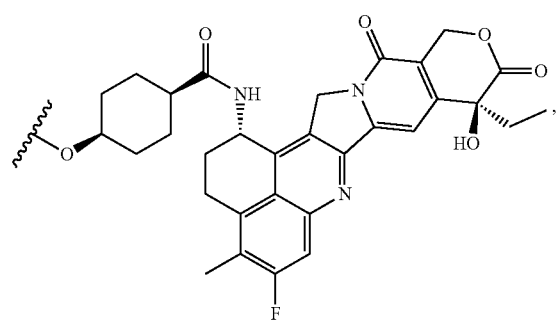
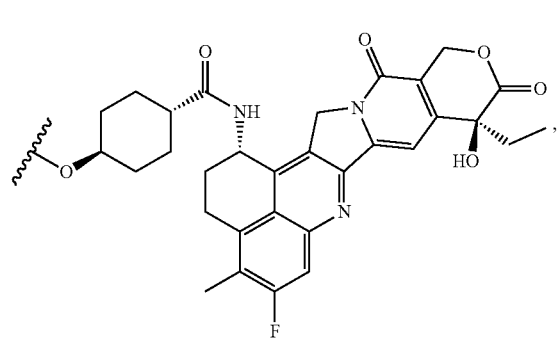
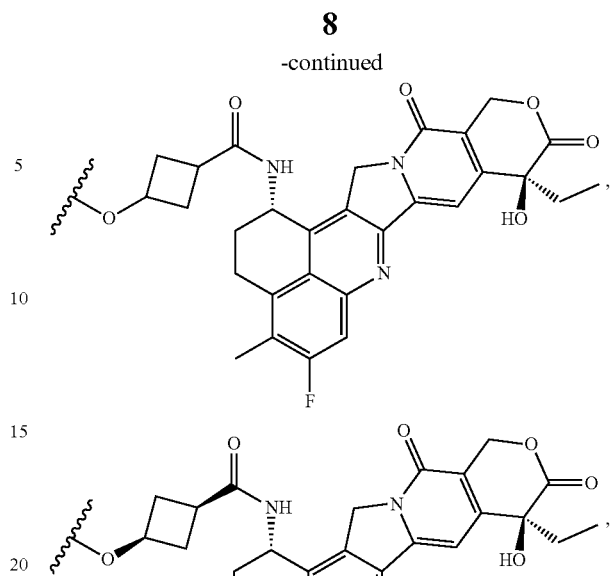
-continued
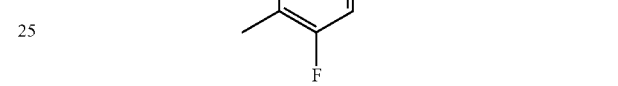
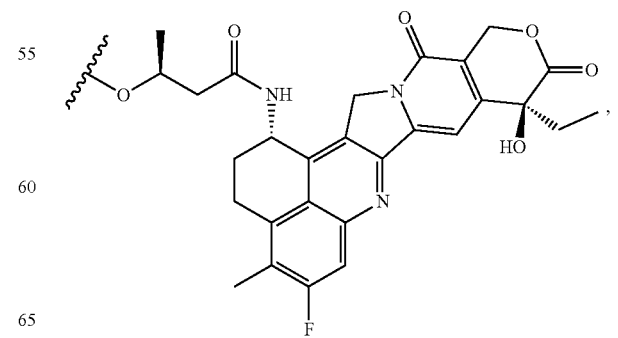

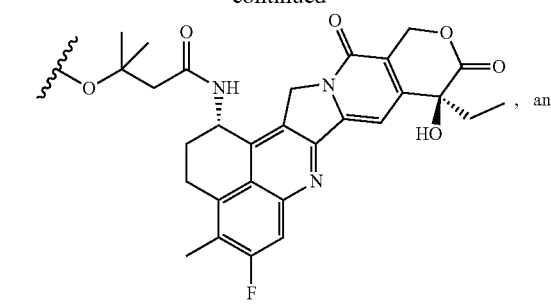
, and
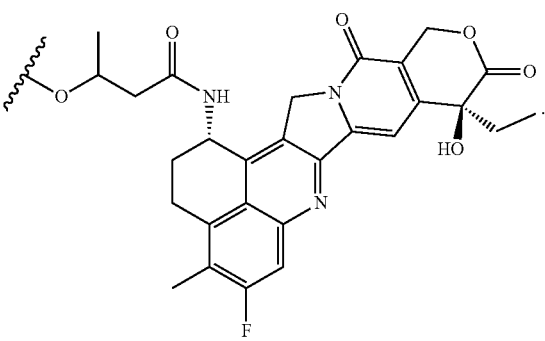
In some embodiments, in the antibody-drug conjugate provided herein, the linker unit L is —$L_a$—$L_b$—$L_c$—, wherein
—$L_a$— is
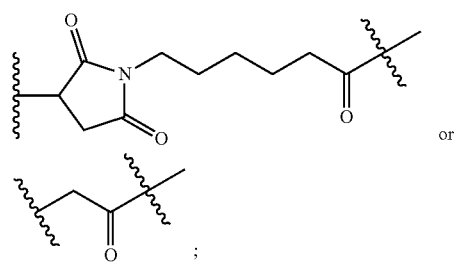
or
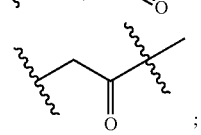
;
—$L_b$— is selected from the group consisting of:
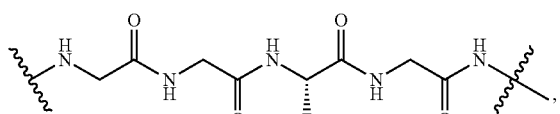
,
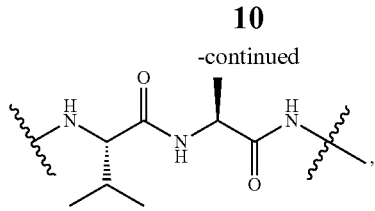
,
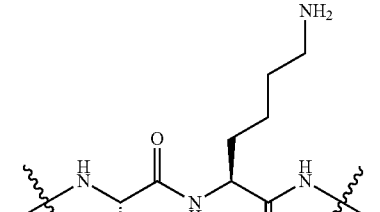
,
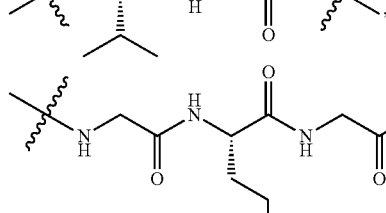
,
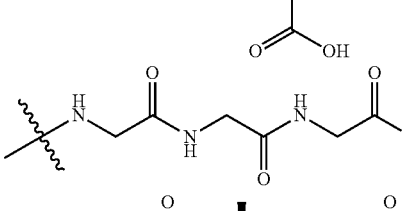
, and
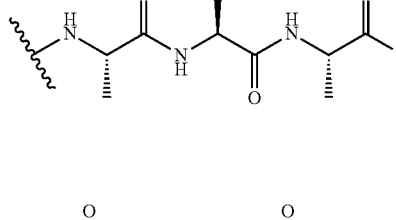
,
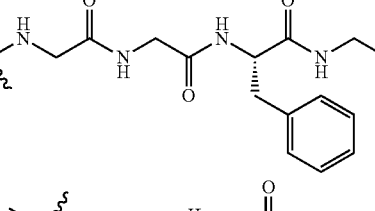
,
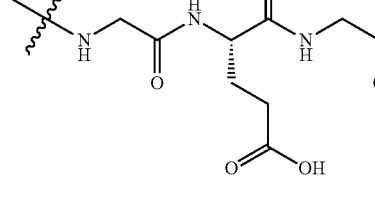
and
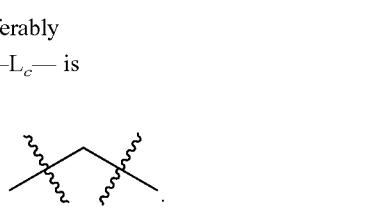
;
preferably
—$L_c$— is
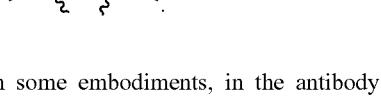
.
In some embodiments, in the antibody-drug conjugate provided herein, the linker unit L has an $L_a$ end linked to Ab and an $L_c$ end linked to linker unit M.

In some embodiments, in the antibody-drug conjugate provided herein, the linker unit L is

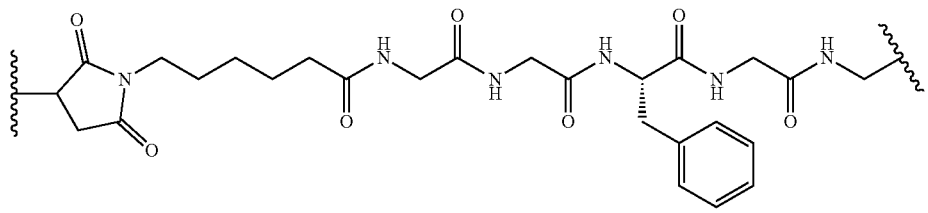 [SMILES: *CNC(=O)CNC(=O)[C@H](Cc1ccccc1)NC(=O)CNC(=O)CNC(=O)CCCCCN1C(=O)CC(*)C1=O]

In some embodiments, in the antibody-drug conjugate provided herein, the linker unit L is

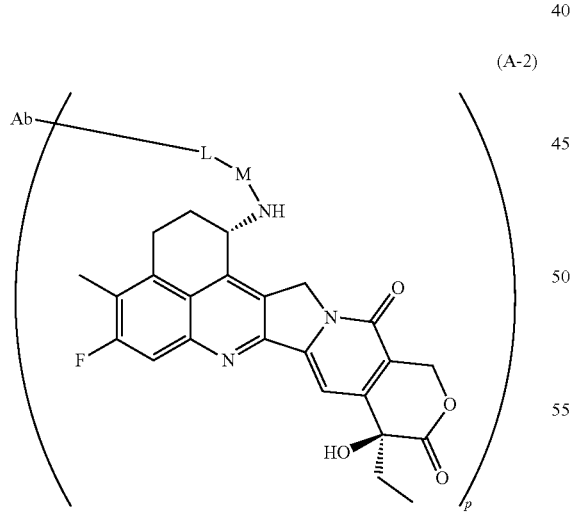

In some embodiments, the antibody-drug conjugate provided herein is of a structure shown as formula (A-2):

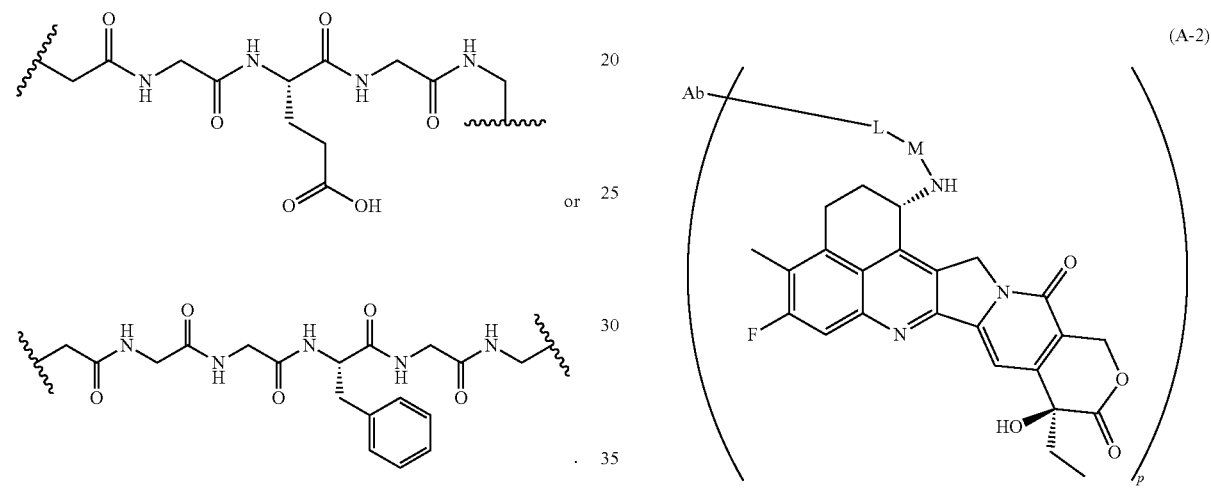

wherein, p represents an average connection number, and p is selected from the group consisting of integers or decimals from 1 to 10;

Ab, M and L are as described in any one of the solutions of the present application.

In some embodiments, the antibody-drug conjugate provided herein is of a structure shown as formula (A-2):

(A-2)

wherein, p represents an average connection number, and p is selected from the group consisting of integers or decimals from 1 to 10;

Ab is the B7H3-targeting antibody or the antigen-binding fragment thereof comprising: HCDR1 comprising an amino acid sequence as set forth in SEQ ID NO: 1, HCDR2 comprising an amino acid sequence as set forth in SEQ ID NO: 2, HCDR3 comprising an amino acid sequence as set forth in SEQ ID NO: 3, LCDR1 comprising an amino acid sequence as set forth in SEQ ID NO: 4, LCDR2 comprising an amino acid sequence as set forth in SEQ ID NO: 5, and LCDR3 comprising an amino acid sequence as set forth in SEQ ID NO: 6;

M is —$L^2$—$L^1$—C(O)—;

$L^2$ is —O— or —S—, preferably —O—;

$L^1$ is —(C($R^{1a}$)($R^{1b}$))$_m$—CH$_2$—;

m is selected from the group consisting of 1, 2, 3, and 4, preferably 1 and 2;

$R^{1a}$ and $R^{1b}$ may each independently be hydrogen, halogen, or $C_1$-$C_6$ alkyl optionally substituted with 1, 2, or 3 R;

each R may independently be hydrogen or halogen;

L is
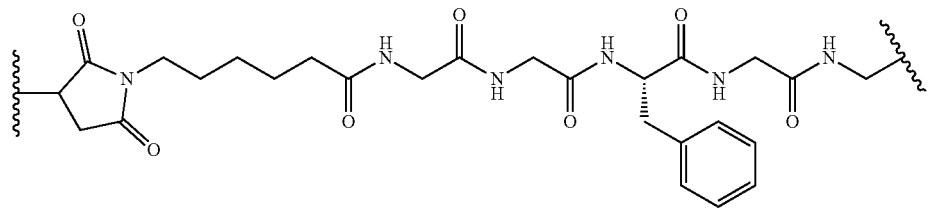 [SMILES: *CNC(=O)CNC(=O)[C@H](Cc1ccccc1)NC(=O)CNC(=O)CNC(=O)CCCCCN1C(=O)CC(*)C1=O]
In some embodiments, in the antibody-drug conjugate provided herein, p is an integer or a decimal from 2 to 8; for example, p is an integer or a decimal from 4 to 8, for example, p is an integer or a decimal from 4 to 6 or from 6 to 8.
In some embodiments, the antibody-drug conjugate provided herein is of a structure shown as formula (A-2a) or formula (A-2b):
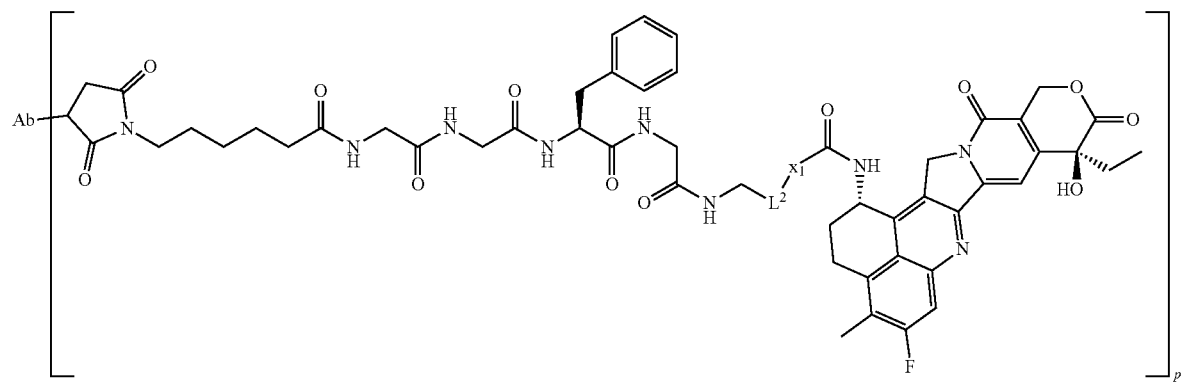
(A-2a)
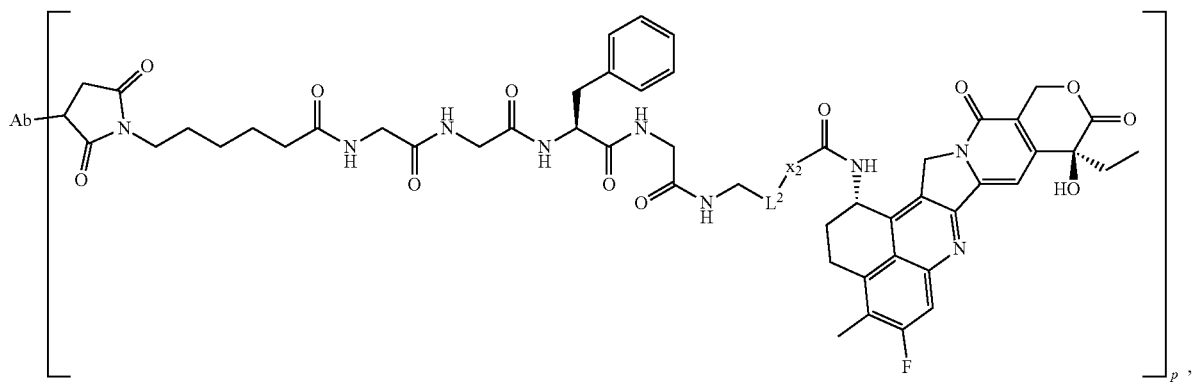
(A-2b)

wherein,
p represents an average connection number, and p is selected from the group consisting of integers or decimals from 1 to 10, preferably integers or decimals from 2 to 8, for example, p is an integer or a decimal from 4 to 8, for example, p is an integer or a decimal from 4 to 6 or from 6 to 8;
Ab is the B7H3-targeting antibody or the antigen-binding fragment thereof comprising: HCDR1 comprising an amino acid sequence as set forth in SEQ ID NO: 1, HCDR2 comprising an amino acid sequence as set forth in SEQ ID NO: 2, HCDR3 comprising an amino acid sequence as set forth in SEQ ID NO: 3, LCDR1 comprising an amino acid sequence as set forth in SEQ ID NO: 4, LCDR2 comprising an amino acid sequence as set forth in SEQ ID NO: 5, and LCDR3 comprising an amino acid sequence as set forth in SEQ ID NO: 6;

$L^2$ is —O— or —S—, preferably —O—;
$X_1$ is selected from the group consisting of $C_3$-$C_6$ saturated cycloalkyl optionally substituted with 1, 2, or 3 $R^{2a}$;
$X_2$ is selected from the group consisting of —(C($R^{1a}$)($R^{1b}$))$_m$—CH$_2$—;
m is selected from the group consisting of 1, 2, 3, and 4, preferably 1 and 2;
$R^{1a}$ $R^{1b}$ and $R^{2a}$ may each independently be hydrogen, halogen, or $C_1$-$C_6$ alkyl optionally substituted with 1, 2, or 3 R;
each R may independently be hydrogen or halogen.

In some embodiments, the antibody-drug conjugate provided herein is selected from the group consisting of the following structural formulas:

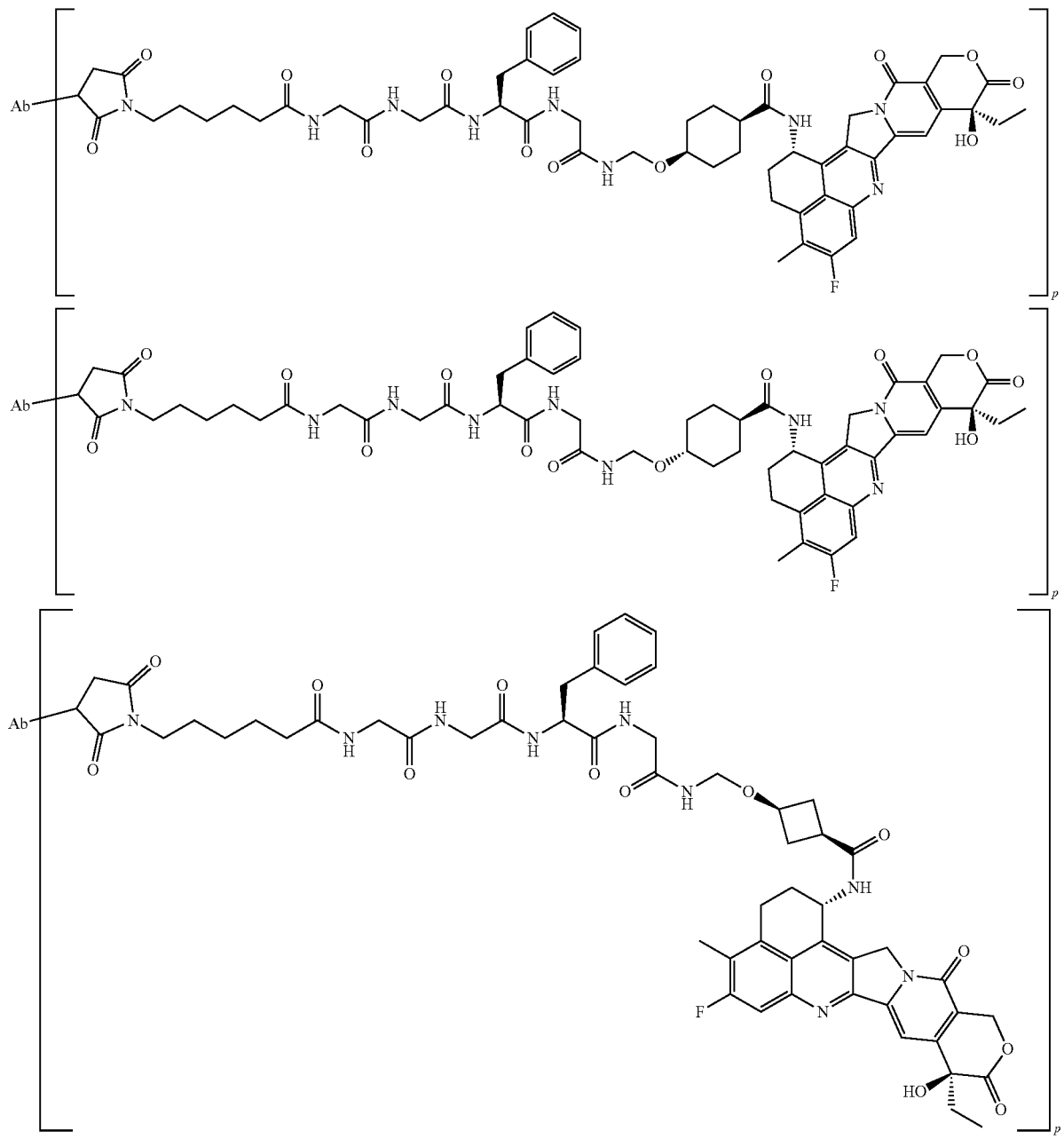

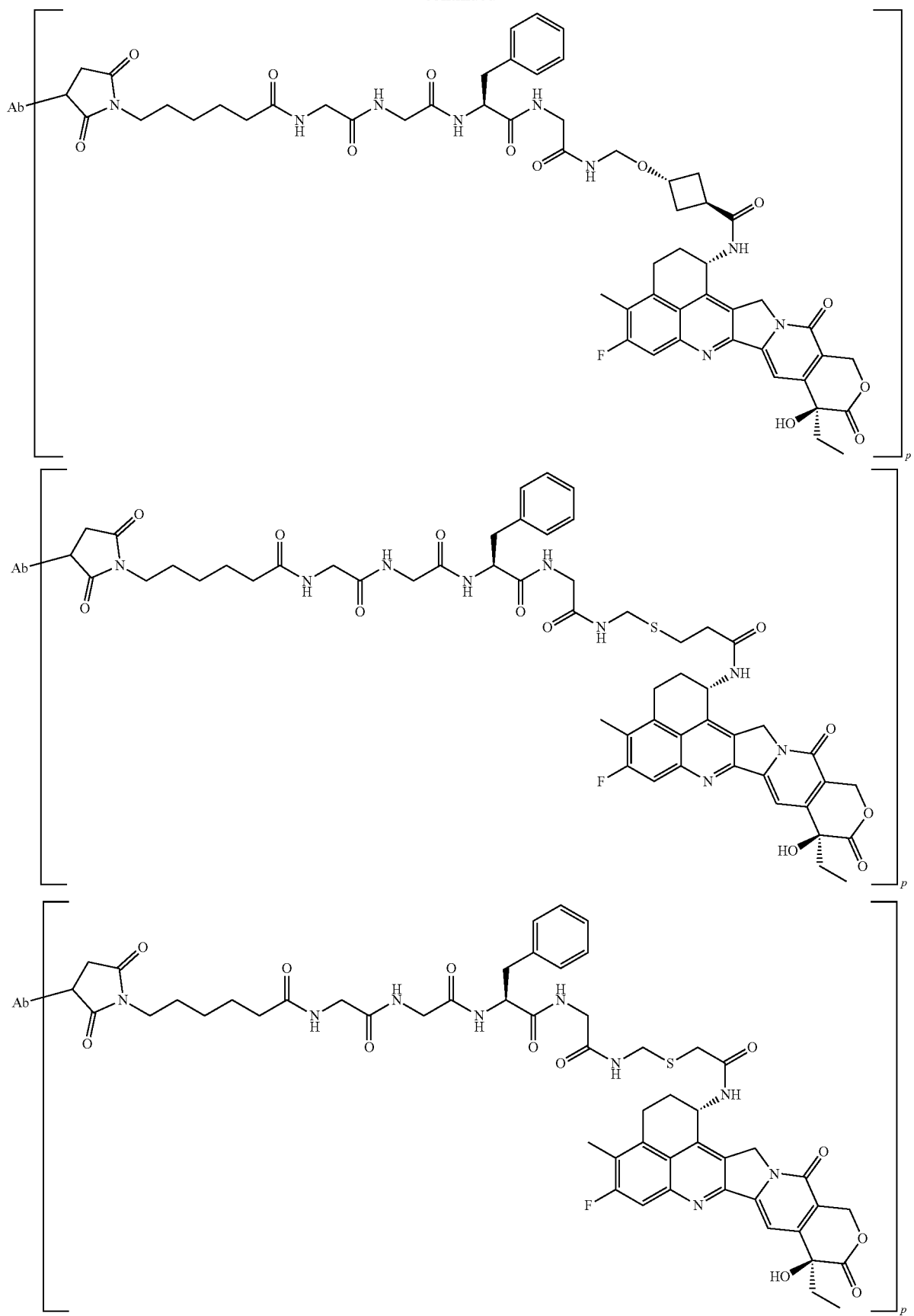

-continued
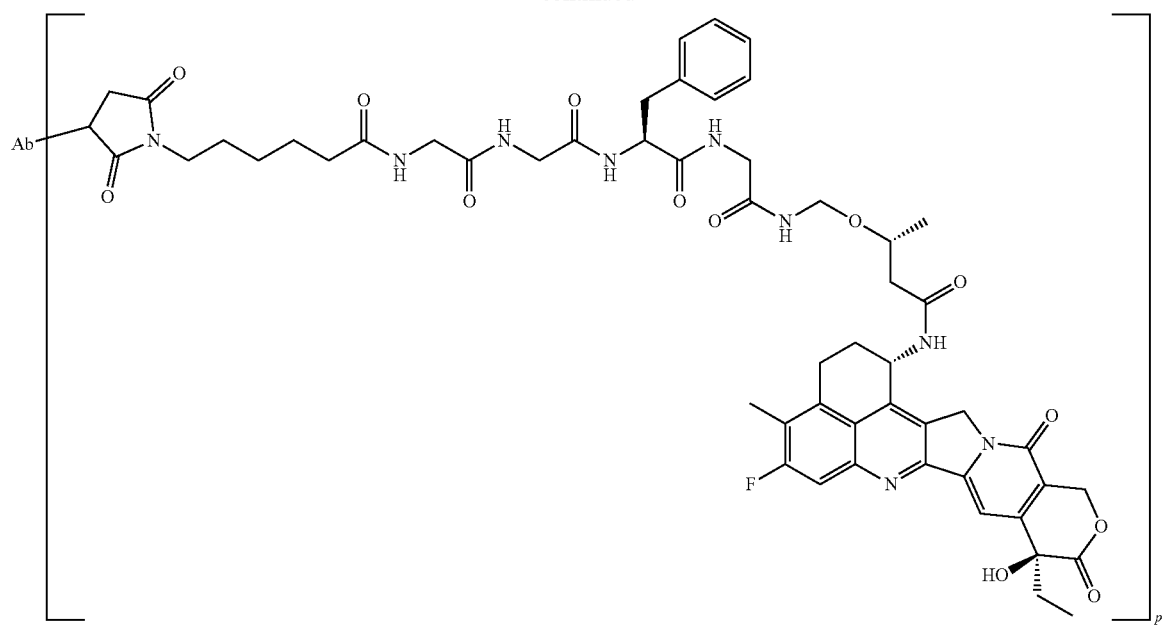
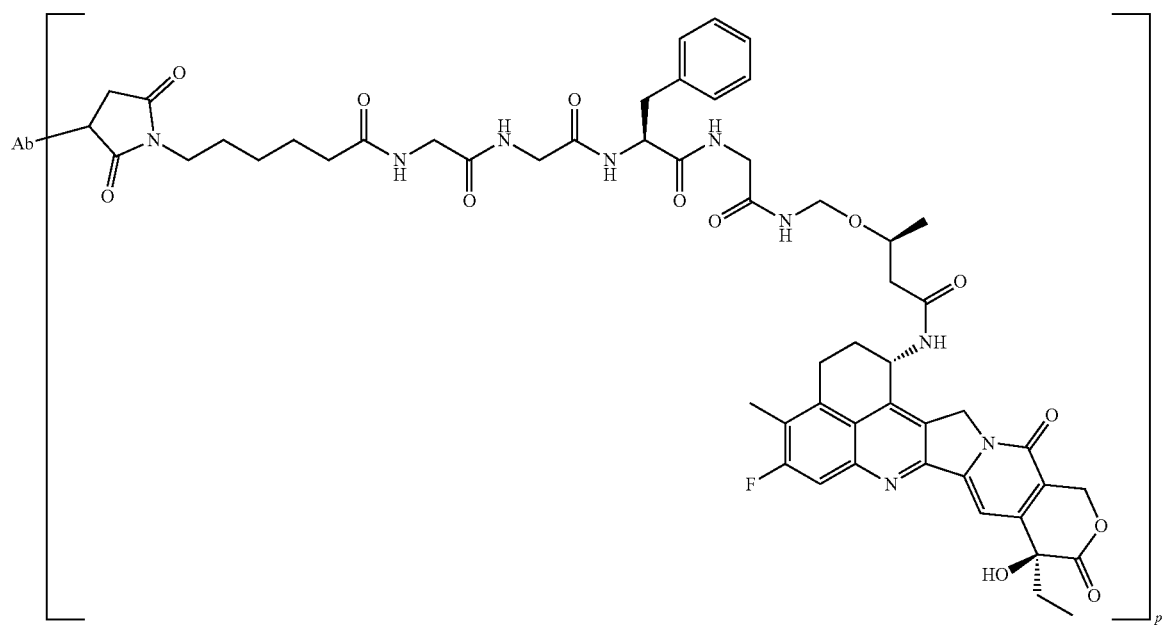

-continued

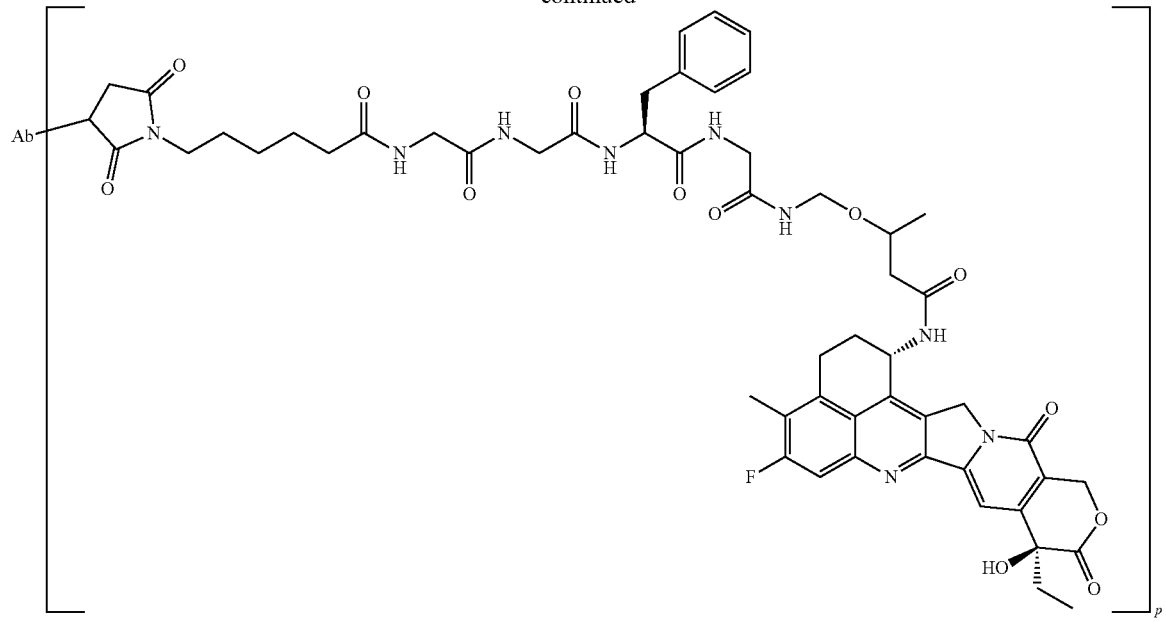

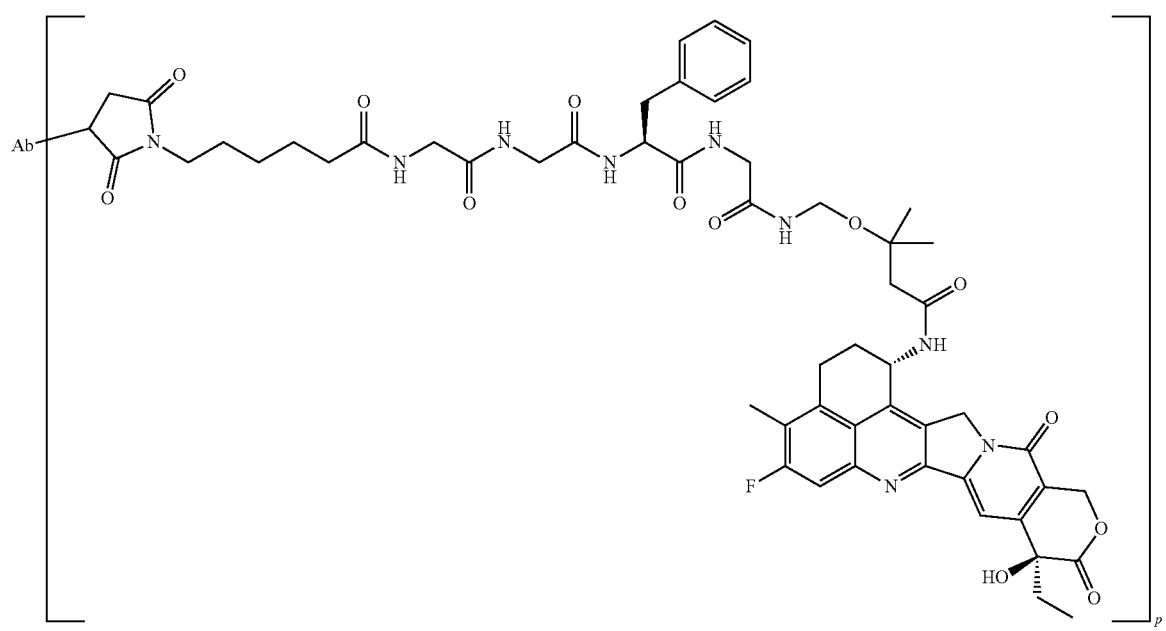

wherein, p represents an average connection number, and p is selected from the group consisting of integers or decimals from 1 to 10, preferably integers or decimals from 2 to 8, for example, p is an integer or a decimal from 4 to 8, for example, p is an integer or a decimal from 4 to 6 or from 6 to 8; Ab is as described in any one of the solutions of the present application.

In some embodiments, in the antibody-drug conjugate provided herein or a pharmaceutically acceptable salt thereof, the antibody-drug conjugate is selected from the group consisting of:

23 24
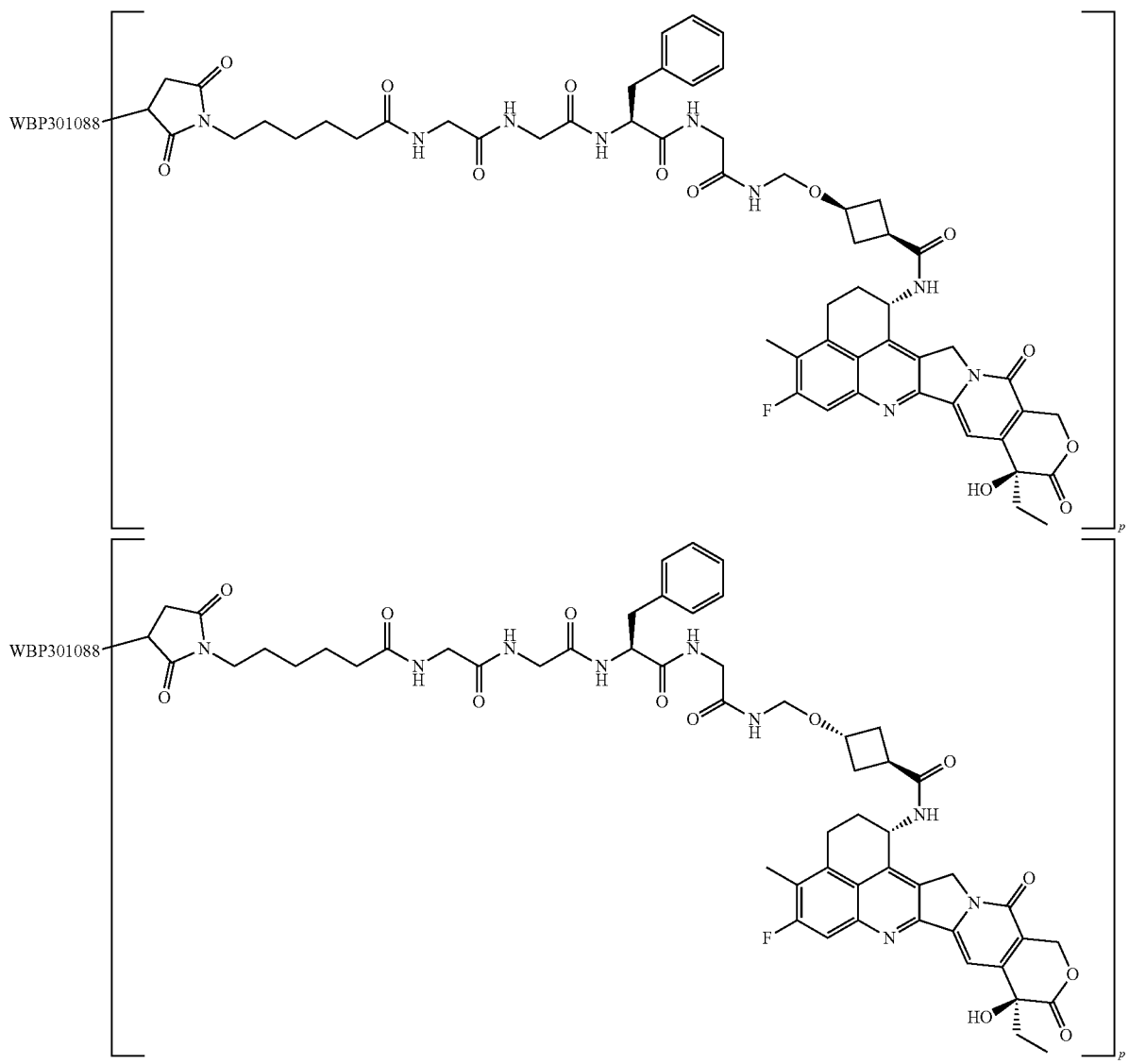
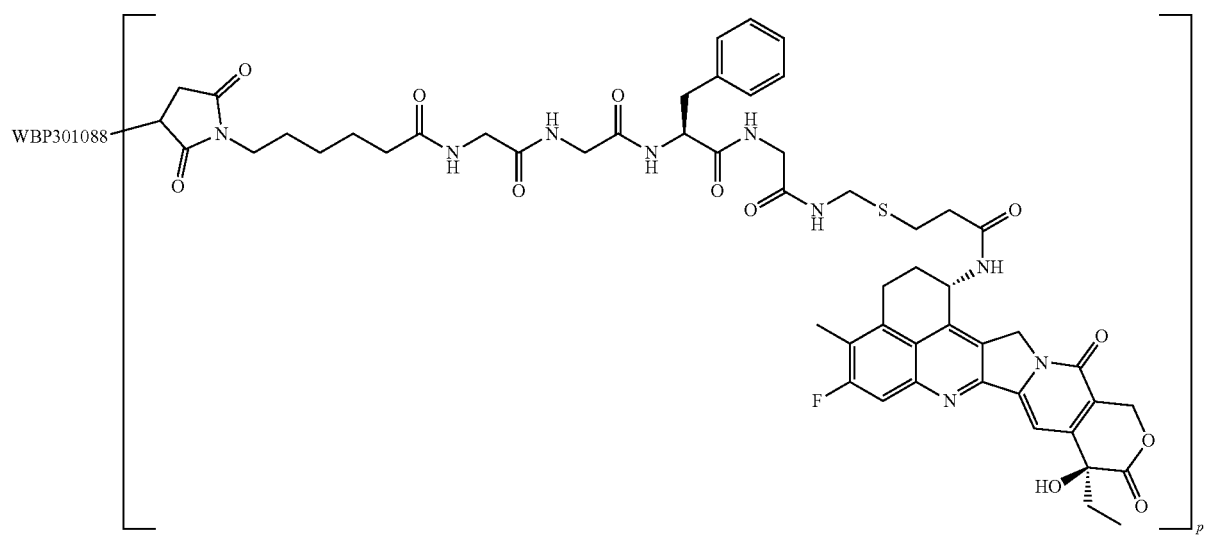

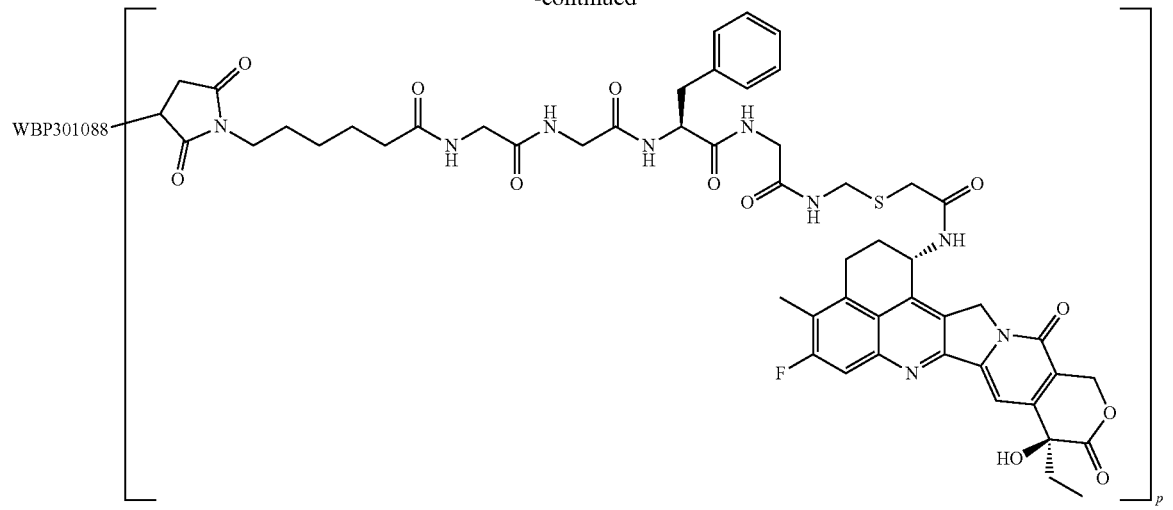
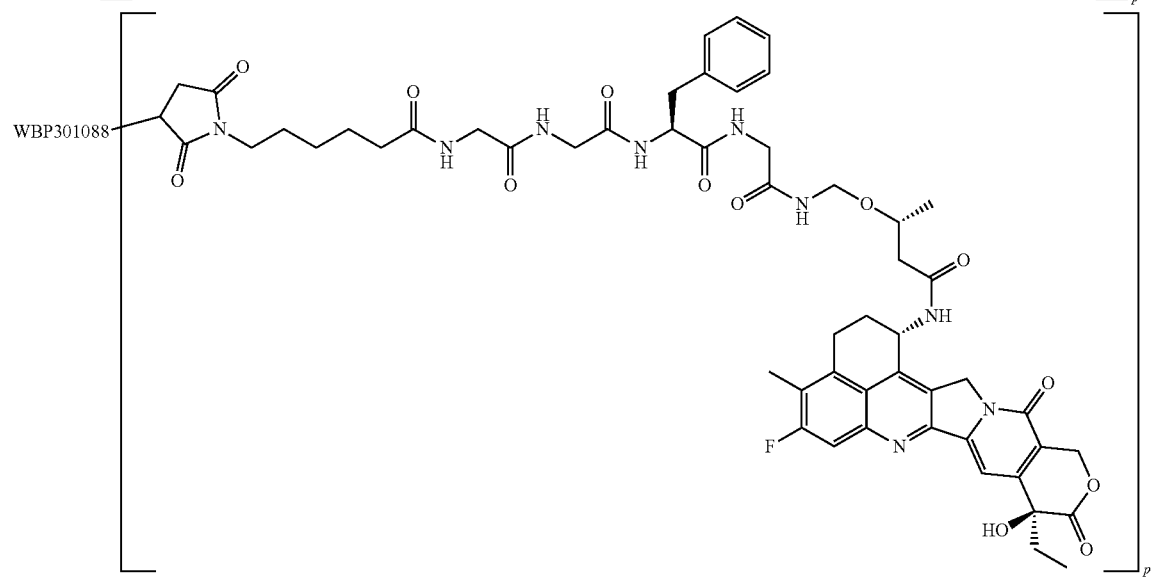
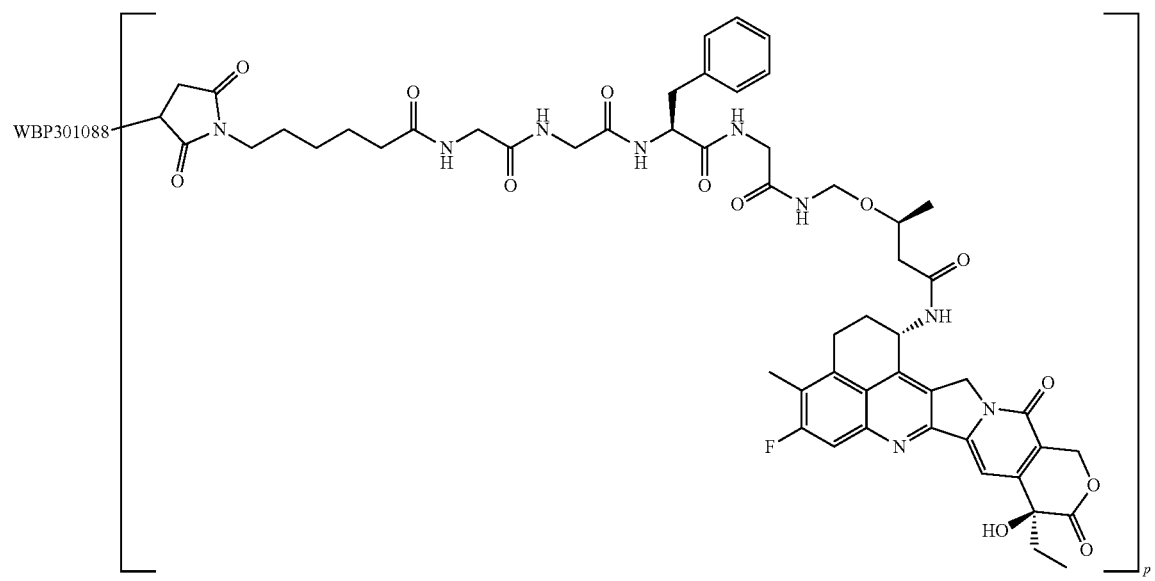

-continued

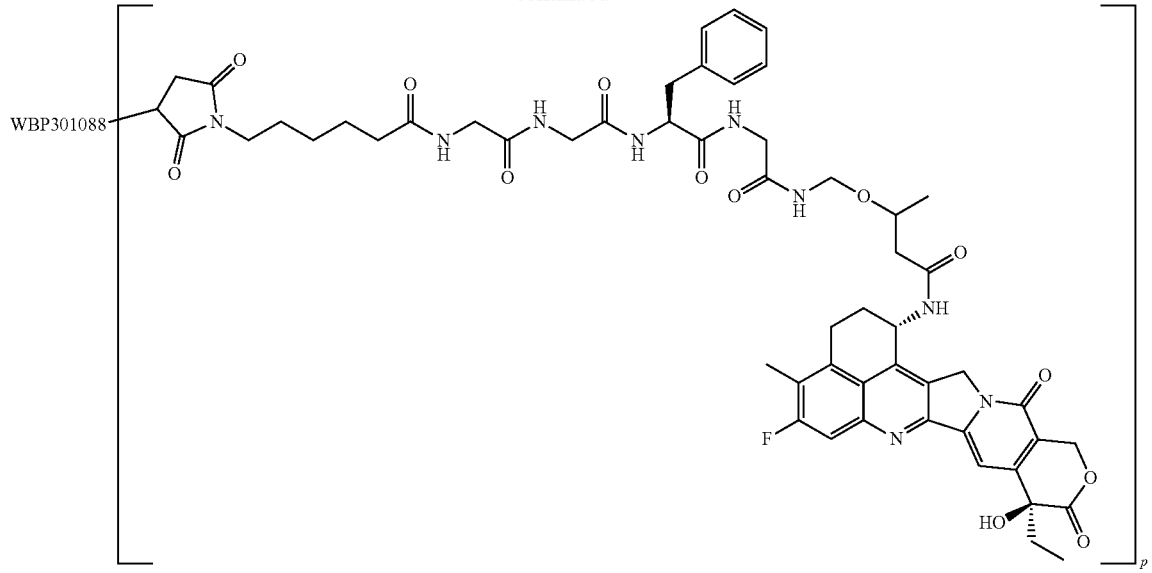

wherein, p represents an average connection number, and p is selected from the group consisting of integers or decimals from 1 to 10, preferably integers or decimals from 2 to 8, for example, p is an integer or a decimal from 4 to 8, for example, p is an integer or a decimal from 4 to 6 or from 6 to 8, for example, p is 7.45, 5.68 or 4.02; WBP301088 is an anti-B7H3 antibody comprising a heavy chain as set forth in SEQ ID NO: 12 and a light chain as set forth in SEQ ID NO: 13.

In some embodiments, in the antibody-drug conjugate provided herein or a pharmaceutically acceptable salt thereof, the antibody-drug conjugate is selected from the group consisting of:

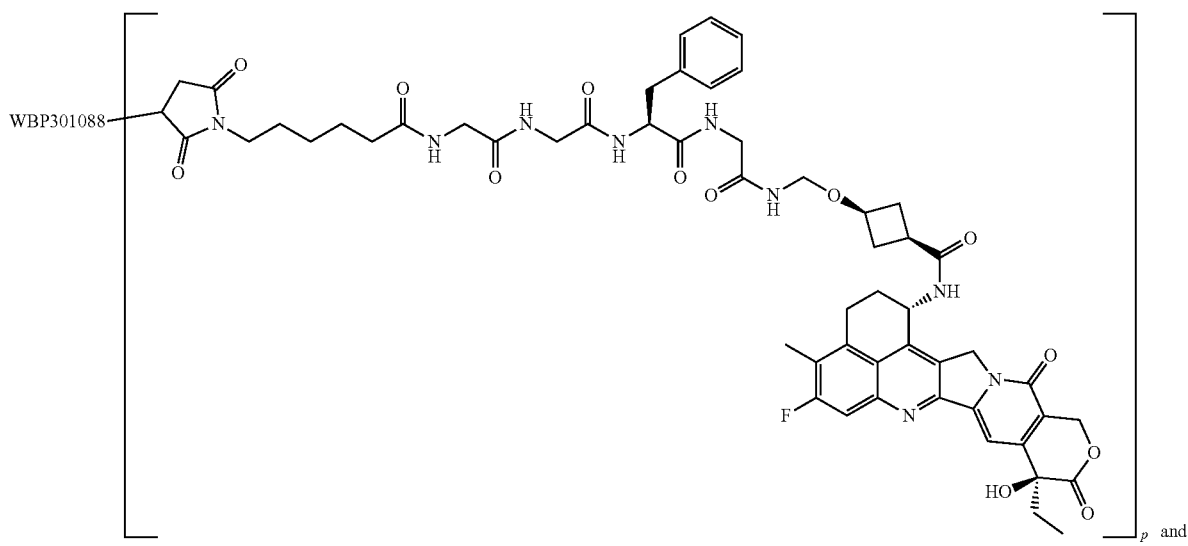

-continued

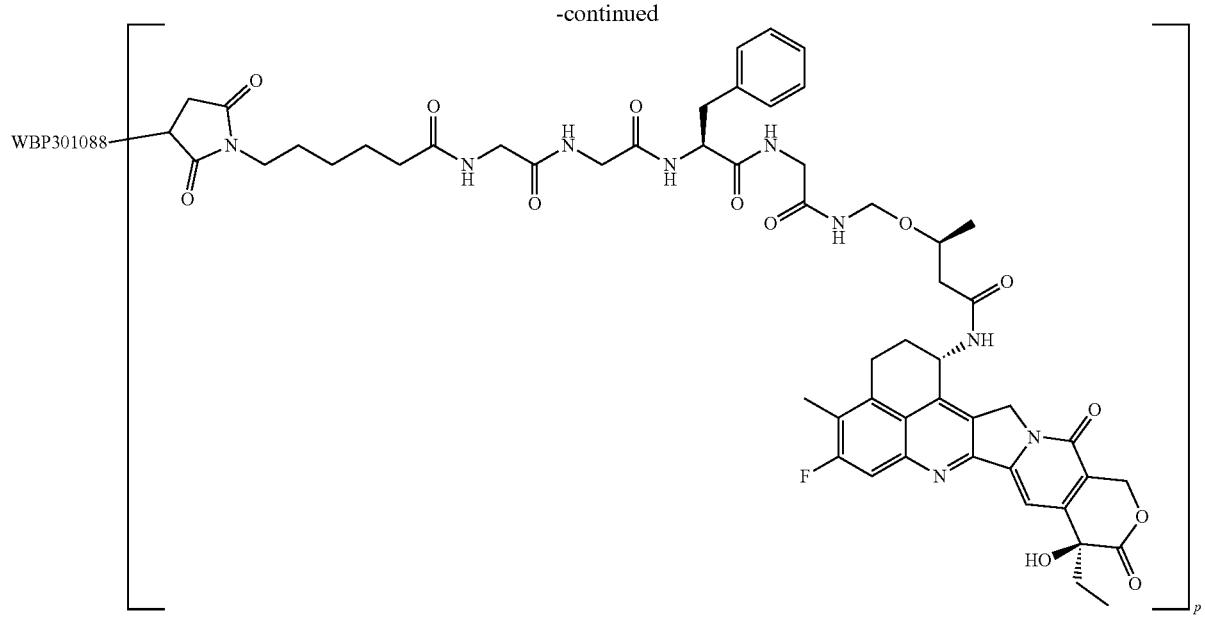

wherein,
p represents an average connection number, and p is selected from the group consisting of integers or decimals from 1 to 10, preferably integers or decimals from 2 to 8, for example, p is an integer or a decimal from 4 to 8, for example, p is an integer or a decimal from 4 to 6 or from 6 to 8, for example, p is 7.45, 5.68 or 4.02;

WBP301088 is an anti-B7H3 antibody comprising a heavy chain amino acid sequence as set forth in SEQ ID NO: 12 and a light chain amino acid sequence as set forth in SEQ ID NO: 13. In some embodiments, in the antibody-drug conjugate described herein, the average connection number p may be an integer or a decimal from 2 to 8. For example, the average connection number p may be an integer or a decimal from 3 to 8. For example, the average connection number p may be an integer or a decimal from 1 to 2, 2 to 3, 3 to 4, 4 to 5, 5 to 6, 6 to 7, 7 to 8, 8 to 9, or 9 to 10.

In yet another aspect, the present invention provides a pharmaceutical composition, which comprises the antibody-drug conjugate described herein, or a pharmaceutically acceptable salt thereof, and a pharmaceutically acceptable carrier or excipient.

In yet another aspect, the present invention provides use of the antibody-drug conjugate, the pharmaceutically acceptable salt thereof described herein or the pharmaceutical composition described herein in preparing a medicament for treating and/or preventing a B7H3-mediated disease or condition, wherein preferably, the disease or condition is cancer. Preferably, the disease or condition is a disease or condition in which B7H3 is positively expressed.

In yet another aspect, the present invention provides a method for treating and/or preventing a B7H3-mediated disease or condition, which comprises administering to a subject in need the antibody-drug conjugate or the pharmaceutically acceptable salt thereof described herein or the pharmaceutical composition described herein, wherein preferably, the disease or condition is cancer. Preferably, the disease or condition is a disease or condition in which B7H3 is positively expressed.

In yet another aspect, the present invention provides the antibody-drug conjugate, the isomers thereof, or the pharmaceutically acceptable salt or the pharmaceutical composition thereof described herein for treating and/or preventing a B7H3-mediated disease or condition, wherein preferably, the disease or condition is cancer. Preferably, the disease or condition is a disease or condition in which B7H3 is positively expressed.

In some embodiments, the cancer of the present invention is selected from the group consisting of breast cancer, neurological tumors, melanoma, lung cancer, head and neck cancer, colorectal cancer, pancreatic cancer, gastric cancer, renal cancer, bladder cancer, prostate cancer, ovarian cancer, cervical cancer, glioblastoma, esophageal cancer, renal cell carcinoma, endometrial cancer, skin cancer, testicular cancer, thyroid cancer, urothelial cancer, lymphoma (such as non-Hodgkin lymphoma), chronic lymphocytic leukemia, diffuse large B-cell lymphoma, and multiple myeloma.

In yet another aspect, the present invention provides a pharmaceutical combination, which comprises the antibody-drug conjugate or the pharmaceutically acceptable salt thereof described herein, or the pharmaceutical composition described herein, and one or more additional therapeutic agents.

In yet another aspect, the present invention provides a kit, which comprises the antibody-drug conjugate described herein or the pharmaceutical composition described herein.

DETAILED DESCRIPTION

Figure 1:
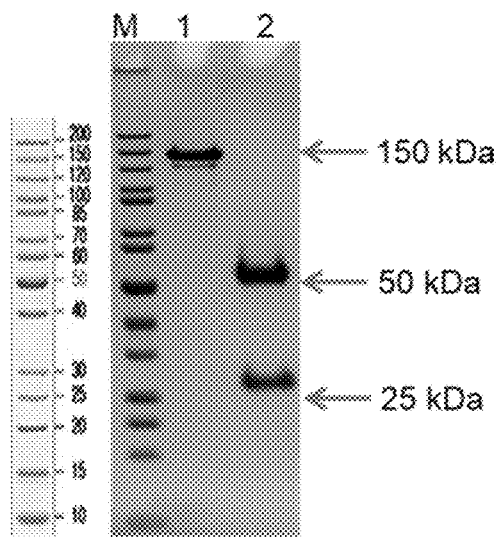
FIG. 1 shows SDS-PAGE results of W301088-1.145.16-z3-p1-uIgG1KV320. M: PageRuler™ Unstained Protein Ladder; lane 1: W301088-1.145.16-z3-p1-uIgG1KV320, non-reducing; lane 2: W301088-1.145.16-z3-p1-uIgG1KV320, reducing; gel information: NuPAGE, Novex 4-12% Bis-Tris gel.

The embodiments of the present invention are described below with reference to specific examples, and other advantages and effects of the present invention will be readily apparent to those skilled in the art from the disclosure of the present specification.

Definitions of Terms

Unless otherwise stated, embodiments of the present invention will employ conventional techniques of molecular biology (including recombinant techniques), microbiology, cytobiology, biochemistry and immunology, which are all within the skill of the art.

In order to facilitate the understanding of the present invention, some technical and scientific terms are specifically defined as follows. Unless otherwise specifically defined herein, all technical and scientific terms used herein have the same meaning as commonly understood by those of ordinary skill in the art to which the present invention belongs. For definitions and terminology in the art, those skilled in the art can refer specifically to Current Protocols in Molecular Biology (Ausubel F. et al., John Wiley & Sons, New York, 2000). Abbreviations for amino acid residues are standard three-letter and/or single-letter codes used in the art to denote one of the 20 commonly used L-amino acids. The singular forms used herein (including claims) include their plural forms, unless otherwise specified in the context explicitly.

The term "about" generally means varying by 0.5%-10% above or below the stated value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% above or below the stated value.

The term "antibody" or "Ab" herein is used in the broadest sense, which encompasses various antibody structures, including polyclonal antibodies, monospecific and multispecific antibodies (e.g. bispecific antibodies). A native intact antibody generally is a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region (VH) and a heavy chain constant region (CH). A heavy chain constant region consists of 3 domains (CH1, CH2 and CH3). Each light chain consists of a light chain variable region (VL) and a light chain constant region (CL). VH and VL region can further be divided into hypervariable regions (called complementary determining regions (CDR)), which are interspaced by relatively conservative regions (called framework region (FR)). Each VH and VL consists of 3 CDRs and 4 FRs in the following order: FR1, CDR1, FR2, CDR2, FR3, CDR3, FR4 from N-terminal to C-terminal. The variable region (VH and VL) of each heavy/light chain pair forms antigen binding sites, respectively. The extent of the framework region and CDRs can be precisely identified using methodology known in the art, for example, by the Kabat definition, the definitions at Dr. Martin's website, the Chothia definition, the AbM definition, the EU definition, and the contact definition, all of which are well known in the art. See, e.g., Kabat, E. A., et al. (1991) Sequences of Proteins of Immunological Interest, Fifth Edition, U.S. Department of Health and Human Services, NIH Publication No. 91-3242; Martin A.

"Antibody bioinformatics website of Dr. Andrew Martin's lab at UCL," last updated on 31 Jul. 2018; Chothia et al., (1989) Nature 342:877; Chothia, C. et al. (1987) J. Mol. Biol. 196:901-917, Al-lazikani et al (1997) J. Molec. Biol. 273:927-948; Edelman et al., Proc Natl Acad Sci U S A. 1969 May; 63(1):78-85; and Almagro, J. Mol. Recognit. 17:132-143 (2004). See also hgmp.mrc.ac.uk and bioinf.org.uk/abs. Correspondence or alignments between numberings according to different definitions can for example be found at http://www.imgt.org/ (see also Giudicelli V et al. IMGT, the international ImMunoGeneTics database. Nucleic Acids Res. (1997) 25:206-11; Lefranc M P et al. Unique database numbering system for immunogenetic analysis. Immunol Today (1997) 18:509; and Lefranc M P et al., IMGT unique numbering for immunoglobulin and T cell receptor variable domains and Ig superfamily V-like domains. Dev Comp Immunol. (2003) 27:55-77). Antibodies may be of different antibody isotypes, for example, IgG (e.g., IgG1, IgG2, IgG3 or IgG4 subtype), IgA1, IgA2, IgD, IgE or IgM antibody. The term "B7H3", also known as CD276 antigen, refers to a type I transmembrane protein that belongs to the B7 family and contains an extracellular domain consisting of a single IgV-IgC domain. The proteins of the B7 family contain extracellular IgV-like and IgC-like domains and have short cytoplasmic tails. B7H3 is an immune checkpoint molecule that is abnormally overexpressed in a variety of cancers. The amino acid sequences of B7H3 proteins include full-length B7H3 proteins (e.g., the human 4IgB7H3 protein or human 2IgB7H3 protein), or the extracellular domain of B7H3 (B7H3 ECD) or fragments containing B7H3 ECD, or B7H3-ECD fusion proteins. Exemplary sequences of B7H3 proteins are shown under Uniprot ID: Q5ZPR3 (human 4IgB7H3) and Genebank accession Nos. NP_001019907 (human), NP_001316557 (human), NP_001316558 (human), NP_079516 (human) and NP_598744 (mouse). Cynomolgus monkey B7H3 has about 97% and 88% amino acid sequence homology with human and mouse B7H3, respectively.

The term "antibody binding to B7H3" or "anti-B7H3 antibody" includes antibodies and antigen-binding fragments that specifically recognize B7H3 proteins, and antibodies and antigen-binding fragments that specifically bind to B7H3 proteins. As used herein, "anti-B7H3 antibody" includes monovalent antibodies with single specificity, and bispecific antibodies comprising a first antigen-binding site that binds to B7H3 and a second antigen-binding site that binds to a second antigen.

A "monoclonal antibody" refers to an antibody obtained from a substantially homogeneous population of antibodies, i.e., the antibodies composing the population are identical except for possible naturally occurring mutations that may be present in minor amounts. A monoclonal antibody is highly specific and targets a single antigen epitope. In contrast, conventional (polyclonal) antibody preparations typically include a large number of antibodies targeting (or specific for) different epitopes. The modifier "monoclonal" indicates the characteristic of an antibody obtained from a substantially homogeneous population of antibodies, and is not to be construed as producing the antibody by any particular method.

The term "full-length antibody" refers to a naturally occurring immunoglobulin molecule, comprising four peptide chains, in which two heavy (H) chains (about 50-70 kDa in total length) and two light (L) chains (about 25 kDa in total length) are linked to each other by disulfide bonds. Each heavy chain consists of a heavy chain variable region (abbreviated herein as VH) and a heavy chain constant region (abbreviated herein as CH). The heavy chain constant region consists of 3 domains (CH1, CH2 and CH3). Each light chain consists of a light chain variable region (abbreviated herein as VL) and a light chain constant region (abbreviated herein as CL). The light chain constant region consists of one domain CL. The VH and VL regions can be further divided into complementarity determining regions (CDRs) with high variability and more conservative regions called framework regions (FRs) that are spaced apart by the CDRs. Each VH or VL region consists of 3 CDRs and 4 FRs arranged in the following order from the amino terminus to the carboxyl terminus: FR1, CDR1, FR2, CDR2, FR3, CDR3, FR4. The variable regions of the heavy and light chains comprise binding domains that interact with antigens. The constant regions of an antibody can mediate the binding of immunoglobulins to host tissues or factors, including the binding of various cells of the immune system (e.g., effector cells) to the first component (Clq) of a classical complement system.

The term "CDR" refers to a complementarity determining region within an antibody variable sequence. There are 3 CDRs in each of the heavy chain and light chain variable regions, which are named HCDR1, HCDR2 and HCDR3 for the heavy chain variable region, or LCDR1, LCDR2 and LCDR3 for the light chain variable region. The precise amino acid sequence boundaries of the variable region CDRs of the antibodies of the present invention can be determined using any of a number of well-known schemes, including Chothia based on the three-dimensional structure of antibodies and the topology of the CDR loops (Chothia et al., (1989) Nature 342: 877-883; Al-Lazikani et al., Standard conformations for the canonical structures of immunoglobulins, Journal of Molecular Biology, 273, 927-948 (1997)), Kabat based on antibody sequence variability (Kabat et al., Sequences of Proteins of Immunological Interest, 4th edition, U.S. Department of Health and Human Services, National Institutes of Health (1987)), AbM (University of Bath), Contact (University College London), International ImMunoGeneTics database (IMGT) (1999 Nucleic Acids Research, 27, 209-212), and North CDR definition based on the affinity propagation clustering using a large number of crystal structures. The boundaries of the CDRs of the antibodies disclosed herein can be determined by one skilled in the art according to any scheme (e.g., different assignment systems or combinations) in the art.

The term "antigen-binding fragment" or "antibody fragment" of an antibody ("parent antibody") includes a fragment or a derivative of the antibody, generally including at least one fragment of an antigen-binding region or variable region (e.g., one or more CDRs) of a parent antibody, which retains at least some of the binding specificity of the parent antibody. Examples of binding fragments of an antibody include, but are not limited to, Fab, Fab', F(ab')$_2$ and Fv fragments; a bispecific antibody; a linear antibody; a single-chain antibody molecule, such as scFv; and a nanobody and a multispecific antibody formed by fragments of the antibody. An antigen-binding fragment or a derivative generally retains at least 10% of the antigen-binding activity of the parent antibody when the activity of binding to antigen is expressed on a molar concentration basis. Preferably, the antigen-binding fragment or the derivative retains at least 20%, 50%, 70%, 80%, 90%, 95% or 100% or more of the antigen-binding affinity of the parent antibody. It is also contemplated that an antigen-binding fragment of an antibody may include conservative amino acid substitutions that do not significantly alter its bioactivity (referred to as "conservative variants" or "function-conservative variants" of the antibody) or non-conservative acid substitutions.

A "chimeric antibody" is an antibody having the variable domains of a first antibody and the constant domains of a second antibody, wherein the first and second antibodies are from different species. Typically, the variable domains are obtained from an antibody of an experimental animal such as a rodent ("parent antibody"), and the constant domain sequences are obtained from a human antibody, such that the resulting chimeric antibody is less likely to induce an adverse immune response in a human subject as compared to the parent rodent antibody.

A "humanized antibody" refers to an antibody form containing sequences from both human and non-human (such as mouse and rat) antibodies. In general, a humanized antibody comprises substantially all of at least one, and typically two, variable domains, in which all or substantially all of the hypervariable loops correspond to those of a non-human immunoglobulin and all or substantially all of the framework regions (FRs) are those of a human immunoglobulin sequence. The humanized antibody may optionally comprise at least a portion of a human immunoglobulin constant region (Fc). In the present application, the term "halogen" generally refers to fluorine, chlorine, bromine or iodine, and it may be, for example, fluorine or chlorine.

In the present application, the term "alkyl" generally refers to a residue derived from an alkane by removal of a hydrogen atom. Alkyl may be substituted or unsubstituted, or replaced or unreplaced. The term "alkyl" generally refers to a saturated linear or branched aliphatic hydrocarbon group having a residue derived from the parent alkane by removal of hydrogen atoms from the same carbon atom or two different carbon atoms, and it may be a linear or branched group containing 1 to 20 carbon atoms, e.g., 1 to 12 carbon atoms, such as chain alkyl containing 1 to 6 carbon atoms. Non-limiting examples of alkyl include, but are not limited to, methyl, ethyl, n-propyl, isopropyl, n-butyl, etc. Alkyl may be substituted or unsubstituted, replaced or unreplaced. For example, when it is substituted, substitution with a substituent may be performed at any available linking site, and the substituent may be independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group. For example, when substituted with cycloalkyl, it is cycloalkylalkyl.

In the present application, the term "alkylene" generally refers to a saturated linear or branched aliphatic hydrocarbon group having 2 residues derived from the parent alkane by removal of two hydrogen atoms from the same carbon atom or two different carbon atoms, and it may be a linear or branched group containing 1 to 20 carbon atoms; for example, the term "methylene" may refer to a residue derived from a one-carbon atom group by removal of two hydrogen atoms. Methylene may be substituted or unsubstituted, replaced or unreplaced; for example, alkylene contains 1 to 12 carbon atoms, e.g., an alkylene group containing 1 to 6 carbon atoms. Non-limiting examples of alkylene include, but are not limited to, methylene (—CH$_2$—), 1,1-ethylidene (—CH(CH$_3$)—), 1,2-ethylidene (—CH$_2$CH2)—, 1,1-propylidene (—CH(CH$_2$CH$_3$)—), 1,2-propylidene (—CH$_2$CH(CH$_3$)—), 1,3-propylidene (—CH$_2$CH$_2$CH$_2$—), 1,4-butylidene (—CH$_2$CH$_2$CH$_2$CH$_2$—), 1,5-penttylidene (—CH$_2$CH$_2$CH$_2$CH$_2$CH$_2$—), etc. Alkylene may be substituted or unsubstituted, replaced or unreplaced. For example, when it is substituted, substitution with a substituent may be performed at any available linking point, and the substituent is preferably independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group. Methylene or alkylene may be substituted or unsubstituted.

The term "alkoxy" refers to —O-(alkyl) and —O-(unsubstituted cycloalkyl), wherein the alkyl or cycloalkyl is as defined herein. Non-limiting examples of alkoxy include: methoxy, ethoxy, propoxy, butoxy, cyclopropyloxy, cyclobutyloxy, cyclopentyloxy and cyclohexyloxy. Alkoxy may be optionally substituted or unsubstituted, and when it is substituted, the substituent is preferably one or more of the following groups independently selected from the group consisting of: alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio and heterocy cloalkylthio.

In the present application, the term "alkenyl" generally refers to a linear or branched hydrocarbon group containing one or more double bonds. Exemplary examples of alkenyl include allyl, homoallyl, vinyl, crotyl, butenyl, pentenyl, hexenyl, etc. Exemplary examples of C2-6 alkenyl containing more than one double bond include butadienyl, pentadienyl, hexadienyl, and hexatrienyl, as well as branched forms thereof. The positions of the unsaturated bonds (double bonds) may be any positions in the carbon chain. Alkenyl may be substituted or unsubstituted. For example, when it is substituted, substitution with a substituent may be performed at any available linking point, and the substituent is preferably independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a C$_{1-6}$ aliphatic group.

In the present application, the term "alkenylene" generally refers to a group having a residue derived from an alkene by removal of two hydrogen atoms from a carbon atom. For example, alkenylene may be acrol, vinylene, butenylene, pentenylene, hexenylene, etc. Alkenylene may be substituted or unsubstituted. For example, when it is substituted, substitution with a substituent may be performed at any available linking point, and the substituent is preferably independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)

$CH_2C(O)H$, —S(O)H, —S(O)$_2$H, —C(O)NH$_2$, —SO$_2$NH$_2$, —OC(O)H, —N(H)SO$_2$H or a $C_{1-6}$ aliphatic group.

In the present application, the term "alkynyl" generally refers to a linear or branched hydrocarbon group containing one or more triple bonds. The alkynyl may be unsaturated linear or branched alkynyl, e.g., ethynyl, 1-propynyl, propargyl, or butynyl. Alkynyl may be substituted or unsubstituted. For example, when it is substituted, substitution with a substituent may be performed at any available linking point, and the substituent is preferably independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a $C_{1-6}$ aliphatic group.

In the present application, the term "alkynylene" generally refers to a group having a residue derived from an alkyne by removal of two hydrogen atoms from a carbon atom. For example, alkynylene may be ethynylene, propynylene, propargylene, butynylene, etc. Alkynylene may be substituted or unsubstituted. For example, when it is substituted, substitution with a substituent may be performed at any available linking point, and the substituent is preferably independently optionally selected from the group consisting of one or more of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, and oxo, and it may, e.g., be hydrogen, protium, deuterium, tritium, halogen, —NO$_2$, —CN, —OH, —SH, —NH$_2$, —C(O)H, —CO$_2$H, —C(O)C(O)H, —C(O)CH$_2$C(O)H, —S(O)H, —S(O)$_2$H, —C(O)NH$_2$, —SO$_2$NH$_2$, —OC(O)H, —N(H)SO$_2$H or a $C_{1-6}$ aliphatic group.

In the present application, the term "aryl" generally refers to a group having a residue derived from an aromatic ring by removal of a hydrogen atom. The term "aromatic ring" may refer to a 6- to 14-membered all-carbon monocyclic ring or fused polycyclic ring (i.e., rings which share adjacent pairs of carbon atoms) having a conjugated π-electron system, and it may be 6- to 10-membered, such as benzene and naphthalene. The aromatic ring can be fused to a heteroaryl, heterocyclyl or cycloalkyl ring, wherein the ring connected to the parent structure is the aryl ring. Aryl may be substituted or unsubstituted, and when it is substituted, the substituent may be one or more of the following groups independently selected from the group consisting of: alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio. Aryl may be substituted or unsubstituted.

In the present application, the term "heteroaryl" generally refers to a group having a residue derived from a heteroaromatic ring by removal of a hydrogen atom from a carbon atom. The term "heteroaromatic ring" refers to a heteroaromatic system comprising 1 to 4 heteroatoms and 5 to 14 ring atoms, wherein the heteroatoms may be selected from the group consisting of: oxygen, sulfur and nitrogen. Heteroaryl may be 5- to 10-membered and may be 5- or 6-membered, such as furanyl, thienyl, pyridinyl, pyrrolyl, N-alkylpyrrolyl, pyrimidinyl, pyrazinyl, imidazolyl and tetrazolyl. The heteroaromatic ring can be fused to an aryl, heterocyclyl or cycloalkyl ring, wherein the ring connected to the parent structure is the heteroaromatic ring. Heteroaryl may be optionally substituted or unsubstituted, and when it is substituted, the substituent may be one or more of the following groups independently selected from the group consisting of: alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio. Heteroaryl may be substituted or unsubstituted.

In the present application, the term "cycloalkyl" refers to a saturated or partially unsaturated monocyclic or polycyclic hydrocarbon substituent, and the cycloalkyl ring contains 3 to 20 carbon atoms, preferably 3 to 12 carbon atoms, preferably 3 to 10 carbon atoms, preferably 3 to 8 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes spiro cycloalkyl, fused cycloalkyl, and bridged cycloalkyl. Cycloalkyl may be substituted or unsubstituted. When it is substituted, substitution with a substituent may be performed at any available linking site, and the substituent is preferably independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

In the present application, the term "partially unsaturated" generally means that the cyclic structure contains at least one double or triple bond between the ring molecules. The term "partially unsaturated" encompasses cyclic structures having multiple sites of unsaturation, but is not intended to include aromatic or heteroaromatic rings defined herein. The term "unsaturated" means that the moiety has one or more degrees of unsaturation.

In the present application, the term "heterocyclyl" refers to a saturated or partially unsaturated non-aromatic monocyclic or polycyclic hydrocarbon substituent comprising 3 to 20 ring atoms, one or more of which are heteroatoms selected from the group consisting of nitrogen, oxygen, and sulfur, and the remaining ring atoms are carbon atoms. Preferably, heterocyclyl contains 3 to 12 ring atoms, 1 to 4 of which are heteroatoms; more preferably, heterocyclyl contains 3 to 8 ring atoms, 1 to 3 of which are heteroatoms; more preferably, heterocyclyl contains 3 to 6 ring atoms, 1 to 3 of which are heteroatoms; most preferably, heterocyclyl contains 5 or 6 ring atoms, 1 to 3 of which are heteroatoms. Non-limiting examples of monocyclic heterocyclyl include pyrrolidinyl, tetrahydropyranyl, piperidinyl, morpholinyl, thiomorpholinyl, homopiperazinyl, etc. Non-limiting examples of polycyclic heterocyclyl include spiro heterocyclyl, fused heterocyclyl, and bridged heterocyclyl. The heterocyclyl ring may be fused to an aryl, heteroaryl or cycloalkyl ring, and the ring attached to the parent structure is heterocyclyl. Heterocyclyl may be substituted or unsubstituted. When it is substituted, substitution with a substituent may be performed at any available linking site, and the substituent is preferably independently selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

In the present application, the term "ring-forming atom" generally refers to an atom contained in a cyclic structure. For example, a ring-forming atom may be a carbon atom in a benzene ring, or may be a nitrogen atom in a pyridine ring.

When a hydrogen atom is linked to a ring-forming atom, the ring-forming atom may be substituted or unsubstituted.

In the present application, the term "each independently" generally means that a variable applies in any case irrespective of the presence or absence of variables having the same or different definitions in the same compound. For example, the variable may refer to the type or number of substituents in the compound, the type of atoms in the compound, and so on. For example, where R occurs twice in a compound and R is defined as "independently carbon or nitrogen", both R can be carbon, both R can be nitrogen, or one R can be carbon and the other R is nitrogen.

In the present application, the term "optional" or "optionally" generally means that the event or circumstance subsequently described may, but not necessarily, occur, and that the description includes instances where the event or circumstance occurs or does not occur. For example, "heterocyclyl group optionally substituted with alkyl" means that alkyl may be, but not necessarily, present, and that the description may include instances where the heterocyclyl group is or is not substituted with alkyl.

In the present application, the term "substituted" generally means that one or more hydrogen atoms in the group, for example, up to 5 (e.g., 1 to 3) hydrogen atoms, are each independently substituted with a corresponding number of substituents. A substituent is only in its possible chemical position, and those skilled in the art will be able to determine (by experiments or theories) possible or impossible substitution without undue efforts. For example, it may be unstable when amino or hydroxy having a free hydrogen is bound to a carbon atom having an unsaturated (such as olefin) bond.

In the present application, the term "0 or more (e.g., 0 or 1 or more, 0 or 1, or 0) methylene units are replaced" generally means that when the structure comprises one or more methylene units, the one or more methylene units may not be replaced, or may be replaced by one or more groups that are not methylene (e.g., —NHC(O)—, —C(O)NH—, —C(O)—, —OC(O)—, —C(O)O—, —NH—, —O—, —S—, —SO—, —SO$_2$—, —PH—, —P(=O)H—, —NHSO$_2$—, —SO$_2$NH—, —C(=S)—, —C(=NH)—, —N=N—, —C=N—, —N=C— or —C(=N$_2$)—).

In the present application, the "linking" of group X to group Y may generally be in any orientation, which generally means that when group X is used for linker Y and group Z, two or more linking sites of the group X may be linked arbitrarily to either group Y or group Z.

In the present application, the term "compound" generally refers to a substance having two or more different elements. For example, the compound disclosed herein may be an organic compound. For example, the compound disclosed herein may be a compound having a molecular weight of no more than 500 Da, a compound having a molecular weight of no more than 1000 Da, a compound having a molecular weight of no less than 1000 Da, or a compound having a molecular weight of no less than 10,000 Da or no less than 100,000 Da. In the present application, the compound may also refer to a compound that involves linking by a chemical bond, for example, a compound where one or more molecules having a molecular weight of no more than 1000 Da are linked, by a chemical bond, to a biological macromolecule, wherein the biological macromolecule may be polysaccharide, protein, nucleic acid, polypeptide, and the like. For example, the compound disclosed herein may include a compound where a protein is linked to one or more molecules having a molecular weight of no more than 1000 Da, may include a compound where a protein is linked to one or more molecules having a molecular weight of no more than 10,000 Da, and may include a compound where a protein is linked to one or more molecules having a molecular weight of no more than 100,000 Da.

In the present application, the terms such as "alkyl", "alkenyl" and "cycloalkyl" may be preceded by a notation to indicate the number of atoms present in the groups under particular circumstances as in $C_1$-$C_4$ alkyl, $C_3$-$C_7$ cycloalkoxy, and $C_1$-$C_4$ alkylcarbonylamino and the like, as known to those skilled in the art, and the subscript numeral following "C" indicates the number of carbon atoms present in the group. For example, $C_3$ alkyl refers to an alkyl group containing three carbon atoms (e.g., n-propyl, or isopropyl); in $C_{1-10}$, members of the group may contain any number of carbon atoms within the range of 1-10.

One or more hydrogen atoms in the group, for example, up to 5 (e.g., 1 to 3) hydrogen atoms, are each independently substituted with a corresponding number of substituents. A substituent is only in its possible chemical position, and those skilled in the art will be able to determine (by experiments or theories) possible or impossible substitution without undue efforts. For example, it may be unstable when amino or hydroxy having a free hydrogen is bound to a carbon atom having an unsaturated (such as olefin) bond.

In the present application, the compound or ligand-drug conjugate of the present application includes tautomers, mesomers, racemates, enantiomers, and/or diastereoisomers thereof. In the present application, the term "diastereoisomer" generally refers to a stereoisomer that has two or more chiral centers and whose molecules are not mirror images of each other. Diastereoisomers may have different physical properties, e.g., melting points, boiling points, spectral properties, and reactivities. In the present application, the terms "tautomer" or "tautomeric form" are used interchangeably and generally refer to structural isomers of different energies that can be converted into each other by crossing a low energy barrier. For example, proton tautomers (also known as prototropic tautomers) include interconversions by proton migration, such as keto-enol isomerization and imine-enamine isomerization. Valence tautomers include interconversions by recombination of some bonding electrons. In the present application, the term "mesomer" generally means that the molecule contains asymmetric atoms but the total optical rotation is zero due to the presence of symmetric factors. The term "racemate" or "racemic mixture" refers to a composition of two enantiomeric substances in equimolar amounts.

In the present application, the term "isomers" of a compound or a ligand-drug conjugate generally includes tautomers, mesomers, racemates, enantiomers and diastereoisomers of the compound.

In the present application, the term "ligand-drug conjugate" generally means that a ligand is linked to a biologically active cytotoxic drug via a stable linking unit. In the present application, the "ligand-drug conjugate" may be an antibody-drug conjugate (ADC), which may mean that an antibody or an antibody fragment is linked to a biologically active drug (e.g., a cytotoxic drug) via a stable linking unit.

In the present application, the term "ligand" generally refers to a macromolecular compound capable of recognizing and binding to an antigen or receptor associated with a target cell. The role of ligands may be to present the drug to a target cell population to which the ligand binds, and the ligands include, but are not limited to, protein hormones, lectin, growth factors, antibodies, or other molecules capable of binding to a cell, a receptor and/or an antigen. In the present application, the ligand may be denoted as Ab, and a linking bond is formed between the ligand antigen and the linking unit through a heteroatom in the ligand. The ligand may be an antibody or an antigen-binding fragment (Ab) thereof, wherein the antibody may be selected from the group consisting of a chimeric antibody, a humanized antibody, a fully human antibody, and a murine antibody, and the antibody may be a monoclonal antibody.

The term "cytotoxic drug" generally refers to a toxic drug, and the cytotoxic drug may be a chemical molecule within the tumor cell that is strong enough to disrupt its normal growth. Cytotoxic drugs can kill tumor cells at a sufficiently high concentration. The "cytotoxic drug" may include toxins, such as small molecule toxins or enzymatically active toxins of bacterial, fungal, plant or animal origin, radioisotopes (e.g., $At^{211}$, $I^{131}$, $I^{125}$, $Y^{90}$, $Re^{186}$, $Re^{188}$, $Sm^{153}$, $Bi^{212}$, $P^{32}$ or radioactive isotopes of Lu), toxic drugs, chemotherapeutic drugs, antibiotics and nucleolytic enzymes; for example, the cytotoxic drug may be toxic drugs, including but not limited to camptothecin derivatives, which, for example, may be the camptothecin derivative exatecan (chemical name: (1S,9S)-1-amino-9-ethyl-5-fluoro-2,3-dihydro-9-hydroxy -4-methyl-1H,12H-benzo [de] pyrano [3', 4':6,7] imidazo[1,2-b] quinoline-10,13 (9H,15H)-di one).

The term "linker unit" or "linker structure" generally refers to a chemical structural fragment or bond that is linked to a ligand at one end and to a cytotoxic drug at the other end, or that is linked to other linkers before being linked to the cytotoxic drug. The direct or indirect linking of a ligand may mean that the group is directly linked to the ligand via a covalent bond, and may also be linked to the ligand via a linker structure. For example, a chemical structure fragment or bond comprising an acid-labile linker structure (e.g., hydrazone), a protease-sensitive (e.g., peptidase-sensitive) linker structure, a photolabile linker structure, a dimethyl linker structure or a disulfide-containing linker structure may be used as a linker structure.

The term a structure being "optionally linked to other molecular moieties" generally means that the structure is not linked to any other chemical structure, or that the structure is linked (e.g., via a chemical bond or a linker structure) to one or more other chemical structures (e.g., ligands described herein) different from the structure.

The term "drug loading" generally refers to the average amount of cytotoxic drug loaded per ligand and may also be expressed as the ratio of cytotoxic drug to antibody, and the cytotoxic drug loading may range from 0 to 12 (e.g., 1 to 10) cytotoxic drugs per ligand (Ab). In the embodiments of the present application, the drug loading is denoted as DAR, and exemplary values may be an average of 1, 2, 3, 4, 5, 6, 7, 8, 9 and 10. The drug loading per ADC molecule after the coupling reaction can be characterized by conventional methods such as UV/visible spectroscopy, mass spectrometry, ELISA assays and HPLC.

In the present application, certain atoms of the compound of the present application may be present in more than one isotopic form. For example, hydrogen may occur as protium ($^1H$), deuterium ($^2H$), and tritium ($^3H$), and carbon may naturally occur as three different isotopes ($^{12}C$, $^{13}C$, and $^{14}C$). Examples of isotopes that can be incorporated into compound of the present application also include, but are not limited to, $^{15}N$, $^{18}O$, $^{17}O$, $^{18}F$, $^{32}P$, $^{33}P$, $^{129}I$, $^{131}I$, $^{123}I$, $^{124}I$, $^{125}I$, or similar isotopes. Thus, the compounds of the present application may be enriched with one or more of these isotopes relative to the natural abundance of these isotopes. Such isotopically enriched compounds can be used for a variety of purposes, as known to those skilled in the art. For example, substitution with heavy isotopes such as deuterium ($^2H$) may offer certain therapeutic advantages, possibly due to higher metabolic stability. For example, the natural abundance of deuterium ($^2H$) is about 0.015%. Accordingly, one out of about 6500 hydrogen atoms is a deuterium atom. Accordingly, the deuterium abundance of one or more sites (as the case may be) in the deuterium-containing compound of the present application is greater than 0.015%. Unless otherwise indicated, the structures described herein may also include compounds that differ only in the presence or absence of one or more isotopically enriched atoms. For example, compounds having a structure identical to the structure disclosed herein except for the substitution of the hydrogen atom with deuterium or tritium or the substitution of the carbon atom with carbon 13 or carbon 14 are within the scope of the present application.

The term "pharmaceutical composition" generally refers to a mixture containing one or more of the compounds described herein or a physiologically/pharmaceutically acceptable salt or pro-drug thereof, and other chemical components, for example physiologically/pharmaceutically acceptable carriers and excipients. The pharmaceutical composition may promote the administration to an organism, which facilitates the absorption of the active ingredient, thereby exerting biological activities. For preparation of conventional pharmaceutical compositions, reference can be made to *Chinese Pharmacopoeia*. The pharmaceutical composition may be in the form of a sterile injectable aqueous or oily suspension for intramuscular and subcutaneous administration. The suspension can be prepared according to a known technique using suitable dispersing agents or wetting agents and suspending agents. The sterile injectable formulation may also be a sterile injection or suspension prepared in a parenterally acceptable non-toxic diluent or solvent, e.g., a solution prepared in 1,3-butanediol. In addition, a sterile fixed oil may be conventionally used as a solvent or a suspending medium. For example, any blend fixed oil including synthetic mono- or di-glycerides can be used. In addition, fatty acids such as oleic acid may also be used in the preparation of injections.

The term "pharmaceutically acceptable salt" generally refers to a salt of a compound or ligand-drug conjugate disclosed herein, or a salt of a compound described herein. Such salts may be safe and/or effective when used in mammals and may possess the required biological activity, and the antibody-drug conjugate disclosed herein may form a salt with an acid, and non-limiting examples of pharmaceutically acceptable salts include: hydrochloride, hydrobromide, hydriodide, sulphate, bisulfate, citrate, acetate, succinate, ascorbate, oxalate, nitrate, sorbate, hydrophosphate, dihydrophosphate, salicylate, hydrocitrate, tartrate, maleate, fumarate, formate, benzoate, mesylate, ethanesulfonate, benzenesulfonate and p-toluenesulfonate.

The term "pharmaceutically acceptable carrier" generally refers to a carrier or carrier agent that provides therapeutic agents, such as antibodies or polypeptides, genes, and other therapeutic agents. The term refers to any pharmaceutical carrier that does not itself induce the production of antibodies harmful to the individual that receives the composition and can be given without producing undue toxicity. Suitable carriers may be macromolecules that are large and metabolize slowly, such as proteins, polysaccharides, polylactic acids, polyglycolic acids, poly(amino acid)s, amino acid copolymers, lipid aggregates, and inactivated virus particles. Such carriers are well known to those skilled in the art. Pharmaceutically acceptable carriers in therapeutic compositions may include liquids such as water, saline, glycerol, and ethanol. Auxiliary substances, such as wetting or emulsifying agents, or pH buffering substances, may also be present in these carriers.

The terms "treatment" and "treating" generally refer to a method of achieving beneficial or desired effects, including but not limited to therapeutic benefits. Therapeutic benefits include, but are not limited to, eradication, inhibition, reduction, or amelioration of the underlying disease being treated. In addition, therapeutic benefits are achieved by eradicating, inhibiting, reducing, or ameliorating one or more physiological symptoms associated with the underlying disease, and thus improvements are observed in the patient, but the patient may still suffer from the underlying disease.

The term "B7H3-associated disease" refers to any disease or condition that is caused or exacerbated by increased or reduced (generally increased) expression or activity of B7H3 (such as human B7H3), or otherwise associated with B7H3.

The terms "prevention" and "preventing" generally refer to a method of achieving beneficial or desired effects, including but not limited to prophylactic benefits. For the purpose of prophylactic benefits, a pharmaceutical composition can be administered to a patient at risk of developing a particular disease, or to a patient who reports they have one or more physiological symptoms of a disease, even if the disease has not yet been diagnosed.

The term "subject" or "patient" generally refers to a human (i.e., a male or female in any age group, e.g., a pediatric subject (e.g., an infant, a child, or an adolescent) or an adult subject (e.g., a young person, a middle-aged person, or an elderly person)) and/or other primates (e.g., a cynomolgus monkey, or a rhesus monkey); a mammal, including commercially relevant mammals, such as cows, pigs, horses, sheep, goats, cats, and/or dogs; and/or a poultry, including commercially relevant poultries such as chickens, ducks, geese, quail and/or turkeys.

The terms "therapeutically effective amount", "therapeutically effective dose" and "effective amount" refer to an amount of the ligand-drug conjugate of the present invention that is effective in preventing or improving one or more symptoms of a disease or condition or the development of the disease or condition, when administered alone or in combination with other therapeutic agents to a cell, tissue or subject. The therapeutically effective dose also refers to a dose sufficient to cause an improvement in symptoms, e.g., an amount for treating, curing, preventing or improving a related condition or promoting the treatment, cure, prevention or improvement of such condition. When an active ingredient is administered to an individual alone, a therapeutically effective dose only refers to the amount of the ingredient. In the case of administration in combination, a therapeutically effective dose refers to the combined amount of active ingredients that produces a therapeutic effect, regardless of whether these active ingredients are administered in combination, sequentially or simultaneously. An effective amount of a therapeutic agent will result in an increase in a diagnostic index or parameter by at least 10%, generally at least 20%, preferably at least about 30%, more preferably at least 40%, and most preferably at least 50%.

The term "cancer" is used herein to refer to a group of cells that exhibit abnormally high levels of proliferation and growth. Cancer may be benign (also referred to as benign tumor), premalignant or malignant. Cancer cells may be solid cancer cells or hematological cancer cells. The term "tumor" as used herein refers to one or more cells comprising cancer. The term "tumor growth" is used herein to refer to the proliferation or growth of one or more cells comprising cancer, which results in a corresponding increase in the size or extent of the cancer.

Anti-B7H3 Antibody

The present invention provides an antibody that specifically binds to B7H3, for example, an antibody that specifically binds to human B7H3, mouse B7H3, cynomolgus monkey B7H3 and ECD domains thereof. The term "antibody" as used herein is defined above, and includes full-length immunoglobulins and antibody portions thereof that bind to the same antigen. The antibody may be, for example, a monoclonal antibody, a polyclonal antibody, a chimeric antibody, a humanized antibody, or a single-chain antibody. In some embodiments, the antibody portions are Fab fragments or $F(ab')_2$ fragments. In some embodiments, the antibody portions retain the ability to specifically bind to B7H3.

Recombinant anti-B7H3 antibodies, such as chimeric antibodies and humanized monoclonal antibodies, including human and non-human portions, can be prepared using the standard recombinant DNA technique and fall within the scope of the present invention. Such chimeric and humanized monoclonal antibodies can be produced by a recombinant DNA technique, such as the method described in U.S. Pat. No. 7,112,421; Better et al., (1988) *Science,* 240:1041-1043; or Liu et al., (1987) *Proc. Natl. Acad. Sci. USA,* 84:3439-3443. The present invention also includes humanized monoclonal antibodies that are further modified/optimized, for example, by affinity maturation, reverse mutation, and removal of post-translational modification sites.

Preferably, the antibody or the antigen-binding moiety thereof disclosed herein can bind to human 4IgB7H3 with high affinity. The antibodies or antigen-binding portion thereof, as disclosed herein can binds to human 2IgB7H3 with much lower affinity. The antibodies or antigen-binding portion thereof, as disclosed herein can bind to human 4IgB7H3 with high affinity but bind to human 2IgB7H3 with much lower affinity.

The binding of the antibody of the present invention to B7H3 can be assessed using one or more techniques recognized in the art, such as ELISA or flow cytometry. In some embodiments, the antibody can be analyzed and tested by flow cytometry, in which the antibody reacts with a human B7H3-expressing cell line, such as MCF-7 cancer cells or CHOK1 cells that have been transfected to express B7H3 on their cell surfaces. In addition, the antibody can also be tested for binding in a binuclear binding analysis, including binding kinetics (e.g., the KD value). In some other embodiments, the antibody is tested by ELISA, in which the antibody reacts with soluble B7H3 proteins.

The present invention provides an antibody that binds to the human 4IgB7H3 protein with a $K_D$ of $1 \times 10^{-8}$ M or less, a $K_D$ of $1 \times 10^{-9}$ M or less, a $K_D$ of $5 \times 10^{-10}$ M or less, a $K_D$ of $1 \times 10^{-10}$ M or less, a $K_D$ of $9 \times 10^{-11}$ M or less, a $K_D$ of $8 \times 10^{-11}$ M or less, or a $K_D$ of $7 \times 10^{-11}$ M or less, as measured by surface plasmon resonance (SPR). The antibody disclosed herein can also bind to the human 2IgB7H3 protein with a $K_D$ of $5 \times 10^{-9}$ M or higher, a $K_D$ of $1 \times 10^{-8}$ M or higher, a $K_D$ of $2 \times 10^{-8}$ M or higher, a $K_D$ of $3 \times 10^{-8}$ M or higher, or a KD of $4 \times 10^{-8}$ M or higher, as measured by surface plasmon resonance (SPR). In some embodiments, the antibody disclosed herein binds to human 4IgB7H3 with a $K_D$ value that is more than 500 times, more than 100 times, or more than 50 times less than the $K_D$ value for the binding to human 2IgB7H3. These $K_D$ value for comparison may be measured by Surface Plasmon Resonance (SPR).

In some embodiments, the antibody of the present invention is capable of binding to a human or cynomolgus monkey B7H3-expressing cell line with an $EC_{50}$ of less than 5 nM, less than 4 nM, less than 3 nM, or less than 2 nM, as determined by FACS.

In some embodiments, the antibody or the antigen-binding moiety thereof is a chimeric antibody or a murine antibody that specifically binds to B7H3, preferably human 4IgB7H3. In some further embodiments, the antibody or the antigen-binding moiety thereof is a humanized antibody that specifically binds to B7H3, preferably human 4IgB7H3. In some further embodiments, the humanized antibody or the antigen-binding moiety thereof comprises one or more reverse mutations in the framework region. In some further embodiments, the humanized antibody or the antigen-binding moiety thereof comprises one or more modifications at potential post-translational modification (PTM) sites, for example, to remove any amino acid except for NG, NS and DG in the CDRs, NXS and NXT (X can be any amino acid except for P) in the entire length.

In some embodiments, the antibody or the antigen-binding moiety thereof disclosed herein comprises one or more heavy chain CDRs (HCDRs) selected from the group consisting of at least one of the following:
  (i) HCDR1 comprising SEQ ID NO: 1;
  (ii) HCDR2 comprising SEQ ID NO: 2; and
  (iii) HCDR3 comprising SEQ ID NO: 3; and/or
one or more light chain CDRs (LCDRs) selected from the group consisting of at least one of the following:
  (i) LCDR1 comprising SEQ ID NO: 4, 7, or 18;
  (ii) LCDR2 comprising SEQ ID NO: 5; and
  (iii) LCDR3 comprising SEQ ID NO: 6.

In some embodiments, the antibody or the antigen-binding moiety thereof described above may comprise: HCDR1 comprising or consisting of SEQ ID NO: 1, HCDR2 comprising or consisting of SEQ ID NO: 2, HCDR3 comprising or consisting of SEQ ID NO: 3, LCDR1 comprising or consisting of SEQ ID NO: 7, LCDR2 comprising or consisting of SEQ ID NO: 5, and LCDR3 comprising or consisting of SEQ ID NO: 6. Specifically, the antibody may further comprise one or more modifications in the CDRs to remove potential PTM sites. In some embodiments, the antibody comprises one or more modifications in LCDR1 compared to the LCDR1 as shown in SEQ ID NO: 7 ("KSSQSLLNSSNQKNYLA") to remove "NS", which are potential PTM sites in the sequence. In some preferred embodiments, the antibody comprises a substitution at position 8 or 9 of the amino acid sequence of LCDR1 compared to the LCDR1 as shown in SEQ ID NO: 7 ("KSSQSLLNSSNQKNYLA"). In some more preferred embodiments, the antibody comprises an N-to-Q substitution at position 8 of the amino acid sequence of LCDR1 (i.e., SEQ ID NO: 4, "KSSQSLLQSSNQKNYLA"). In some other embodiments, the antibody comprises an S-to-P substitution at position 9 of the amino acid sequence of LCDR1 (i.e., SEQ ID NO: 18, "KSSQSLLNPSNQKNYLA"). A person skilled in the art would appreciate that, other types of substitutions may be selected so long as the binding affinity for B7H3 is substantially retained.

In some embodiments, the antibody or the antigen-binding moiety thereof described above may comprise: HCDR1 comprising or consisting of SEQ ID NO: 1, HCDR2 comprising or consisting of SEQ ID NO: 2, HCDR3 comprising or consisting of SEQ ID NO: 3, LCDR1 comprising or consisting of SEQ ID NO: 4, LCDR2 comprising or consisting of SEQ ID NO: 5, and LCDR3 comprising or consisting of SEQ ID NO: 6.

In some embodiments, the antibody or the antigen-binding moiety thereof comprises a heavy chain variable region (VH) and a light chain variable region (VL), wherein the heavy chain variable region and the light chain variable region comprise HCDR1 through HCDR3 and LCDR1 through LCDR3, respectively, as described above.

In some embodiments, the heavy chain variable region of the antibody or the antigen-binding moiety thereof comprises:
  (i) an amino acid sequence of SEQ ID NO: 8 or 10; (ii) an amino acid sequence that is at least 85%, 90% or 95% identical to SEQ ID NO: 8 or 10; or (iii) an amino acid sequence having one or more (e.g., 1, 2, 3, 4, 5, 6, 7, 8, 9, 10 or more) amino acid additions, deletions and/or substitutions as compared to SEQ ID NO: 8 or 10.

In some embodiments the amino acid substitution(s) may be conservative substitutions.

In some embodiments, the light chain variable region of the antibody or the antigen-binding moiety thereof comprises:
  (i) an amino acid sequence of SEQ ID NO: 9 or 11; (ii) an amino acid sequence that has at least 85%, at least 90% or at least 95% identity to SEQ ID NO: 9 or 11; or (iii) an amino acid sequence having one or more (e.g., 1, 2, 3, 4, 5, 6, 7, 8, 9, 10 or more) amino acid additions, deletions and/or substitutions as compared to SEQ ID NO: 9 or 11.

In some embodiments the amino acid substitution(s) may be conservative substitutions.

In some embodiments, the antibody or the antigen-binding moiety thereof comprises a heavy chain variable region (VH) and a light chain variable region (VL), wherein the VH comprises:
  (i) an amino acid sequence of SEQ ID NO: 8 or 10; or (ii) an amino acid sequence having one or more (e.g., 1, 2, 3, 4, 5 or more) amino acid substitutions in the framework region(s) as compared to SEQ ID NO: 8 or 10; and/or the VL comprises:
  (i) an amino acid sequence of SEQ ID NO: 9 or 11; or (ii) an amino acid sequence having one or more (e.g., 1, 2, 3, 4, 5 or more) amino acid substitutions in the framework region(s) as compared to SEQ ID NO: 9 or 11.

In some embodiments the amino acid substitution(s) may be conservative substitutions.

In some embodiments, the antibody or antigen-binding portion thereof comprises the HCDR1, HCDR2 and HCDR3 of the VH region as shown in SEQ ID No: 8 or 10, and LCDR1, LCDR2 and LCDR3 of the VL region as shown in SEQ ID No: 9 or 11.

As would be understood by those skilled in the art, the exact numbering and placement of CDRs may differ in different numbering systems. However, it should be understood that the disclosure of variable heavy and/or variable light chain sequences includes the disclosure of relevant (intrinsic) CDRs. Thus, the disclosure of each heavy chain variable region is the disclosure of heavy chain CDRs (e.g., HCDR1, HCDR2, and HCDR3), and the disclosure of each light chain variable region is the disclosure of light chain CDRs (e.g., LCDR1, LCDR2, and LCDR3). Amino acids can be assigned to each CDR according to one or a combination of numbering schemes, all of which are well known in the art. A comparison of CDR numbers is shown below, see Lafranc et al., Dev. Comp. Immunol. 27(1): 55-77 (2003):

| CDR | Kabat | IMGT | Chothia | AbM | Kabat + Chothia | Dr. Martin's description (see Martin A, "Antibody bioinformatics website of Dr. Andrew Martin's lab at UCL", last updated on Jul. 31, 2018) |
|---|---|---|---|---|---|---|
| HCDR1 | 31-35 | 27-38 | 26-32 | 26-35 | 26-35 | CXXX + HCDR1 + W |
| HCDR2 | 50-65 | 56-65 | 52-56 | 50-58 | 50-65 | LEWG + HCDR2 |
| HCDR3 | 95-102 | 105-117 | 95-102 | 95-102 | 95-102 | CAR + HCDR3 + WGXG |
| LCDR1 | 24-34 | 27-38 | 24-34 | 24-34 | 24-34 | C + LCDR1 + W |
| LCDR2 | 50-56 | 56-65 | 50-56 | 50-56 | 50-56 | 16 residues after LCDR1 |
| LCDR3 | 89-97 | 105-117 | 89-97 | 89-97 | 89-97 | C + LCDR3 + FGXG |

In some embodiments, the amino acid sequences of the CDRs may have at least 80%, 81%, 82%, 83%, 84%, 85%, 86%, 87%, 88%, 89%, 90%, 91%, 92%, 93%, 94%, 95%, 96%, 97%, 98%, or 99% identity to the sequences described above. In some embodiments, the amino acid sequences of the variable regions may have least 90%, 91%, 92%, 93%, 94%, 95%, 96%, 97%, 98%, or 99% identity to the sequences described above.

As described above, at least one amino acid addition, deletion and/or substitution in the VH or VL region may not be in any CDR sequence, but in framework (FR) sequences. For example, the isolated antibody or antigen-binding moiety thereof may comprise one or more amino acid substitutions in framework sequences, such as FR1, FR2, FR3, and/or FR4 of the VH or VL region. In some embodiments, the framework regions of the VH region comprise one or more of the following substitutions: S025T, V071R, Y091F, V089T.

In some embodiments, changes in the 6 CDRs may include a total of 0, 1, 2, 3, 4, or 5 amino acid modifications (perferably amino acid substitutions) in total, as well as changes in the framework regions of the heavy chain variable region and the light chain variable region, so long as the framework (excluding the CDRs) maintains at least about 80%, 85%, or 90% identity to the parent antibody (e.g. W301088-1.145.16). Thus, the same CDR described herein can be combined with different framework sequences from human germline sequences, so long as the framework regions maintain at least 80%, 85%, or 90% identity to the human germline sequences.

In certain embodiments, the isolated antibody or antigen-binding moiety thereof provided herein comprises any suitable framework region (FR) sequence, so long as the antigen-binding domain can specifically bind to B7H3, preferably human Ig4B7H3.

In some embodiments, one or more amino acid modifications may be introduced into an Fc region of an antibody provided herein, thus producing an Fc region variant. The Fc region variant may comprise a human Fc region sequence (such as the human IgG1, IgG2, IgG3, or IgG4 Fc region) comprising an amino acid modification (such as substitution) at one or more amino acid positions.

In some embodiments, antibodies modified by cysteine engineering may need to be produced, such as "sulfo-MAb", wherein one or more residues of the antibodies are substituted by cysteine residues.

In some embodiments, the antibodies provided herein can be further modified to contain other non-protein moieties known in the art and readily available. Suitable moieties for antibody derivatization include, but are not limited to, water-soluble polymers. Non-limiting examples of water-soluble polymers include, but are not limited to, polyethylene glycol (PEG), ethylene glycol/propylene glycol copolymer, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone)polyethylene glycol, propylene glycol homopolymer, polypropylene oxide/ethylene oxide copolymer, polyoxyethylated polyol (such as glycerol), polyvinyl alcohol, and mixtures thereof.

Any suitable method for producing antibodies may be employed to produce the antibody of the present invention. B7H3 in any suitable form may be used as an immunogen (antigen) for antibody production. By way of example and not limitation, any B7H3 variant or a fragment thereof may be used as an immunogen. In some embodiments, hybridoma cells that produce murine monoclonal anti-human B7H3 antibodies can be produced by methods well known in the art. Antibodies derived from rodents (e.g., mouse) may induce unwanted immunogenicity of the antibodies when used as therapeutic agents in vivo. Repeated use of these antibodies induces an immune response in the human body to therapeutic antibodies. Such immune responses result in at least a loss of therapeutic efficacy and, for severe cases, a potentially lethal allergic reaction. One method for reducing the immunogenicity of rodent antibodies includes producing chimeric antibodies, in which the mouse variable region is fused to the human constant region (Liu et al. (1987), Proc. Natl. Acad. Sci. USA 84:3439-3443). However, the preservation of intact rodent variable region in a chimeric antibody may still induce deleterious immunogenicity in patients. Grafting of the complementarity determining region (CDR) loops of the rodent variable domain onto the human framework (i.e., humanization) has been used to further minimize rodent sequences (Jones et al., (1986) Nature 321:522; Verhoeyen et al., (1988) Science 239:1534).

In some embodiments, the chimeric or humanized antibodies of the present invention can be prepared based on the sequences of the prepared murine monoclonal hybridoma antibodies. DNA encoding the immunoglobulin heavy and light chains can be obtained from a murine hybridoma of interest and engineered to comprise non-murine (e.g., human) immunoglobulin sequences using standard molecular biology techniques.

In some embodiments, the chimeric B7H3 antibodies described herein can be prepared by obtaining the chimeric heavy chains and the chimeric light chains by operably linking the immunoglobulin heavy chain and light chain variable regions of hybridoma origin to human IgG constant regions respectively using methods known in the art (see, e.g., U.S. Pat. No. 4,816,567 to Cabilly et al.). In some embodiments, the chimeric antibodies of the present invention comprise constant regions which can be selected from any human IgG subtype, such as IgG1, IgG2, IgG3 and IgG4, preferably IgG1.

In some embodiments, the chimeric B7H3 antibodies of the present invention can be obtained by "mixing and matching" a chimeric light chain expression plasmid with a chimeric heavy chain expression plasmid to transfect expression cells. The binding of such "mixed and matched" antibodies to B7H3 can be tested using the binding assays described above and other conventional binding assays (e.g., ELISA).

For the humanized antibodies described herein, murine CDR regions can be inserted into human germline framework regions using methods known in the art. See U.S. Pat. No. 5,225,539 to Winter et al. and U.S. Pat. Nos. 5,530,101; 5,585,089; 5,693,762 and 6,180,370 to Queen et al.

In some embodiments, the CDR sequences of the antibody used in the drug conjugate, composition, use or method of the present invention comprise the CDR sequences of the antibody W301088-1.145.16-z3-p1-uIgG1KV320 (WBP301088 for short). In some embodiments, the CDR sequences of the antibody used in the drug conjugate, composition, use or method of the present invention comprise the CDR sequences of the antibody W301088-1.145.16-xIgG1KV320. In some embodiments, the variable region sequences of the antibody used in the drug conjugate, composition or use of the present invention comprise the variable region sequences from the antibody W301088-1.145.16-z3-p1-uIgG1KV320 or W301088-1.145.16-xIgG1KV320. In some embodiments, the amino acid sequences of the antibody used in the drug conjugate, composition, use or method of the present invention comprise the full-length amino acid sequences from the antibody W301088-1.145.16-z3-p1-uIgG1KV320 or W301088-1.145.16-xIgG1KV320.

The anti-B7H3 antibody W301088-1.145.16-xIgG1KV320 or the antigen-binding fragment thereof described herein is prepared as described in the examples. In some embodiments, the CDR sequences of the antibody used in the drug conjugate, composition, use or method of the present invention comprise HCDR1, HCDR2 and HCDR3 comprising amino acid sequences as set forth in SEQ ID NO: 1, SEQ ID NO: 2 and SEQ ID NO: 3, respectively, and LCDR1, LCDR2 and LCDR3 comprising amino acid sequences as set forth in SEQ ID NO: 7, SEQ ID NO: 5 and SEQ ID NO: 6, respectively. In some embodiments, the variable region sequences of the antibody used in the drug conjugate, composition or use of the present invention comprise a heavy chain variable region comprising an amino acid sequence as set forth in SEQ ID NO: 8 and a light chain variable region comprising an amino acid sequence as set forth in SEQ ID NO: 9. In some embodiments, the antibody used in the drug conjugate, composition, use or method of the present invention comprises a heavy chain comprising an amino acid sequence as set forth in SEQ ID NO: 14 and a light chain comprising an amino acid sequence as set forth in SEQ ID NO: 15.

The anti-B7H3 antibody W301088-1.145.16-z3-p1-uIgG1KV320 (WBP301088 for short) or the antigen-binding fragment thereof described herein is prepared as described in the examples. In some embodiments, the CDR sequences of the antibody used in the drug conjugate, composition, use or method of the present invention comprise HCDR1, HCDR2 and HCDR3 comprising amino acid sequences as set forth in SEQ ID NO: 1, SEQ ID NO: 2 and SEQ ID NO: 3, respectively, and LCDR1, LCDR2 and LCDR3 comprising amino acid sequences as set forth in SEQ ID NO: 4, SEQ ID NO: 5 and SEQ ID NO: 6, respectively. In some embodiments, the variable region sequences of the antibody used in the drug conjugate, composition or use of the present invention comprises a heavy chain variable region comprising an amino acid sequence as set forth in SEQ ID NO: 10 and a light chain variable region comprising an amino acid sequence as set forth in SEQ ID NO: 11. In some embodiments, the antibody used in the drug conjugate, composition, use or method of the present invention comprises a heavy chain comprising an amino acid sequence as set forth in SEQ ID NO: 12 and a light chain comprising an amino acid sequence as set forth in SEQ ID NO: 13.

The amino acid sequences of the chimeric antibody W301088-1.145.16-xIgG1KV320 and the humanized antibody W301088-1.145.16-z3-p1-uIgG1KV320 of the present invention are shown below. In some embodiments, the CDRs of the antibody of the present invention are numbered using a Kabat+Chothia combination numbering scheme.

```
Amino acid sequence of W301088-1.145.16-
xIgG1KV320 (the underlined parts are CDRs)
Heavy chain variable region VH
                                      SEQ ID NO: 8
DVQLQESGPGLVKPSQSLSLTCTVTDYSITGDYAWNWIRQFPGNKLE

WMGYISYSGSTSYNPLSQSRISITRDTSKNQFFLQLNSVTSEDTATY

FCARSLGRRWYFVVWGAGTTVTVSA

HCDR1:
                                      (SEQ ID NO: 1)
DYSITGDYAWN

HCDR2:
                                      (SEQ ID NO: 2)
YISYSGSTSYNPSLQS

HCDR3:
                                      (SEQ ID NO: 3)
SLGRRWYFVV

Light chain variable region VL
                                      SEQ ID NO: 9
DIVMTQSPSSLAMSVGQKVTMSCKSSQSLLNSSNQKNYLAWYQQKPG

QSPKLLIYFASTRESGVPDRFIGSGSGTDFTLTISSVQAEDLTDYFC

QQHYSAPWTFGGGTKLEIK

LCDR1:
                                      (SEQ ID NO: 7)
KSSQSLLNSSNQKNYLA

LCDR2:
                                      (SEQ ID NO: 5)
FASTRES

LCDR3:
                                      (SEQ ID NO: 6)
QQHYSAPWT

Heavy chain
                                      SEQ ID NO: 14
DVQLQESGPGLVKPSQSLSLTCTVTDYSITGDYAWNWIRQFPGNKLE

WMGYISYSGSTSYNPLSQSRISITRDTSKNQFFLQLNSVTSEDTATY

FCARSLGRRWYFVVWGAGTTVTVSAASTKGPSVFPLAPSSKSTSGGT

AALGCLVKDYFPEPVTVSWNSGALTSGVHTFPAVLQSSGLYSLSSVV

TVPSSSLGTQTYICNVNHKPSNTKVDKRVEPKSCDKTHTCPPCPAPE

AAGGPSVFLFPPKPKDTLMISRTPEVTCVVVDVSHEDPEVKFNWYVD
```

```
-continued
GVEVHNAKTKPREEQYNSTYRVVSVLTVLHQDWLNGKEYKCKVSNKA

LPAPIEKTISKAKGQPREPQVYTLPPSREEMTKNQVSLTCLVKGFYP

SDIAVEWESNGQPENNYKTTPPVLDSDGSFFLYSKLTVDKSRWQQGN

VFSCSVMHEALHNHYTQKSLSLSPG

Light chain
                                         SEQ ID NO: 15
DIVMTQSPSSLAMSVGQKVTMSCKSSQSLLNSSNQKNYLAWYQQKPG

QSPKLLIYFASTRESGVPDRFIGSGSGTDFTLTISSVQAEDLTDYFC

QQHYSAPWTFGGGTKLEIKRTVAAPSVFIFPPSDEQLKSGTASVVCL

LNNFYPREAKVQWKVDNALQSGNSQESVTEQDSKDSTYSLSSTLTLS

KADYEKHKVY ACEVTHQGLSSPVTKSFNRGEC

Amino acid sequence of W301088-1.145.16-z3-pl-
ulgG1KV320 (the underlined parts are CDRs)
Heavy chain variable region VH
                                         SEQ ID NO: 10
QVQLQESGPGLVKPSQTLSLTCTVTDYSITGDYAWNWIRQHPGKGLE

WIGYISYSGSTSYNPSLQSRVTISRDTSKNQFSLKLSSVTAADTAVY

FCARSLGRRWYFVVWGQGTTVTVSS

HCDR1:
                                         (SEQ ID NO: 1)
DYSITGDYAWN

HCDR2:
                                         (SEQ ID NO: 2)
YISYSGSTSYNPSLQS

HCDR3:
                                         (SEQ ID NO: 3)
SLGRRWYFVV

Light chain variable region VL
                                         SEQ ID NO: 11
DIVMTQSPDSLAVSLGERATINCKSSQSLLQSSNQKNYLAWYQQKPG

QPPKLLIYFASTRESGVPDRFSGSGSGTDFTLTISSLQAEDVAVYYC

QQHYSAPWTFGGGTKVEIK

LCDR1:
                                         (SEQ ID NO: 4)
KSSQSLLQSSNQKNYLA

LCDR2:
                                         (SEQ ID NO: 5)
FASTRES

LCDR3:
                                         (SEQ ID NO: 6)
QQHYSAPWT

Heavy chain
                                         SEQ ID NO: 12
QVQLQESGPGLVKPSQTLSLTCTVTDYSITGDYAWNWIRQHPGKGLE

WIGYISYSGSTSYNPSLQSRVTISRDTSKNQFSLKLSSVTAADTAVY

FCARSLGRRWYFVVWGQGTTVTVSSASTKGPSVFPLAPSSKSTSGGT

AALGCLVKDYFPEPVTVSWNSGALTSGVHTFPAVLQSSGLYSLSSVV

TVPSSSLGTQTYICNVNHKPSNTKVDKRVEPKSCDKTHTCPPCPAPE

AAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKA

-continued
LPAPIEKTISKAKGQPREPQVYTLPPSREEMTKNQVSLTCLVKGFYP

SDIAVEWESNGQPENNYKTTPPVLDSDGSFFLYSKLTVDKSRWQQGN

VFSCSVMHEALHNHYTQKSLSLSPGK

Light chain
                                         SEQ ID NO: 13
DIVMTQSPDSLAVSLGERATINCKSSQSLLQSSNQKNYLAWYQQKPG

QPPKLLIYFASTRESGVPDRFSGSGSGTDFTLTISSLQAEDVAVYYC

QQHYSAPWTFGGGTKVEIKRTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC
```

The antibody or the antigen-binding moiety thereof disclosed herein has particular functional characteristics or properties. In some embodiments, the antibody (including chimeric and humanized antibodies) has one or more of the following properties:

(a) specifically binding to human 4IgB7H3-expressing cells with high affinity (e.g., less than 2 nM as measured by FACS);
(b) having binding affinity for human 2IgB7H3 that is significantly lower than that for human 4IgB7H3, there being significant differences between the affinities of antibodies that bind to 2IgB7H3 and 4IgB7H3;
(c) specifically binding to cyno B7H3 with high affinity (e.g., less than 5 nM as measured by FACS) that is better than that of a benchmark antibody; and
(d) showing good internalization by B7H3-expressing cancer cells.

Pharmaceutical Composition and Pharmaceutical Formulation

In yet another aspect, the present invention provides a pharmaceutical composition, which comprises the antibody-drug conjugate described herein, a pharmaceutically acceptable salt thereof, and a pharmaceutically acceptable carrier or excipient.

It should be understood that the antibody-drug conjugate, the pharmaceutically acceptable salt thereof or the pharmaceutical composition thereof provided herein can be integrated into a suitable carrier, an excipient and other reagents in a formulation for administration in combination, thus providing improved transfer, delivery, tolerance, etc.

The term "pharmaceutical composition" refers to a formulation which allows the active ingredients contained therein to be present in an effective biologically active form and does not contain additional ingredients having toxicity unacceptable to a subject to which the formulation is administered.

The pharmaceutical formulation comprising the anti-B7H3 antibody described herein, preferably in the form of an aqueous solution or a lyophilized formulation, may be prepared by mixing the anti-B7H3 antibody-drug conjugate or the pharmaceutically acceptable salt thereof of the present invention having the desired purity with one or more optional pharmaceutical adjuvants (*Remington's Pharmaceutical Sciences,* 16th edition, Osol, A. Ed. (1980)).

The pharmaceutical composition or formulation of the present invention can further comprise one or more additional active ingredients which are required for a specific indication being treated, preferably active ingredients having complementary activities that do not adversely affect one another. In some embodiments, the additional active ingredients are chemotherapeutic agents, immune checkpoint inhibitors, cell growth inhibitors, antibiotics or various known anti-tumor or anti-cancer agents, which are suitably present in combination in amounts that are effective for purpose intended. In some embodiments, the pharmaceutical composition of the present invention also comprises a composition of a polynucleotide encoding the anti-B7H3 antibody.

In yet another aspect, the present invention provides a pharmaceutical combination, which comprises the antibody-drug conjugate or the pharmaceutically acceptable salt thereof described herein, or the pharmaceutical composition described herein, and one or more additional therapeutic agents.

In yet another aspect, the present invention provides a kit, which comprises the antibody-drug conjugate or the pharmaceutically acceptable salt thereof described herein, or the pharmaceutical composition described herein, and preferably further comprises a drug delivery device.

Medical Use

In yet another aspect, the present invention provides use of the antibody-drug conjugate, the pharmaceutically acceptable salt thereof described herein or the pharmaceutical composition described herein in preparing a medicament for treating and/or preventing a B7H3-mediated disease or condition, wherein preferably, the disease or condition is cancer.

In yet another aspect, the present invention provides the antibody-drug conjugate, the pharmaceutically acceptable salt thereof described herein or the pharmaceutical composition described herein for use in treating and/or preventing a B7H3-mediated disease or condition, wherein preferably, the disease or condition is cancer.

In yet another aspect, the present invention provides a method for treating and/or preventing a B7H3-mediated disease or condition, which comprises administering to a subject in need the antibody-drug conjugate or the pharmaceutically acceptable salt thereof described herein or the pharmaceutical composition described herein, wherein preferably, the disease or condition is cancer.

In yet another aspect, the present invention provides the antibody-drug conjugate, or the pharmaceutically acceptable salt or the pharmaceutical composition thereof described herein for treating and/or preventing a B7H3-mediated disease or condition, wherein preferably, the disease or condition is cancer.

In some embodiments, the cancer of the present invention is selected from the group consisting of breast cancer, neurological tumors, melanoma, lung cancer, head and neck cancer, colorectal cancer, pancreatic cancer, gastric cancer, renal cancer, bladder cancer, prostate cancer, ovarian cancer, cervical cancer, glioblastoma, esophageal cancer, renal cell carcinoma, endometrial cancer, skin cancer, testicular cancer, thyroid cancer, urothelial cancer, lymphoma (such as non-Hodgkin lymphoma), chronic lymphocytic leukemia, diffuse large B-cell lymphoma, and multiple myeloma.

In yet another aspect, the present invention provides a pharmaceutical combination, which comprises the antibody-drug conjugate or the pharmaceutically acceptable salt thereof described herein, or the pharmaceutical composition described herein, and one or more additional therapeutic agents.

In yet another aspect, the present invention provides a kit, which comprises the antibody-drug conjugate described herein or the pharmaceutical composition described herein.

In some embodiments, routes of administration for the present invention include, but are not limited to, oral administration, intravenous administration, subcutaneous administration, intramuscular administration, intra-arterial administration, intra-articular administration (e.g., in arthritic joints), inhalation, aerosol delivery, intratumoral administration, etc.

In some embodiments, the present invention provides co-administration of an effective amount of one or more therapies (e.g., treatment modalities and/or other therapeutic agents) to a subject. In some embodiments, the therapies include surgical treatment and/or radiation therapy.

In some embodiments, the method or use provided herein further comprises administering to the individual one or more therapies (e.g., treatment modalities and/or other therapeutic agents). The antibody-drug conjugate or the pharmaceutically acceptable salts thereof of the present invention may be administered alone or in combination with other therapeutic agents in a therapy. For example, the antibody may be co-administered with at least one additional therapeutic agent.

The antibody-drug conjugate described in the present application may have inhibitory activity against in vitro proliferation of tumor cells. The inhibitory activity may be that: adding the drug conjugate of the present application to a medium with tumor cells leads to a decrease of 1% or more, 2% or more, 4% or more, 5% or more, 8% or more, 10% or more, 15% or more, 18% or more, 20% or more, 25% or more, 40% or more, 50% or more, 60% or more, 70% or more, 80% or more, 90% or more, or 95% or more, in the proliferation capacity of the tumor cells, compared with adding a negative control or a reference drug. For example, the inhibitory activity may be an IC50 value (nM) for tumor cells of 10000 nM or less, 5000 nM or less, 4000 nM or less, 3000 nM or less, 2000 nM or less, 1000 nM or less, 500 nM or less, 400 nM or less, 300 nM or less, 200 nM or less, 150 nM or less, 120 nM or less, 110 nM or less, 100 nM or less, 99 nM or less, 98 nM or less, 97 nM or less, 95 nM or less, 90 nM or less, 80 nM or less, 75 nM or less, 70 nM or less, 65 nM or less, 62 nM or less, 60 nM or less, 50 nM or less, 40 nM or less, 30 nM or less, 25 nM or less, 23 nM or less, 22 nM or less, 20 nM or less, 19 nM or less, 18 nM or less, 18.5 nM or less, 17 nM or less, 15 nM or less, 12 nM or less, 10 nM or less, 9 nM or less, 8.5 nM or less, 7 nM or less, 6.7 nM or less, 6 nM or less, 5.9 nM or less, 5.5 nM or less, 5.0 nM or less, 4.8 nM or less, 4.5 nM or less, 4.4 nM or less, 4 nM or less, 3.5 nM or less, 3 nM or less, 2.5 nM or less, 2 nM or less, 1.5 nM or less, 1.0 nM or less, 0.5 nM or less, 0.3 nM or less, 0.29 nM or less, 0.25 nM or less, 0.21 nM or less, 0.20 nM or less, 0.18 nM or less, 0.17 nM or less, 0.15 nM or less, 0.12 nM or less, 0.10 nM or less, 0.09 nM or less, 0.08 nM or less, 0.07 nM or less, 0.06 nM or less, 0.05 nM or less, 0.04 nM or less, 0.03 nM or less, 0.02 nM or less, or 0.01 nM or less. For example, the tumor cells may include, but are not limited to, solid tumor cells. For example, the tumor cells may include, but are not limited to, lung cancer cells. For example, the tumor cells may include, but are not limited to, Calu-6 lung cancer cells.

The antibody-drug conjugate described herein may have an in vivo anti-tumor effect. The anti-tumor effect may be that: administering the antibody-drug conjugate of the present application to an animal leads to a decrease of 1% or more, 2% or more, 4% or more, 5% or more, 8% or more, 10% or more, 15% or more, 18% or more, 20% or more, 25% or more, 40% or more, 50% or more, 55% or more, 60% or more, 70% or more, 73% or more, 75% or more, 80% or more, 90% or more, or 95% or more, or a 1.1-fold or more decrease, a 1.3-fold or more decrease, a 1.5-fold or more decrease, a 2-fold or more decrease, a 3-fold or more decrease, a 5-fold or more decrease, a 10-fold or more decrease, a 20-fold or more decrease, a 22-fold or more decrease, a 30-fold or more decrease, a 50-fold or more decrease, a 100-fold or more decrease, a 500-fold or more decrease, a 1000-fold or more decrease, or a 1500-fold or more decrease, in the volume of the tumor in the animal after 1 day, 3 days, 5 days, 7 days, 14 days, 20 days, 21 days or 30 days, compared with administering a negative control or a reference drug. The animal may include, but is not limited to, a mammal. For example, the animal may include, but is not limited to, a cat, a dog, a horse, a pig, a cow, a sheep, a rabbit, a mouse, a rat, a monkey or a human. The administration may include, but is not limited to, oral administration, intravenous injection, intravenous drip, intraperitoneal injection or topical administration. For example, the tumor cells may include, but are not limited to, solid tumor cells. For example, the tumor cells may include, but are not limited to, lung cancer cells, melanoma cells, brain cancer cells, and prostate cancer cells. For example, the tumor cells may include, but are not limited to, Calu-6 lung cancer cells, A375 melanoma cells, U87 brain cancer cells, and PC-3 prostate cancer cells.

The present invention includes any combinations of the specific embodiments described. Further embodiments of the present invention and the full scope of applicability will become apparent from the detailed description provided below. However, it should be understood that the detailed description and the specific examples, while indicating preferred embodiments of the present invention, are provided by way of illustration only, as various changes and modifications within the spirit and scope of the present invention will become apparent to those skilled in the art from the detailed description. All publications, patents and patent applications cited herein, including the citations, are hereby incorporated by reference in their entirety for all purposes.

EXAMPLES

The following examples are provided to demonstrate and further illustrate some preferred embodiments and aspects of the present invention and should not be construed as limiting the scope of the present invention.

Materials and Methods

TABLE 1

| Information on commercially available materials | | |
|---|---|---|
| Material | Supplier | Cat. No. |
| MCF7 cells | ATCC | HTB-22 |
| CHOK1 cells | ATCC | CTL-61 |
| Expi293 ™ expression system kit | Invitrogen | A14635 |
| Expi293F ™ expression medium | Invitrogen | A1435101 |
| Flp-In ™-CHO cell line | Invitrogen | R75807 |
| TMB single solution | Invitrogen | 002023 |
| Lipofectamine ™ 2000 transfection reagent | Invitrogen | 11668027 |
| FreeStyle ™ CHO expression medium | Gibco | 12651014 |
| Hoechst 33342 | Invitrogen | H3570 |
| Calcein AM | Invitrogen | C3099 |
| pHrodo iFL Red STP | Invitrogen | P36011 |
| NuPAGE4%-12% Bis-Tris gel | Invitrogen | NP0322BOX |
| 10 × PBS | Invitrogen | AM9624 |
| RPMI medium 1640 (1×) | Gibco | 22400089 |
| 0.25% trypsin-EDTA (1×) | Gibco | 25200072 |
| FBS | ExCell Bio | FND500 |
| 4% PFA | DING GUO | AR-0211 |
| BSA | BOVOGEN | BSAS 1.0 |
| DPBS | CORNING | 21-031-CVC |
| Ni column | Cytiva | 173712 |
| Protein A column | Cytiva | 175438 |
| TSKgel G3000SWXL column | Tosoh | 0008541 |
| Goat anti-human IgG-Fc-HRP | Bethyl | A80-304P |
| Goat anti-mouse IgG-Fc-HRP | Bethyl | A90-231P |
| Goat anti-mouse IgG1 | Bethyl | A90-205A |
| Goat anti-mouse IgG2a | Bethyl | A90-207A |
| Goat anti-mouse IgG2b | Bethyl | A90-209A |
| Goat anti-mouse IgG3 | Bethyl | A90-211A |
| Goat anti-mouse IgG-Fc Alexa 647 | Jackson ImmunoResearch | 115-605-164 |
| Alexa 647 goat anti-human antibody | Jackson ImmunoResearch | 109-605-098 |
| Goat anti-mouse IgG Fc PE | Jackson ImmunoResearch | 115-115-164 |
| Goat anti-human IgG Fc PE | Jackson ImmunoResearch | 109-115-098 |
| Anti-human Fc IgG | Jackson ImmunoResearch | 109-005-098 |
| Anti-mouse Fc IgG | SouthernBiotech | 1013-01 |
| Goat anti-mouse κ light chain HRP | Southern Biotech | A90-119P |
| Goat anti-mouse λ light chain HRP | Southern Biotech | A90-121P |
| F(ab')2 goat anti-human IgG-Fc | Jackson ImmunoResearch | 109-006-098 |
| F(ab')2-goat anti-mouse IgG-Fc | Jackson ImmunoResearch | 115-005-064 |
| Human B7-H3/CD276 protein, His tag (2IgB7H3) | ACROBiosystems | B73-H52E2 |

TABLE 1-continued

Information on commercially available materials

| Material | Supplier | Cat. No. |
|---|---|---|
| Cynomolgus monkey B7-H3/CD276 protein, His tag | ACROBiosystems | B73-C52Ha |
| Series S sensor chip CM5 | Cytiva | 29-1496-03 |
| Amine coupling kit | Cytiva | BR100050 |
| 10 × HBS-EP+ | Cytiva | BR100669 |

Sample Testing Method

1. ADC DAR Value Analysis Method—HIC-HPLC (Hydrophobic Interaction Chromatography)
  High performance liquid chromatograph: Waters e2965 high performance liquid chromatography system.
  Chromatography column: MabPac™ HIC-Butyl 5 μm 4.6×100 mm (manufacturer: Thermo).
  Mobile phase A: 1.5 M $(NH_4)_2SO_4$+50 mM $K_2HPO_4$ (pH 7.0).
  Mobile phase B: 50 mM $K_2HPO_4$ (pH 7.0)/isopropanol (75:25 V/V).
  Elution was carried out according to the following elution procedure.

| Time | Mobile phase B |
|---|---|
| 0-2 min | 0%-10% |
| 2-22 min | 10%-65% |
| 22-24 min | 65%-100% |
| 24-26 min | 100%-0% |
| 26-30 min | 0% |

Detection conditions: the flow rate of the mobile phase is set at 1 mL/min, the detection wavelength at 280 nm, and the column temperature at 30° C.

2. SEC Purity Analysis—SEC-HPLC (Size Exclusion Chromatography)
  High performance liquid chromatograph: 1260 Agilent liquid chromatograph.
  Chromatography column: Waters Xbridge BEH200 SEC (7.8×300 mm, 3.5 μm)
  Mobile phase: 50 mM $NaH_2PO_4$+200 mM arginine (pH 6.80)+10% isopropanol

| Time | Mobile phase |
|---|---|
| 0-30 min | 100% |

Detection conditions: the flow rate of the mobile phase is set at 0.5 mL/min, the detection wavelength at 280 nm, and the column temperature at 30° C.

Example 1. Generation and Characterization of Anti-B7H3 Antibodies 1.1. Preparation of Antigen, Benchmark Antibody and Cell Line
1.1.1. Generation of Antigen
  The nucleotide sequence encoding the amino acid sequence of the extracellular domain of human 4IgB7H3 (Uniprot ID: Q5ZPR3, amino acids 29-461) was first codon optimized for mammalian expression and then synthesized by Sangon Biotech (Shanghai, China). The DNA segments were subcloned into a pcDNA3.3 expression vector with 6×His at the C-terminal, which was then transfected into Expi293F cells (Invitrogen, A14635). After five days of incubation, the supernatant was purified using a Ni column (Cytiva, 173712). The eluted protein was dialyzed into PBS via a dialysis bag (Spectrum-888-10987, MWCO 3.5 kDa). Protein concentration was determined by absorbance at 280 nm on a NanoDrop device. 2 μg of the purified protein was electrophoresed on SDS-PAGE gel (Invitrogen) with and without a reducing agent. The purity of the purified protein was quantified by HPLC-SEC using a TSKgel G3000SWXL size exclusion chromatography column (Tosoh, 008541). The purified protein was stored at −80° C. Human 2IgB7H3 was purchased from ACRO (Cat. No. B73-H52E2), and cynomolgus monkey B7H3 was purchased from ACRO (Cat. No. B73-C52Ha).

1.1.2. Generation of Benchmark Antibody
  Anti-B7H3 antibody enoblituzumab (MacroGenics, whose light and heavy chain amino acid sequences are SEQ ID NOs: 117 and 119 in U.S. 20120294796A1, respectively) was used as a benchmark antibody. The nucleic acid sequences encoding the variable domains of the antibody were first codon optimized for mammalian expression and then synthesized by Sangon Biotech (Shanghai, China). The DNA segments were then subcloned into a modified pcDNA3.4 expression vector with the constant region of human IgG1. Plasmids containing VH and VL genes were co-transfected into Expi293F cells (Invitrogen, A14635). After five days of incubation, the supernatant was purified using a protein A column (Cytiva, 175438). The eluted protein was dialyzed into PBS via a dialysis bag (Spectrum, 888-10987). Protein concentration was determined by absorbance at 280 nm on a NanoDrop device. 2 μg of the purified protein was electrophoresed on SDS-PAGE gel (Invitrogen) with and without a reducing agent. The purity of the purified protein was quantified by HPLC-SEC using a TSKgel G3000SWXL size exclusion chromatography column (Tosoh, 008541). The purified antibody was stored at −80° C.

1.1.3. Establishment of Stable Cell Line/Cell Pool
  A cell line expressing human 4IgB7H3 was generated. Briefly, CHOK1 cells were transfected with a pcDNA3.3 expression vector containing full-length 4IgB7H3 using Lipofectamine 2000 transfection kit (Invitrogen, 11668027) according to the manufacturer's protocol. At 48 h post-transfection, the cells were subcultured into a selective medium (F12-K containing 10% FBS and 15 μg/mL blasticidin) in a T75 flask. After two or three passages of selection, a cell line stably expressing human 4IgB7H3 (W3XX088-CHOK1.hPro1.2A5) was obtained by blasticidin selection and limiting dilution, and the expression level was determined by FACS using an anti-B7H3 antibody.
  A cell pool expressing cynomolgus monkey B7H3 was generated. Briefly, FlipinCHO cells were transfected with a pcDNA5/pOG44 expression vector containing full-length cynomolgus monkey B7H3 using Lipofectamine 2000 transfection kit (Invitrogen, 11668027) according to the manufacturer's protocol. At 48 h post-transfection, the cells were subcultured into a selective medium (F12 containing 10% FBS and 600 µg/mL hygromycin B) in a T75 flask. After two or three passages of selection, a cell pool stably and highly expressing cynomolgus monkey B7H3 (WBP3XX088-FlpinCHO.cPro1.pool) was obtained by hygromycin B selection and BD FACSMelody™ cell sorting.

1.2. Generation of Antibodies 1.2.1. Animal Immunization

Four 6- to 8-week-old Balb/c mice were immunized with the DNA plasmids encoding human full-length 4IgB7H3 in Example 1.1.3 at 200-400 µg per mouse. The adjuvant mixture includes Adju-Phos, CpG-ODN and GM-CSF. The animals were subjected to subcutaneous injection, intramuscular injection and hydrodynamic tail vein injection once every other week. Blood was collected from the mice after the third injection (the 1st blood collection) and after the fifth injection (the 2nd blood collection). The serum titer was measured by ELISA and FACS.

ELISA assay was used to measure the serum antibody titer against the 4IgB7H3 antigen. A Plate (Nunc) was coated with 100 µL of His tag at 0.5 µg/mL at 4° C. overnight, and then blocked with a blocking buffer (2% BSA in PBS) at ambient temperature for 1 h. The plate was then washed and incubated with 1 µg/mL antigen at ambient temperature for 1 h. After washing, mouse serum was 1:3 serially diluted starting at 1:100 dilution in a blocking buffer, added to the culture plate, and incubated at ambient temperature for 2 h. The plate was then washed, followed by incubation with a secondary antibody, i.e., goat anti-mouse IgG-Fc-HRP (Bethyl, A90-231P), for 1 h. After washing, TMB substrate was added and the interaction was stopped with 2M HCl. The absorbance at 450 nm was read using a microplate reader (Molecular Device). Serum titer was determined at 2-fold background.

TABLE 2

Serum titer test on mouse serum binding to human 4IgB7H3 by ELISA

| Antibody titer | Mouse #1 | Mouse #2 | Mouse #3 | Mouse #4 |
|---|---|---|---|---|
| Serum from the 2nd blood collection | 218700 | 1968300 | 656100 | 1968300 |
| Serum from the 1st blood collection | 218700 | 218700 | 656100 | 218700 |
| Serum before blood collection | <100 | <100 | <100 | <100 |

FACS assay was used to measure the serum antibody titer against the 4IgB7H3 antigen. Briefly, the engineered B7H3-expressing cells in Example 1.1.3 were seeded into a 96-well U-bottom plate at a density of $1\times10^5$ cells/well and centrifuged at 1500 rpm for 4 min at 4° C. The supernatant was then removed. The mouse serum was 1:3 serially diluted starting at 1:100 dilution in 1×PBS/1% BSA to resuspend the cells and incubated for 1 h at 4° C. The cells were washed twice with 180 µL of 1×PBS/1% BSA. The secondary antibody goat anti-mouse IgG-Fc Alexa 647 (Jackson, 109-605-098) was added to the resuspended cells and incubated at 4° C. in the dark for 30 min, followed by washing with 180 µL of 1×PBS/1% BSA. Finally, the cells were resuspended in 100 µL of 1×PBS/1% BSA, and the fluorescence intensity was measured by FACS (BD Canto II) and analyzed by FlowJo version software. Serum titer was determined at 2-fold background.

TABLE 3

Serum titer test on binding of cell line expressing human 4IgB7H3 by FACS

| Antibody titer | Mouse #1 | Mouse #2 | Mouse #3 | Mouse #4 |
|---|---|---|---|---|
| Serum from the 2nd blood collection | 218700 | 1968300 | 1968300 | Close to 1968300 |

When the serum titer was sufficiently high, a final boost immunization with 400 µg of the DNA plasmids encoding human full-length 4IgB7H3 in Example 1.1.3 via hydrodynamic tail vein and $4\times10^6$ MCF-7 cells via foot pad and subcutaneously was performed prior to fusion with myeloma cells. Lymph nodes and spleens were collected for cell fusion.

1.2.2. Hybridoma Generation

The lymph nodes and spleens from the immunized mice in Example 1.2.1 were homogenized and filtered to remove blood clots and cell debris. Sp2/0 myeloma cells in logarithmic growth were collected and centrifuged. B cells obtained by the homogenization of the lymph nodes and spleens from the immunized mice were fused with the Sp2/0 myeloma cells at a ratio of 1:1 in an electrofusion solution according to conventional electrofusion procedures. The fused cells were suspended in a DMEM medium supplemented with 20% FBS and 1×HAT, and then transferred to a 96-well plate (CORNING). The fused cells were cultured in an incubator set to 37° C., 5% $CO_2$ for 10-14 days.

1.2.3. Antibody Screening

First screening: Cell-based ELISA assay was used as the first screening to test the binding of hybridoma supernatant to human 4IgB7H3. Briefly, the human 4IgB7H3-transfected CHOK1 cell line in Example 1.1.3 was seeded into a 96-well plate (CORNING) at a density of $5\times10^3$ cells/well, and then kept in an incubator set to 37° C., 5% $CO_2$ for 2 days. The plate was then washed and incubated with the hybridoma supernatant at ambient temperature for 1 h. The plate was then washed, followed by incubation with secondary antibody goat anti-mouse IgG-Fc-HRP (Bethyl, A90-231P) for 1 h. After washing, TMB substrate was added and the interaction was stopped with 2M HCl. The absorbance at 450 nm was read using a microplate reader (Molecular Device).

Second screening: In order to confirm the binding of hybridoma supernatant to human and cynomolgus monkey antigens, FACS was performed. The parental CHOK1 cell line and the 4IgB7H3-transfected CHOK1 cell line in Example 1.1.3 were stained with CellTrace dye (Violet and FarRed, respectively), while the B7H3-transfected Flipin-CHO cell pool in Example 1.1.3 was prepared with no dye. After incubation for 15 min at ambient temperature and washing, three types of cells in equal amounts were mixed to $1\times10^6$ cells/mL. The mixture of the three cells was transferred into a 96-well U-bottom plate (BD) at a density of $1\times10^5$ cells/well. The hybridoma supernatant was then transferred to the plate and incubated at 4° C. for 1 h. After washing, a secondary antibody, i.e., goat anti-mouse IgG Fc PE (Jackson, 115-115-164), was added and incubated with the cells at 4° C. in the dark for 0.5 h. The cells were then washed and resuspended in 1×PBS/1% BSA before being analyzed by flow cytometry.

In order to test the binding of hybridoma supernatant to human 2IgB7H3, conventional ELISA assay was used. A plate was pre-coated with human 2IgB7H3 (0.2 µg/mL) at 100 µL/well at ambient temperature for 1 h. After blocking with 1×PBS/2% BSA at 200 µL/well for 1 h, the plate was washed 3 times with 1×PBST. The hybridoma supernatant was added into the plate in a volume of 100 μL/well and incubated at ambient temperature for 2 h. After washing the plate 3 times with 1×PBST, goat anti-mouse IgG-Fc HRP (Bethyl, A90-231P) was added into the plate at 100 μL/well and incubated at ambient temperature for 1 h. After washing 6 times, TMB substrate was added into the plate at 100 μL/well for color development for 5-10 min, and then the reaction was stopped by adding 2M HCl at 100 μL/well. The absorbance at 450 nm was read using a microplate reader.

The positive cell line selected by FACS screening was further confirmed by SPR (surface plasmon resonance). SPR allows real-time, label-free detection of bio-molecular interactions. SPR occurs when polarized light strikes an electrically conducting surface at the interface between two media. This generates electron charge density waves called plasmons, reducing the intensity of reflected light at a specific angle known as the resonance angle, in proportion to the mass on a sensor surface. The binding of the supernatant to human 4IgB7H3 was ranked using Biacore 8K. An activator was prepared by mixing 400 mM EDC and 100 mM NHS (GE) immediately prior to injection into the channel. The CM5 sensor chip was activated for 420 seconds with the activator. Goat anti-mouse Fc IgG (30 μg/mL in 10 mM NaAc, pH 4.5) was then injected into the channel at a flow rate of 10 μL/min for 420 seconds. The chip was deactivated with 1 M ethanolamine-HCl. The supernatant was injected into the channel at a flow rate of 10 μL/min for 30 seconds. 200 nM human 4IgB7H3 analyte was injected into the channel at a flow rate of 30 μL/min for an association phase of 120 seconds, followed by dissociation of 300 seconds. Glycine (10 mM, pH 1.5) was injected as regeneration buffer after the dissociation phase. The sensorgrams for the reference channel and the buffer channel were subtracted from the test sensorgrams. The data were then fitted with a 1:1 Langmuir binding model.

pHrodo iFL dyes can be conjugated to biomolecules such as antibodies, and become highly fluorescent only when present in acidic environments, such as those of cellular lysosomes and endosomes. This enables detection of the conjugated biomolecules in a living cell assay. AffiniPure F(ab')$_2$ fragment goat anti-human IgG Fcγ and anti-mouse IgG Fcγ were labeled with pHrodo iFL Red STP ester amine reactive dye and purified by Zeba Spin desalting column according to the manufacturer's instructions. MCF-7 cells expressing human full-length B7H3 ($2 \times 10^4$ cells/well) were seeded into a 96-well clear bottom black plate pre-coated with 8 μg/mL poly-D-lysine. The cells were grown in an incubator set to 37° C., 5% CO$_2$ overnight. On the next day, the supernatant from WBP301088-1 positive cell line was added into the corresponding wells in a volume of 100 μL. The cells were incubated in an incubator set to 37° C., 5% CO$_2$ for 0.5 h. Human and mouse IgG1 isotype antibodies were used as negative controls. 50 nM pHrodo iFL Red/F(ab')$_2$ goat anti-mouse or anti-human IgG Fcγ conjugates (diluted in a complete medium) were added in a volume of 100 μL/well. The plate was then incubated in an incubator set to 37° C., 5% CO$_2$ in the dark for 5 h. After incubation, the supernatant was discarded. The plate was washed with a complete medium. A mixed dye solution (1 μg/mL Hoechst 33342 and 0.5 μg/mL Calcein AM diluted in DPBS) was added into the plate in a volume of 100 μL/well and kept at ambient temperature for 15 min. After incubation, the dye solution was discarded and the plate was washed once with 1×PBS/1% BSA. The fluorescence intensity of the MCF-7 cells was read and analyzed by Perkin Elmer Operetta CLS high-content analysis system.

A total of 8460 wells were tested in the primary screen, and 279 hybridomas were selected and expanded in 24-well plates. In the secondary screen, supernatants from the 24-well plates were used to confirm strong binding to human 4IgB7H3 and cynomolgus monkey B7H3, weak binding to human 2IgB7H3, and strong internalization activity on MCF-7. Based on the results from the secondary screening, WBP301088-1.145 hybridoma was selected for subcloning.

1.2.4. Antibody Subcloning

The positive hybridoma cells selected in Example 1.2.3 were used for subcloning. The cells in logarithmic growth were counted and added to 1.5 mL of semi-solid HAT medium. The cells were mixed gently in a vortex shaker for 5-10 seconds and then seeded in a 6-well plate (CORNING). The plate was kept in an incubator set to 37° C., 5% CO$_2$ for 7-8 days. Each visible single colony was picked into 96-well plates (CORNING) with DMEM medium supplemented with 10% FBS. After 2-3 days, the cell supernatants were collected and screened by cell-based ELISA (human 4IgB7H3) and conventional ELISA (human 2IgB7H3) using the antibody screening protocol as described above. After confirmative screening of antibody subclones using cells expressing human 4IgB7H3 and cynomolgus monkey B7H3 by FACS, the culture supernatants of selected single positive clones were collected, and the antibodies were purified for further characterization. W301088-1.145.16 hybridoma clone was obtained after subclone screening and confirmative screening.

1.2.5. Antibody Isotyping

ELISA isotyping was performed in a 96-well high binding plate (Nunc). Each well was coated with 2 μg/mL capture antibodies goat anti-mouse IgG1 (Bethyl, A90-205A), goat anti-mouse IgG2a (Bethyl, A90-207A), goat anti-mouse IgG2b (Bethyl, A90-209A), or goat anti-mouse IgG3 (Bethyl, A90-211A), respectively at 4° C. overnight and blocked with 1×PBS/2% BSA. Hybridoma supernatants in Example 1.2.4 were incubated in the coated wells, and a peroxidase-conjugated goat anti-mouse κ/λ light chain antibody was used to measure the specific binding of the antibody to the capture antibody immobilized on the plate. HRP signal was detected by adding TMB substrate and the reaction was stopped after 12 min by 2M HCl. All incubation steps were performed at ambient temperature, and the plate was washed with PBS between steps. The absorbance at 450 nm was read using a microplate reader (Molecular Device).

The isotyping result of W301088-1.145.16 clone is shown in the table below (Table 4).

TABLE 4

| Isotyping result of W301088-1.145.16 clone | |
|---|---|
| Clone No. | Isotype |
| W301088-1.145.16 | IgG2b, κ |

1.2.6. Antibody Generation

When small amounts of purified antibody are required, a T75 flask (CORNING) is commonly used to perform scale-up of hybridoma cell culture. Monoclonal hybridoma cells were seeded into the flask at $5 \times 10^6$ to $1 \times 10^7$ cells/T75 flask. The cells were allowed to grow continuously for about 7-10 days until cell viability reached about 30%-40%. The culture supernatant was harvested, and the cell debris was removed by centrifugation. The supernatant was sterile-filtered and stored for antibody purification.

1.2.7. Hybridoma Sequencing

Total RNA of W-301088-1.145.16 hybridoma cell sample was first extracted according to the instructions of the TaKaRa MiniBEST universal RNA extraction kit. The RNA was then converted to cDNA using the SMART RACE cDNA amplification kit from Clonetech. The VH and VL domain DNA sequences were then amplified from the cDNA with 30 cycles of PCR, each cycle involving denaturation at 94° C. for 30 seconds, annealing at 60° C. for 30 seconds, followed by elongation at 72° C. for 30 seconds. The PCR product was then subcloned into a TA-cloning vector and sent to Biosune Biotech (Shanghai, China) for sequencing.

Once the sequencing data confirmed the monoclonality of the hybridoma cell sample, the DNA sequences of the VH and VL domains were amplified by PCR. Primers were synthesized by Sangon Biotech (Shanghai, China). The DNA segments were then subcloned into a pcDNA3.4 expression vector with human IgG1 constant region with LALA mutations and then sequenced by Tsingke Biotechnology (Beijing, China).

1.2.8. IgG Conversion

Once the sequencing data confirmed the monoclonality of the hybridoma cell sample, the nucleotide sequences encoding the amino acid sequences of the VH and VL domains were codon optimized for mammalian expression, and then the codon-optimized nucleotide sequences were synthesized by Sangon Biotech (Shanghai, China). The DNA segments were then subcloned into a pcDNA3.4 expression vector with human IgG1 constant region with L234A/L235A (LALA) mutations.

In this manner, the antibody produced by W301088-1.145.16 clone was converted into a human IgG1 antibody with LALA mutant form, thereby obtaining a chimeric antibody, designated antibody W301088-1.145.16-xIgG1KV320. After protein A purification and buffer exchange, it was characterized by SDS-PAGE and SEC-HPLC. The protein migrated on SDS-PAGE with apparent molecular weights of 50 kDa and 25 kDa under a reducing condition, corresponding to IgG heavy and light chains, respectively. The purity was higher than 99% (SEC-HPLC).

TABLE 5

Chimeric antibody generated

| Name of antibody | Concentration (mg/mL) | Buffer | Purity SEC-HPLC (%) | Theoretical molecular weight |
|---|---|---|---|---|
| W301088-1.145.16-xIgG1KV320 | 2.50 | PBS | 99.64% | 147 kDa |

1.2.9. Humanization of Antibody

A local copy of the open source software ANARCI (Dunbar J and Deane C M, "ANARCI: antigen receptor numbering and receptor classification", *Bioinformatics*, 2015; 32(5): 298-300) was run to assign Kabat numbering on the W301088-1.145.16 antibody. The CDRs were identified according to the definitions at Dr. Martin's website (Martin, 2018, supra) and are shown in Table 6.

TABLE 6

CDR ranges as defined by Dr. Martin's antibody informatics website

| CDR | Kabat | Residues before | Residues after | Length |
|---|---|---|---|---|
| L1 | L24-L34 | Always C | Always W | 10 to 17 residues |
| L2 | L50-L56 | 16 residues after L1 | / | 7 residues |
| L3 | L89-L97 | Always C | Always F-G-X-G | 7 to 11 residues |
| H1 | H31-H35b | Always C-X-X-X | Always W | 10 to 12 residues |
| H2 | H50-H65 | Typically L-E-W-G | K/R-L/I/V/F/T/A-T/S/I/A | 16 to 19 residues |
| H3 | H95-H102 | Typically C-A-R | Always W-G-X-G | 3 to 25 residues |

TABLE 7

VH and VL amino acid sequences of W301088-1.145.16 antibody with underlined CDR sequences

| Antibody ID | | Amino acid sequence |
|---|---|---|
| W301088-1.145.16 | VH | DVQLQESGPGLVKPSQSLSLTCTVTDYSITG DYAWNWIRQFPGNKLEWMGYISYSGSTSYNP SLQSRISITRDTSKNQFFLQLNSVTSEDTAT YFCARSLGRRWYFVVWGAGTTVTVSA (SEQ ID NO: 16) |
| | VL | DIVMTQSPSSLAMSVGQKVTMSCKSSQSLLN SSNQKNYLAWYQQKPGQSPKLLIYFASTRES GVPDRFIGSGSGTDFTLTISSVQAEDLTDYF CQQHYSAPWTFGGGTKLEIK (SEQ ID NO: 17) |

TABLE 8

Identified heavy and light chain CDR sequences of W301088-1.145.16 antibody

| Antibody | HCDR1 | HCDR2 | HCDR3 | LCDR1 | LCDR2 | LCDR3 |
|---|---|---|---|---|---|---|
| W301088-1.145.16 | SEQ ID NO: 1 DYSITG DYAWN | SEQ ID NO: 2 YISYSG STSYNP SLQS | SEQ ID NO: 3 SLGRRW YFVV | SEQ ID NO: 7 KSSQSL LNSSNQ KNYLA | SEQ ID NO: 5 FASTRE S | SEQ ID NO: 6 QQHYSA PWT |

The VH and VL domain sequences of the murine antibody W301088-1.145.16 were aligned to the human germline sequence libraries of the VH and VL domains of IMGT, respectively. The human germline sequence of the VH/VL domain with a minimal number of amino acid differences in the framework relative to the VH/VL domain sequence of the W301088-1.145.16 antibody was selected as the humanization template of the VH/VL domain. IGHV4-31*02 combined with IGHJ6*01 and IGKV4-1*01 combined with IGKJ4*01 were the human germline sequences most homologous to the VH and VL domain sequences of the W301088-1.145.16 antibody, respectively. The CDRs of the W301088-1.145.16 antibody were grafted into the frameworks of these two human germline templates to construct germline sequences.

Several "reverse mutation" positions in the framework were empirically selected to convert the amino acids in the germline sequence to their amino acid counterparts in the original murine sequence. A set of humanized variants were empirically designed to investigate different combinations of these selected reverse mutation sites. The germline sequence differed from the original murine W301088-1.145.16 antibody sequence at 16 positions in the VL domain and at 20 positions in the VH domain. Among the total 36 different sites, 14 sites were considered for reverse mutations: VH: Q001D, S025T, H040F, K043N, G044K, I048M, V067I, V071R, A085E, V089T, and Y091F; VL: I021M, P043S, and Y087F. A set of humanized variants were empirically designed to test different combinations of these three reverse mutations.

1.2.10. PTM Removal

The VH and VL domain sequences of the humanized variants were scanned for several types of critical post-translational modification (PTM) sites: asparagine deamination (N-G and N—S) in CDRs, aspartate isomerization (D-G) in CDRs, unpaired C in the entire length, and N-linked glycosylation sites (N—X—S/T in which X can be any amino acid except for P) in the entire length. Point mutations were empirically designed to remove these critical PTM sites in the humanized variants to avoid the potential risk of PTM modification. Finally, PTM-removed antibodies that did not affect the expression, binding and thermal stability compared to the parent antibody were selected.

Considering that the VL domain sequence of the murine antibody W301088-1.145.16 contains N—S—S N-linked glycosylation sites, three point mutations of VL: N027dQ, VL: S027eP, and VL: S027fA (numbered according to Kabat) were designed to remove the critical PTM sites. They were further characterized by $k_{off}$ ranking in conjunction with the humanization variants.

1.2.11. $k_{off}$ Ranking by SPR

The $k_{off}$ ranking of the filtered supernatants was performed on a Biacore 8K surface plasmon resonance (SPR) equipment. The CM5 sensor chip was first activated by 400 mM EDC and 100 mM NHS (GE) at a flow rate of 10 μL/min for 420 seconds. 30 μg/mL anti-human Fc IgG (Jackson) in 10 mM NaAc (pH 4.5) was then injected into channels 1 to 8 at a flow rate of 10 μL/min for 420 seconds. The chip was then deactivated by 1 M ethanolamine-HCl (GE) at a flow rate of 10 μL/min for 420 seconds. The diluted antibody supernatants were injected to Fc2 of the channels at a flow rate of 10 μL/min. A supernatant of the cell culture without plasmid transfection was used as a negative control and injected to Fc1 of the channels at a flow rate of 10 μL/min. 100 nM human 4IgB7H3 and running buffer were injected sequentially into Fc1-Fc2 of the channels at a flow rate of 30 μL/min for an association phase of 180 seconds, followed by a dissociation phase of 3600 seconds. 10 mM glycine (pH 1.5) was injected after each run to regenerate the chip. The sensorgrams were analyzed by the software bundled with the Biacore 8K equipment. The sensorgrams for the reference channel and the buffer channel were subtracted from those for the samples. The data were then fitted with a 1:1 Langmuir binding model.

1.2.12. Combination of PTM Removal Mutation with Humanized Variants

The PTM removal point mutation showing the best $k_{off}$ rate in Example 1.2.11 was combined into the humanized variants with the optimal $k_{off}$ rate by point mutagenesis to construct the final constructs for affinity validation.

According to the $k_{off}$ rate, the PTM removal mutation of VL: N027dQ was combined with four selected humanized mutant amino acids S025T, V071R, Y091F, and V089T to constitute the final antibody. The final antibody was designated W301088-1.145.16-z3-p1-uIgG1KV320.

TABLE 9

Heavy and light chain CDR sequences of W301088-1.145.16-z3-p1-uIgG1KV320

| Antibody | HCDR1 | HCDR2 | HCDR3 | LCDR1 | LCDR2 | LCDR3 |
|---|---|---|---|---|---|---|
| W301088-1.145.16-z3-p1-uIgG1KV320 | SEQ ID NO: 1 DYSITG DYAWN | SEQ ID NO: 2 YISYSG STSYNP SLQS | SEQ ID NO: 3 SLGRRW YFVV | SEQ ID NO: 4 KSSQSL LQSSNQ KNYLA | SEQ ID NO: 5 FASTRE S | SEQ ID NO: 6 QQHYSA PWT |

Figures 11, 12A:
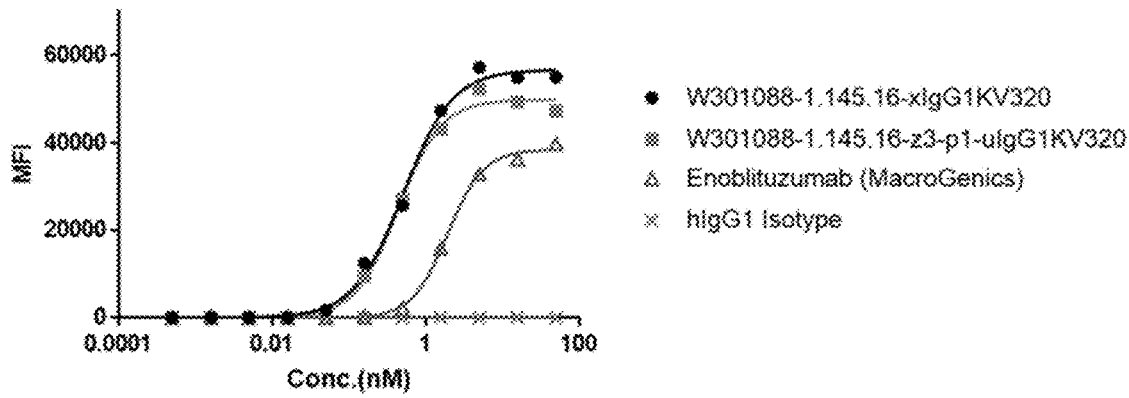
FIG. 11 shows internalization of antibodies W301088-1.145.16-xIgG1KV320 and W301088-1.145.16-z3-p1-uIgG1KV320 by human B7H3-expressing cells MCF-7 upon binding to the antibodies. Anti-B7H3 antibody enoblituzumab was used as a positive control, and hIgG1 isotype was used as a negative control.
FIGS. 12A-12B show amino acid sequence alignment of VH and VL regions between antibodies W301088-1.145.16-xIgG1KV320 and W301088-1.145.16-z3-p1-uIgG1KV320. Boxed amino acid segments in the figures are the respective CDR regions in the VH and VL regions.
Figures 12B, 13:
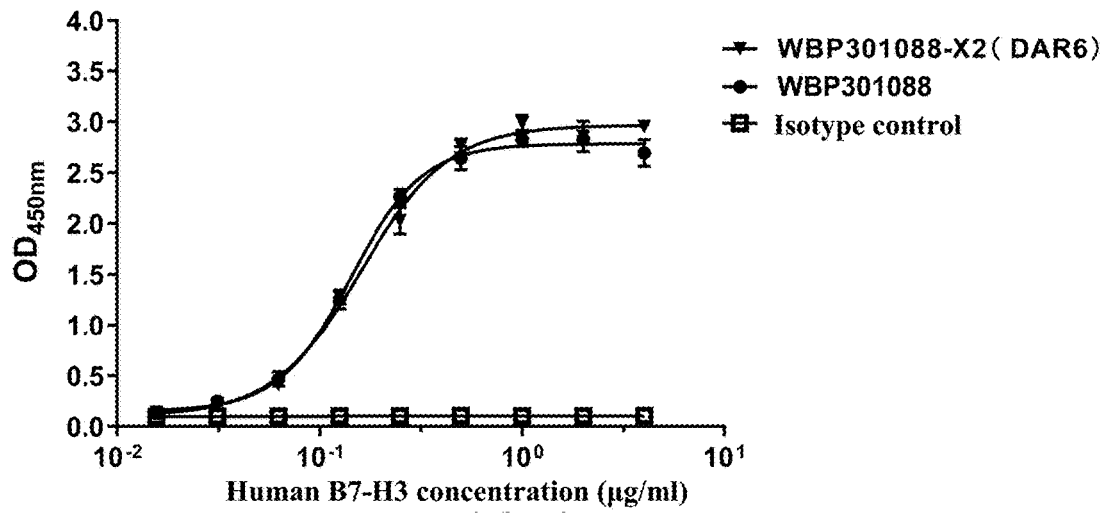
FIG. 13 shows detection of the binding activity of an antibody-drug conjugate and an unconjugated antibody thereof to human B7H3 antigen by ELISA. In the figure, "WBP301088" represents the unconjugated antibody W301088-1.145.16-z3-p1-uIgG1KV320.

FIGS. 12A-12B show the results of amino acid sequence alignment of VH and VL regions between antibodies W301088-1.145.16-xIgG1KV320 and W301088-1.145.16-z3-p1-uIgG1KV320. Boxed amino acid segments in the figures are the respective CDR regions in the VH and VL regions.

1.2.13. Production Scale Transient Transfection and Purification

The plasmids at a final concentration of 1 μg/mL were transiently transfected into 20 mL of Expi293F cells at a cell density of 3.0×10$^6$ cells/mL and with a cell viability of exceeding 95% using the ExpiFectamine™ transient transfection kit. The cell culture was grown in a humidified platform shaker at a rotation speed of 150 rpm. The temperature was maintained at 37° C., while the $CO_2$ level was maintained at 8%.

After 5 days of cell culture incubation, the supernatant expressing the target antibody was collected, filtered, and purified using a GE MabSelect SuRE protein A column (Cytiva-175438). The eluted antibody was dialyzed into PBS via D-Tube Dialyzer Maxi (EMD Millipore 71508, MWCO 3.5 kDa). Antibody concentration was determined by absorbance at 280 nm on a NanoDrop device. 2 μg of the purified antibody sample was electrophoresed on SDS-PAGE gel (Invitrogen NuPAGE™ 4%-12% Bis-Tris protein gel) with and without a reducing agent. The purity of the purified antibody sample was quantified by HPLC-SEC using a TSKgel G3000SWXL size exclusion chromatography column (Tosoh 008541). The purified antibody was stored at −80° C.

1.3. In vitro Characterization of Antibodies 1.3.1. SDS-PAGE and Purity Detection by SEC-HPLC The purified antibody sample in Example 1.2 was mixed with a loading buffer and heated at 75° C. for 10 min using a drying bath. After the sample was loaded, SDS-PAGE was run at a constant voltage (200V) for 35 min. The gel was stained and destained with eStain™ L1. SDS-PAGE results were obtained using BIO-RAD imaging system.

The results are summarized in Table 10 below. The protein migrated on SDS-PAGE with apparent molecular weights of 50 kDa and 25 kDa under a reducing condition, corresponding to IgG heavy and light chains, respectively, while migrated with expected ~150 kDa band under a non-reducing condition (FIG. 1).

1.3.2. Purity detection by SEC-HPLC

The purity of the antibody in Example 1.2 was detected by the Agilent 1260 Infinity II system (Agilent Technologics™) equipped with a TSKgel G3000SWXL column (Tosoh Bioscience-0008541). An antibody sample of appropriate volume (5-100 µL) was injected into the column and separated at a flow rate of 1 mL/min for 20 min. The running buffer was 50 mM sodium phosphate, 150 mM NaCl, pH 7.0. The peak retention was detected with UV light at a wavelength of 280 nm. The purity of the antibody was analyzed by integrating all peak areas from 4.5 min to 10.5 min using SEC-HPLC analysis method. The operation and analysis software was the OpenLab CDS workstation (v2.3.0.443 or v2.2.0.484).

Figure 2:
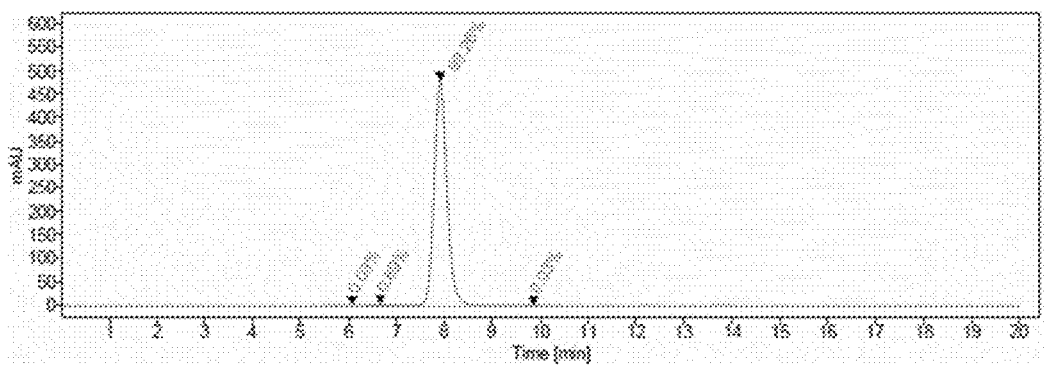
FIG. 2 shows SEC-HPLC results of W301088-1.145.16-z3-p1-uIgG1KV320.

The results are summarized in Table 10 below. The purity of the W301088-z3-p1 antibody was greater than 99% as detected by SEC-HPLC (FIG. 2).

1.3.3. Thermal Stability ($T_m$) Determined by DSF $T_m$ (melting temperature) of each antibody was investigated using QuantStudio® 7 Flex real-time PCR system (Applied Biosystems). 19 µL of the antibody solution in Example 1.2 was mixed with 1 µL of SYPRO Orange solution (Invitrogen) and transferred to a 96-well plate (Applied Biosystems). The plate was sealed with an optical adhesive film (Applied Biosystems) and centrifuged at 3,000 rpm for 5 min to remove any air bubbles. The plate was heated from 26° C. to 95° C. at a rate of 0.9° C./min, and the resulting fluorescence data were collected. The negative derivatives of the fluorescence changes with respect to different temperatures were calculated, and the maximum value was defined as the melting temperature $T_m$. If a protein has multiple unfolding transitions, the first $T_m$ were reported and designated $T_m1$. Data collection and $T_m$ calculation were performed automatically by QuantStudio® real-time PCR software (v1.3).

Figure 3:
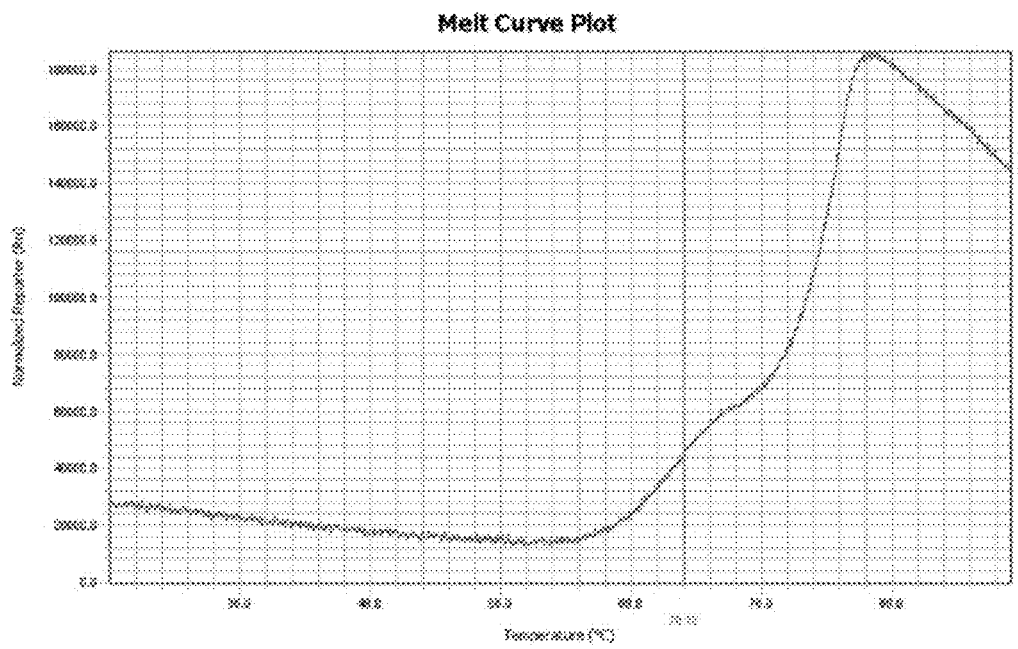
FIG. 3 shows DSF curve of W301088-1.145.16-z3-p1-uIgG1KV320.

The $T_m$ value of the W301088-1.145.16-z3-p1-uIgG1KV320 antibody was defined as the maximum value of the negative derivatives of the fluorescence changes with respect to different temperatures, as listed in Table 10 below. Data profile is shown in FIG. 3, where the dashed line indicates the position of the $T_m1$ value in the fluorescence curve. The $T_m1$ of the W301088-1.145.16-z3-p1-uIgG1KV320 antibody was 70.1° C., indicating that it had good thermal stability.

1.3.4. Detection of Hydrophobicity by HIC-HPLC

The hydrophobic property of the antibody in Example 1.2 was detected by HPLC 1260 infinity II system (Agilent Technologies™) with a TSKgel butyl-NPR column (Tosoh-0042168). Each antibody sample was diluted to 0.5 mg/mL with PBS buffer, and 20 µL of the diluted sample was injected into the column and separated at a flow rate of 0.5 mL/min for 61 min. The running buffers were 25 mM sodium phosphate, pH 7.0 (buffer A) and 25 mM sodium phosphate, 1.5 M $(NH_4)_2SO_4$, pH 7.0 (buffer D). The running gradient from 3 min to 53 min was from 0% to 100% buffer D. The peak retention was detected with UV light at wavelengths of 280 nm and 230 nm. The retention time was analyzed by integrating all peak areas from 20 min to 40 min using HIC-HPLC analysis method. The operation and analysis software was the OpenLab CDS workstation (v2.6.0.691).

Figure 4:
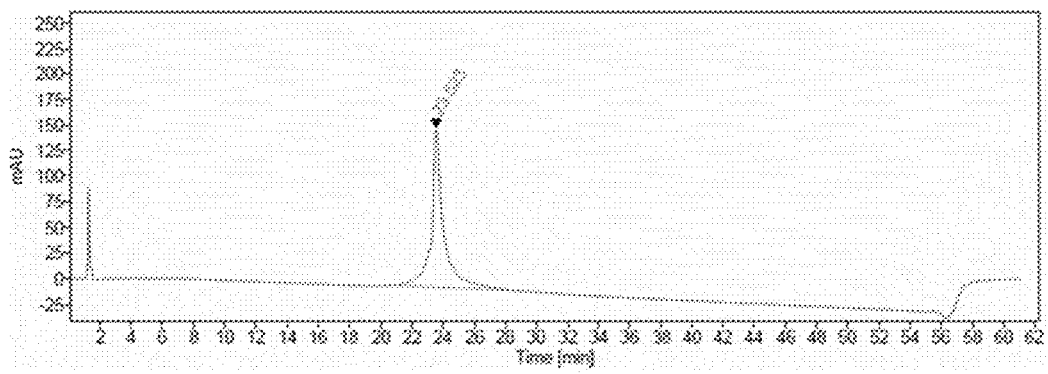
FIG. 4 shows HIC-HPLC curve of W301088-1.145.16-z3-p1-uIgG1KV320.

The HIC retention time of the W301088-1.145.16-z3-p1-uIgG1KV320 antibody was 23.52 min (Table 10 and FIG. 4), indicating that it is an antibody with good hydrophilicity.

1.3.5. Determination of Diffusion Interaction Parameter ($k_D$) by DLS

Figure 5:
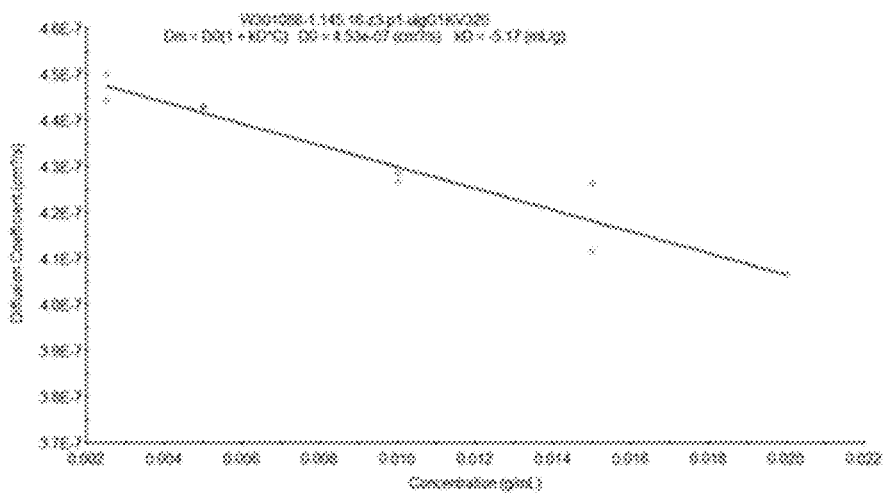
FIG. 5 shows DLS-$k_D$ curve of W301088-1.145.16-z3-p1-uIgG1KV320.

DLS-$k_D$ measurement was investigated using DynaPro plate reader III (Wyatt Technology). During the preparation of antibody samples, the appearance of the samples was recorded upon thawing, filtration and concentration. The antibody samples were concentrated to over 20 mg/mL and then diluted with PBS buffer to final concentrations of 2.5 mg/mL, 5 mg/mL, 10 mg/mL, 15 mg/mL, and 20 mg/mL. 7.5 µL of a sample solution was then added to a 1536-well microplate (Aurora-ABI1-00110A). The plate was sealed with ClearSeal film (Hampton Research-HR4-521) and centrifuged at 3,000 rpm for 5 min to allow the sample to descend to the bottom of the well. Each sample was tested in two duplicate wells. The plate was placed in the corresponding position and data collection was performed by the DYNAMICS operation software (v7.8.1.3). 5 acquisitions were collected for each protein sample while each acquisition time was 5 seconds. For each measurement, the diffusion coefficient was determined and plotted against the protein concentration. The $k_D$ value was calculated automatically by the software (v7.8.1.3), and the result is shown in Table 10. Data profile is shown in FIG. 5. The $k_D$ of the W301088-1.145.16-z3-p1-uIgG1KV320 antibody in PBS was −5.17 mL/g, indicating that it is an antibody with high solubility. During the assay, the appearance of the antibody protein was also recorded, and some particles were observed after thawing and gently shaking. If the buffer was exchanged to 20 mM His, 8% sucrose, 0.02% PS80, pH 6.5, no particle was observed. The above SDS-PAGE, SEC-HPLC, HIC-HPLC, DSF and DLS results are summarized in Table 10.

TABLE 10

Summary of analysis data of W301088-1.145.16-z3-p1-uIgG1KV320 antibody

| Name of antibody | Purity detected by SEC-HPLC | Yield (mg/L) | Molecular weight | pI | HIC retention time (min) | $T_m$ (° C.) | DLS-$k_D$ (mL/g) |
|---|---|---|---|---|---|---|---|
| W301088-1.145.16-z3-p1-uIgG1KV320 | 99.26% | 416.0 | 147 kDa | 8.54 | 23.52 | 70.1 | −5.17 |

1.3.6. Binding to Human B7H3 (FACS)

FACS was used to detect the binding of antibodies to human B7H3. This method allows quantitative analysis and identification of specific molecules expressed on the surface of living cells. Unlabeled cells were used as a control to set a threshold before the assay, and the percentage change for each group that exceeded the fluorescence intensity threshold was analyzed. MCF-7 cells expressing human full-length B7H3 ($1×10^5$ cells/well) were incubated with various concentrations of antibodies (3.16-fold serially diluted with 1×DPBS/1% BSA from 50 nM to 0.0005 nM) in a volume of 100 μL/well in a refrigerator set to 4° C. for 1 h. Anti-human B7H3 reference antibody enoblituzumab (MacroGeneics) was used as a positive control. Human IgG1 isotype antibody was used as a negative control. After washing the cells with 1×DPBS/1% BSA, Alexa 647 goat anti-human antibody (diluted in a 1:500 ratio in 1×DPBS/1% BSA) was added. The cells were incubated in a refrigerator set to 4° C. for 0.5 h in the dark. The mean fluorescence intensity (MFI) of the cells was measured by a flow cytometry and analyzed by FlowJo. $EC_{50}$ values were calculated by four-parameter non-linear regression analysis using GraphPad Prism 7 software.

Figure 6:
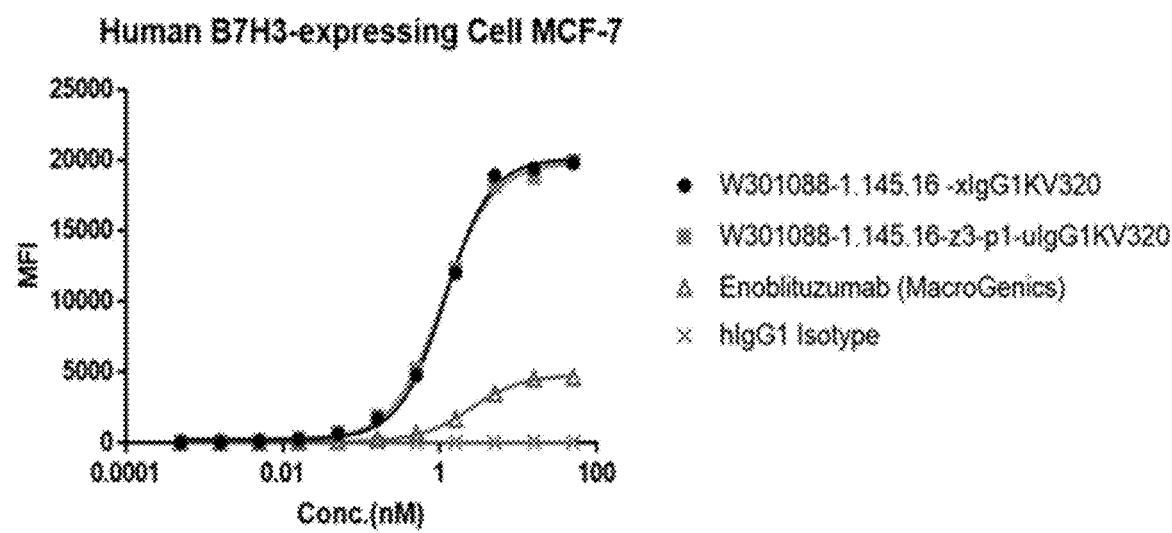
FIG. 6 shows FACS results of binding of antibodies W301088-1.145.16-xIgG1KV320 and W301088-1.145.16-z3-p1-uIgG1KV320 to human B7H3-expressing cells MCF-7. Anti-B7H3 antibody enoblituzumab was used as a positive control, and hIgG1 isotype was used as a negative control.

The W301088-1.145.16-z3-p1-uIgG1KV320 antibody showed good binding to B7H3-expressing MCF-7 cells with an $EC_{50}$ value of 1.08 nM and max MFI of 19900, which was comparable to the chimeric antibody W301088-1.145.16-xIgG1KV320 and better than the reference antibody enoblituzumab (MacroGenics) (Table 11, FIG. 6).

TABLE 11

FACS binding data on human B7H3-expressing cells MCF-7

| Antibody sample | MCF-7 | |
|---|---|---|
| | $EC_{50}$ (nM) | Maximum MFI |
| W301088-1.145.16-xIgG1KV320 | 1.16 | 19800 |
| W301088-1.145.16-z3-p1-uIgG1KV320 | 1.08 | 19900 |
| Enoblituzumab (MacroGenics) | 2.49 | 4644 |
| hIgG1 isotype | N.A. | 47.8 |

Note:
N.A. means not available.

1.3.7. Binding to Cynomolgus Monkey B7H3 (FACS)

FACS was used to detect the binding of antibodies to cynomolgus monkey B7H3. FlpinCHO cells were transfected with cynomolgus monkey B7H3 (W3XX088-Flpin-CHO.cPro1.pool) (1×10$^5$ cells/well), and the transfected cells were incubated with various concentrations of antibodies (3.16-fold serially diluted with 1×DPBS/1% BSA from 50 nM to 0.0005 nM) in a volume of 100 μL/well in a refrigerator set to 4° C. for 1 h. Anti-human B7H3 reference antibody enoblituzumab (MacroGenics) was used as a positive control. Human IgG1 isotype antibody was used as a negative control. After washing the cells with 1×DPBS/1% BSA, Alexa 647 goat anti-human antibody (diluted in a 1:500 ratio in 1×DPBS/1% BSA) was added. The cells were incubated in a refrigerator set to 4° C. for 0.5 h in the dark. The mean fluorescence intensity (MFI) of the cells was measured by a flow cytometry and analyzed by FlowJo. $EC_{50}$ values were calculated by four-parameter non-linear regression analysis using GraphPad Prism 7 software.

Figure 7:
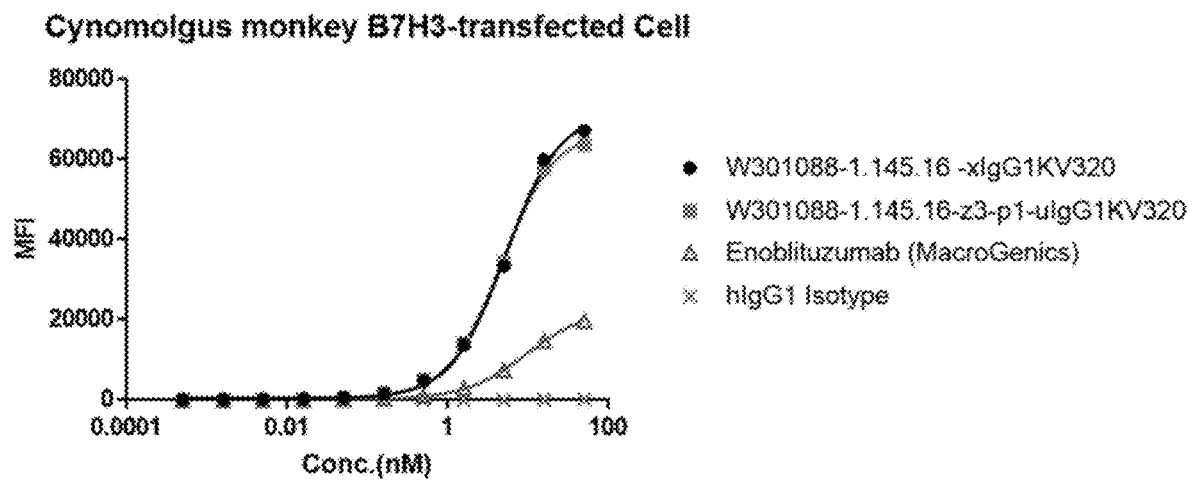
FIG. 7 shows FACS results of binding of antibodies W301088-1.145.16-xIgG1KV320 and W301088-1.145.16-z3-p1-uIgG1KV320 to cynomolgus monkey B7H3-transfected cells. Anti-B7H3 antibody enoblituzumab was used as a positive control, and hIgG1 isotype was used as a negative control.

The W301088-1.145.16-z3-p1-uIgG1KV320 antibody showed good binding to the cynomolgus monkey-transfected cells with an $EC_{50}$ value of 4.68 nM, which was comparable to the chimeric antibody W301088-1.145.16-xIgG1KV320 and better than enoblituzumab (MacroGenics) (Table 12, FIG. 7).

TABLE 12

FACS binding data on cynomolgus monkey B7H3-transfected stable cell pool

| | Cynomolgus monkey B7H3-transfected stable cell pool | |
|---|---|---|
| Antibody sample | $EC_{50}$ (nM) | Maximum MFI |
| W301088-1.145.16-xIgG1KV320 | 5.25 | 67100 |
| W301088-1.145.16-z3-p1-uIgG1KV320 | 4.68 | 63600 |
| Enoblituzumab (MacroGenics) | 9.58 | 19700 |
| hIgG1 isotype | N.A. | 6.67 |

Note:
N.A. means not available.

1.3.8. Binding Affinity for Human 4IgB7H3 (SPR)

The affinity of antibodies for human 4IgB7H3 was determined using surface plasmon resonance (SPR). The affinity of antibodies for human 4IgB7H3 was determined by Biacore 8K. An activator was prepared by mixing 400 mM EDC and 100 mM NHS (GE) immediately prior to injection into the channel. The CM5 sensor chip was activated for 420 seconds with the activator. Goat anti-human Fc IgG (30 μg/mL in 10 mM NaAc, pH 4.5) was then injected into the channel at a flow rate of 10 μL/min for 420 seconds. The chip was deactivated by 1 M ethanolamine hydrochloric acid. The antibodies diluted in running buffer (1×HBS-EP+) were injected into the channel at a flow rate of 10 μL/min for 30 seconds. Seven concentrations (100 nM, 50 nM, 25 nM, 12.5 nM, 6.25 nM, 2.125 nM, and 1.563 nM) of analyte human 4IgB7H3 were injected sequentially into the channel at a flow rate of 30 μL/min for an association phase of 180 seconds, followed by dissociation of 3600 seconds. Glycine (10 mM, pH 1.5) was injected as regeneration buffer after the dissociation phase.

The sensorgrams for the reference channel and the buffer channel were subtracted from the test sensorgrams. The experimental data were fitted with a 1:1 binding model. The molecular weight of the human 4IgB7H3 used in the calculation was 47.8 kDa.

Figure 8A:
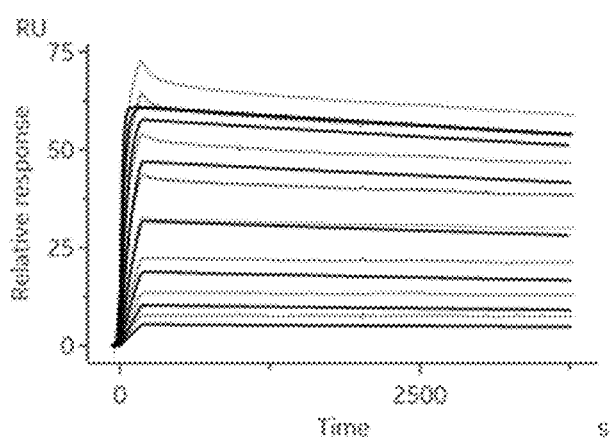
FIGS. 8A-8C show binding of antibodies W301088-1.145.16-xIgG1KV320 (FIG. 8A), W301088-1.145.16-z3-p1-uIgG1KV320 (FIG. 8B), and MacroGenics' enoblituzumab (FIG. 8C) to human 4IgB7H3.
Figure 8B:
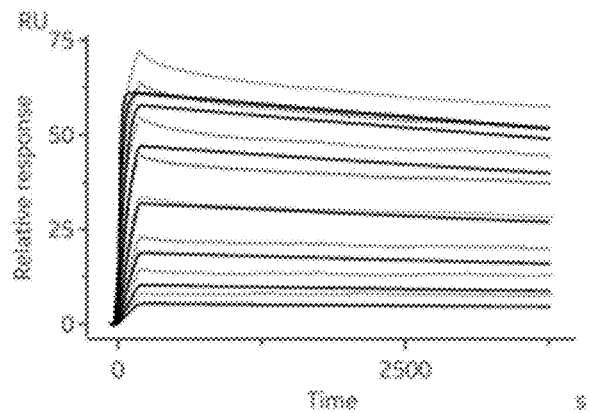
Figure 8C:
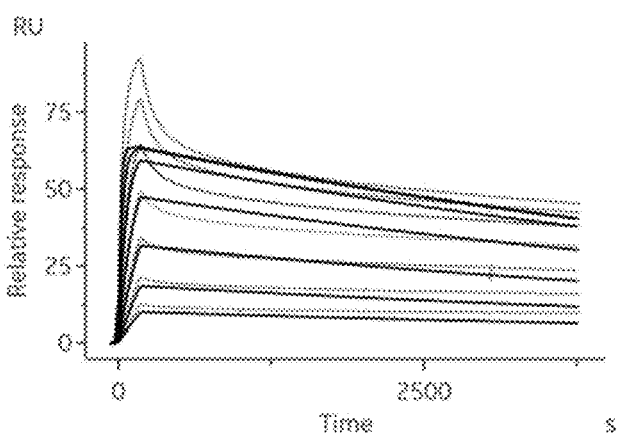

The experimental data were fitted by a 1:1 binding model bundled with the Biacore 8K evaluation software. As shown in Table 13 and FIGS. 8A-8C, the W301088-1.145.16-z3-p1-uIgG1KV320 antibody showed high binding affinity for human 4IgB7H3. The $K_D$ value was 7.08E-11 M, which was better than that of enoblituzumab (MacroGenics).

TABLE 13

Results of antibodies binding affinity for human 4IgB7H3

| Analyte | Antibody | $k_a$ (1/Ms) | $k_d$ (1/s) | $K_D$ (M) |
|---|---|---|---|---|
| Human 4IgB7H3 | W301088-1.145.16-xIgG1KV320 | 6.57E+05 | 3.39E-05 | 5.15E-11 |
| | W301088-1.145.16-z3-p1-uIgG1KV320 | 6.57E+05 | 4.65E-05 | 7.08E-11 |
| | Enoblituzumab (MacroGenics) | 1.24E+05 | 1.26E-04 | 1.02E-09 |

1.3.9. Binding Affinity for Human 2IgB7H3 (SPR)

The affinity of antibodies for human 2IgB7H3 was determined using surface plasmon resonance (SPR). The affinity of antibodies for human 2IgB7H3 was determined by Biacore 8K. An activator was prepared by mixing 400 mM EDC and 100 mM NHS (GE) immediately prior to injection into the channel. The CM5 sensor chip was activated for 420 seconds with the activator. Goat anti-human Fc IgG (30 µg/mL in 10 mM NaAc, pH 4.5) was then injected into the channel at a flow rate of 10 µL/min for 420 seconds. The chip was deactivated by 1 M ethanolamine hydrochloric acid. The antibodies diluted in running buffer (1×HBS-EP+) were injected into the channel at a flow rate of 10 µL/min for 30 seconds. Seven concentrations (500 nM, 250 nM, 125 nM, 62.5 nM, 31.25 nM, 15.625 nM, and 7.813 nM) of analyte human 2IgB7H3 were injected sequentially into the channel at a flow rate of 30 µL/min for an association phase of 120 seconds, followed by dissociation of 300 seconds. Glycine (10 mM, pH 1.5) was injected as regeneration buffer after the dissociation phase.

The sensorgrams for the reference channel and the buffer channel were subtracted from the test sensorgrams. The experimental data were fitted with a 1:1 binding model. The molecular weight of the human 2IgB7H3 used in the calculation was 25.2 kDa.

Figure 9A:
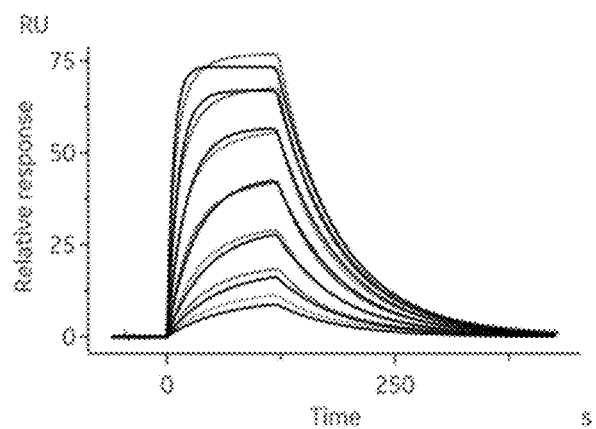
FIGS. 9A-9C show binding of antibodies W301088-1.145.16-xIgG1KV320 (FIG. 9A), W301088-1.145.16-z3-p1-uIgG1KV320 (FIG. 9B), and MacroGenics' enoblituzumab (FIG. 9C) to human 2IgB7H3.
Figure 9B:
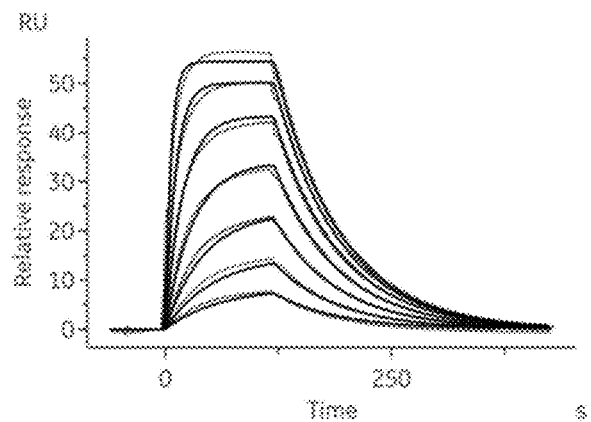
Figure 9C:
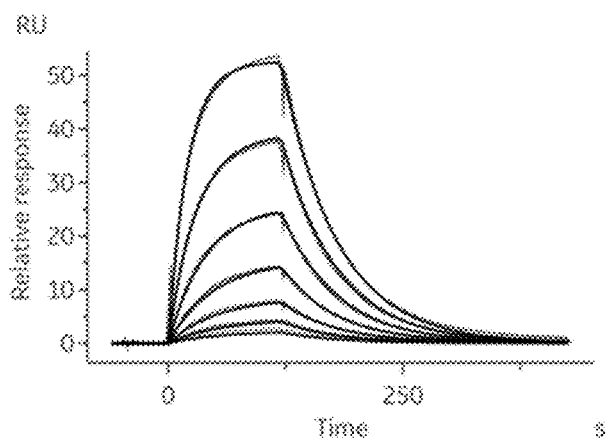

The experimental data were fitted by a 1:1 binding model bundled with the Biacore 8K evaluation software. As shown in Table 14 and FIGS. 9A-9C, the W301088-1.145.16-z3-p1-uIgG1KV320 antibody showed weaker binding affinity for human 2IgB7H3 compared to its binding to human 4IgB7H3. The $K_D$ value was 4.64E-08 M.

TABLE 14

Results of antibodies binding affinity for human 2IgB7H3

| Analyte | Antibody | $k_a$ (1/Ms) | $k_d$ (1/s) | $K_D$ (M) |
|---|---|---|---|---|
| Human 2IgB7H3 | W301088-1.145.16-xIgG1KV320 | 2.35E+05 | 1.36E-02 | 5.77E-08 |
| | W301088-1.145.16-z3-p1-uIgG1KV320 | 3.03E+05 | 1.41E-02 | 4.64E-08 |
| | Enoblituzumab (MacroGenics) | 6.44E+04 | 1.68E-02 | 2.61E-07 |

1.3.10. Binding Affinity for Cynomolgus Monkey B7H3 (SPR)

The affinity of antibodies for cynomolgus monkey B7H3 was determined using surface plasmon resonance (SPR). The affinity of antibodies for cynomolgus monkey B7H3 was determined by Biacore 8K. An activator was prepared by mixing 400 mM EDC and 100 mM NHS (GE) immediately prior to injection into the channel. The CM5 sensor chip was activated for 420 seconds with the activator. Goat anti-human Fc IgG (30 µg/mL in 10 mM NaAc, pH 4.5) was then injected into the channel at a flow rate of 10 µL/min for 420 seconds. The chip was deactivated by 1 M ethanolamine hydrochloric acid. The antibodies diluted in running buffer (1×HBS-EP+) were injected into the channel at a flow rate of 10 µL/min for 30 seconds. Nine concentrations (50 nM, 25 nM, 12.5 nM, 6.25 nM, 3.125 nM, 1.563 nM, 0.781 nM, 0.391 nM, and 0.196 nM) of analyte cynomolgus monkey B7H3 were injected sequentially into the channel at a flow rate of 30 µL/min for an association phase of 180 seconds, followed by dissociation of 3600 seconds. Glycine (10 mM, pH 1.5) was injected as regeneration buffer after the dissociation phase.

The sensorgrams for the reference channel and the buffer channel were subtracted from the test sensorgrams. The experimental data for 6 analyte concentrations (50 nM, 25 nM, 12.5 nM, 6.25 nM, 3.125 nM, and 1.563 nM) were fitted with a 1:1 binding model. The molecular weight of the cynomolgus monkey B7H3 used in the calculation was 49 kDa.

Figure 10A:
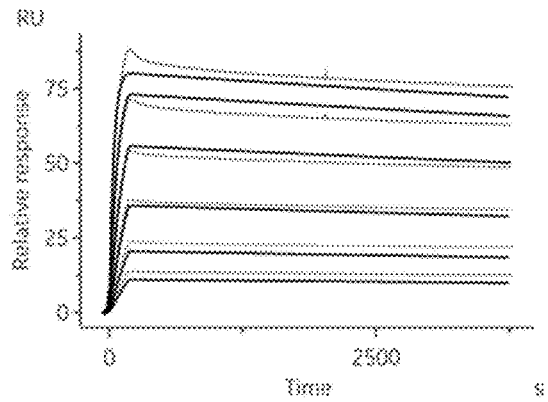
FIGS. 10A-10C show binding of antibodies W301088-1.145.16-xIgG1KV320 (FIG. 10A), W301088-1.145.16-z3-p1-uIgG1KV320 (FIG. 10B), and MacroGenics' enoblituzumab (FIG. 10C) to cynomolgus monkey B7H3.
Figure 10B:
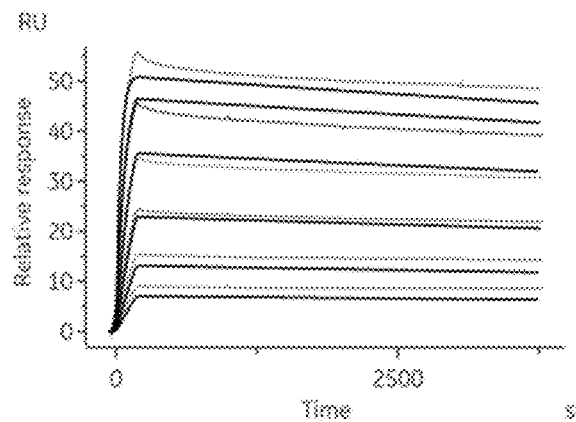
Figure 10C:
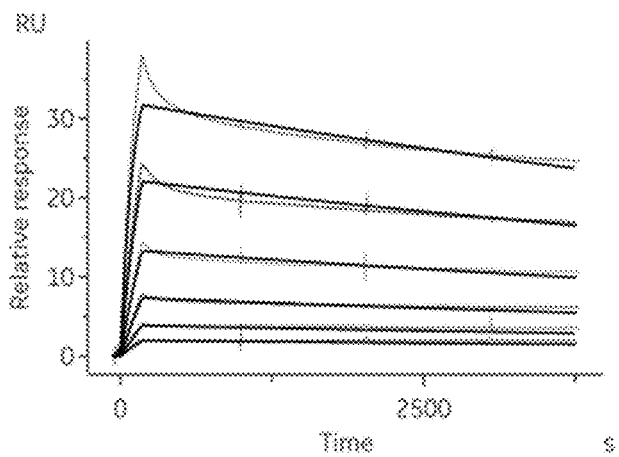

The experimental data were fitted by a 1:1 binding model bundled with the Biacore 8K evaluation software. As shown in Table 15 and FIGS. 10A-10C, the W301088-1.145.16-z3-p1-uIgG1KV320 antibody showed high binding affinity for cynomolgus monkey B7H3, which was comparable to its binding to human 4IgB7H3. The $K_D$ value was 5.74E-11 M, which was better than that of enoblituzumab (MacroGenics).

TABLE 15

Results of antibodies binding affinity for cynomolgus monkey B7H3

| Analyte | Antibody | $k_a$ (1/Ms) | $k_d$ (1/s) | $K_D$ (M) |
|---|---|---|---|---|
| Cynomolgus monkey B7H3 | W301088-1.145.16-xIgG1KV320 | 5.21E+05 | 2.94E-05 | 5.64E-11 |
| | W301088-1.145.16-z3-p1-uIgG1KV320 | 5.27E+05 | 3.02E-05 | 5.74E-11 |
| | Enoblituzumab (MacroGenics) | 1.85E+05 | 8.14E-05 | 4.41E-10 |

1.3.11. Internalization Test (HCS)

Antibody internalization was determined by operetta CLS (PerkinElmer), a high-content imaging and analysis system that can collect and analyze images of samples at high speed and high sensitivity. MCF-7 cells expressing human full-length B7H3 ($1.5 \times 10^4$ cells/well) were seeded into a 96-well clear bottom black plate pre-coated with 8 µg/mL poly-D-lysine. After incubation in an incubator set to 37° C., 5% $CO_2$ overnight, various concentrations of the antibodies (3.16-fold serially diluted with 1×DPBS/1% BSA from 50 nM to 0.0005 nM) were incubated in a volume of 100 µL/well in a refrigerator set to 4° C. for 2 h. Anti-human B7H3 reference antibody enoblituzumab (MacroGeneics) was used as a positive control. Human IgG1 isotype antibody was used as a negative control. After washing the cells with 1×DPBS/1% BSA, Alexa 647 goat anti-human antibody (diluted in a 1:500 ratio in 1×DPBS/1% BSA) was added. The cells were incubated in a refrigerator set to 4° C. for 1 h in the dark. The cells were then washed once and resuspended in 1×DPBS/1% BSA at 37° C. for 2 h. After incubation, the supernatant was discarded, and Hoechst 33342 (diluted in a 1:5000 ratio in 1×DPBS) was added at 100 µL/well and incubated at ambient temperature for 15 min. After washing the cells with 1×DPBS, an acid washing buffer (100 mM glycine, 150 mM NaCl, pH 2.5) was added at 100 µL/well and incubated in a refrigerator set to 4° C. for 5 min. The cells were washed once with 1×DPBS and immobilized with 60 µL of 4% PFA. The mean fluorescence intensity (MFI) of the cells was measured and analyzed by operetta CLS. $EC_{50}$ values were calculated by four-parameter non-linear regression analysis using GraphPad Prism 7 software.

The W301088-1.145.16-z3-p1-uIgG1KV320 antibody was shown to be internalized by B7H3-expressing MCF-7 cells with an $EC_{50}$ value of 0.51 nM, indicating a good internalization ability, which was comparable to that of the chimeric antibody W301088-1.145.16-xIgG1KV320 and better than that of the reference antibody enoblituzumab (MacroGenics) (Table 16, FIG. 11).

TABLE 16

Internalization of antibodies by human B7H3-expressing cells MCF-7

| Sample | Antibody internalization | |
|---|---|---|
| | $EC_{50}$ (nM) | Maximum MFI |
| W301088-1.145.16-xIgG1KV320 | 0.51 | 57180 |
| W301088-1.145.16-z3-p1-uIgG1KV320 | 0.44 | 52315 |
| Enoblituzumab (MacroGenics) | 1.95 | 39777 |
| hIgG1 isotype | N.A. | 21 |

Note:
N.A. means not available.

Example 2. Preparation of Antibody-Drug Conjugate (ADC) and Binding Activity to B7H3 Antigen The anti-B7H3 antibody used in the antibody-drug conjugate in this example was W301088-1.145.16-z3-p1-uIgG1KV320 (WBP301088 for short) or W301088-1.145.16-xIgG1KV320. W301088-1.145.16-z3-p1-uIgG1KV320 (WBP301088) comprises a heavy chain amino acid sequence as set forth in SEQ ID NO: 12 and a light chain amino acid sequence as set forth in SEQ ID NO: 13.

2.1. Preparation of Linker-Cytotoxin (Linker-Payload)
2.1.1. Preparation of Linker-Payload X1

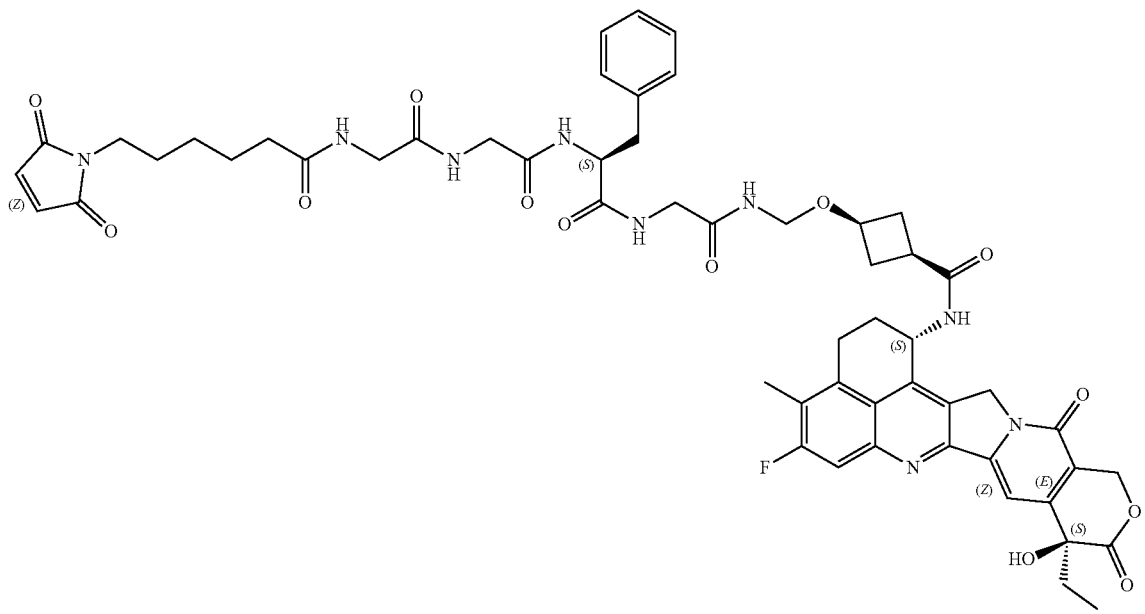

X1

The protocol for the preparation of linker-payload X1 was as follows:

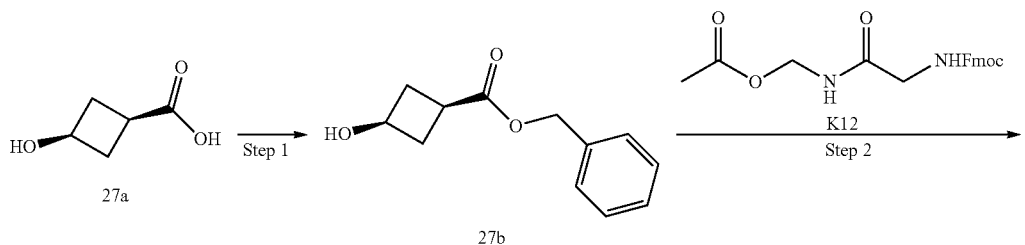

-continued
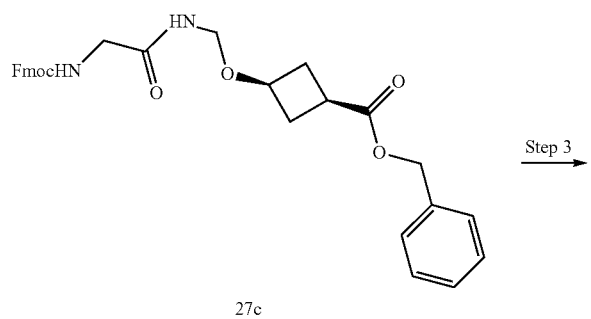
27c
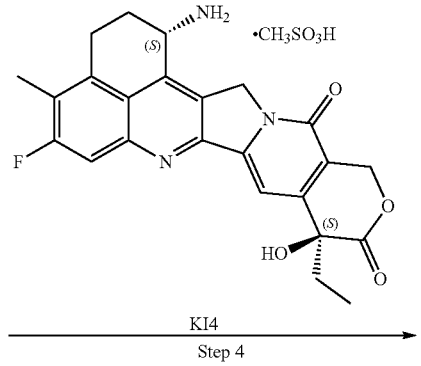
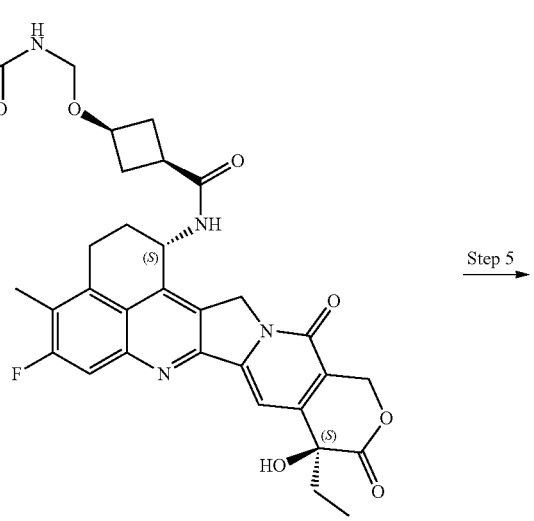
27d
27e
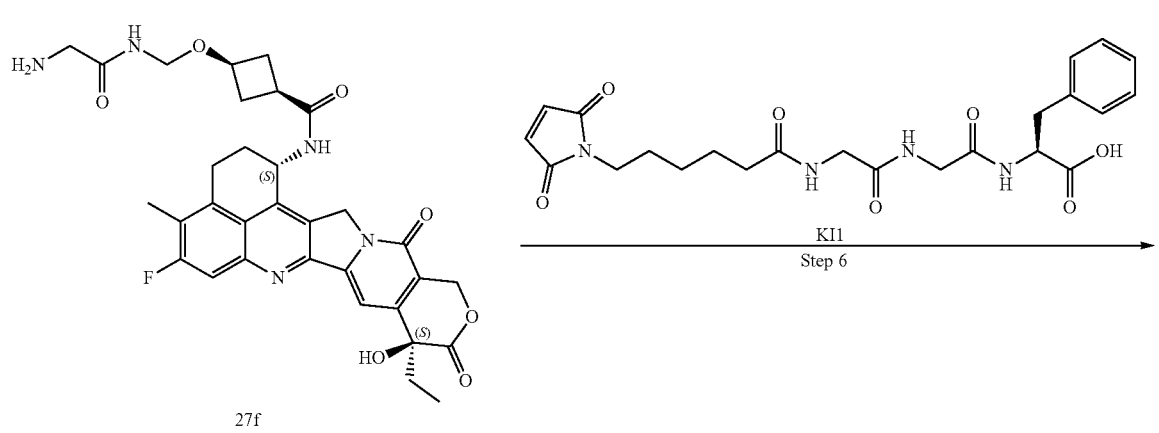
27f

-continued

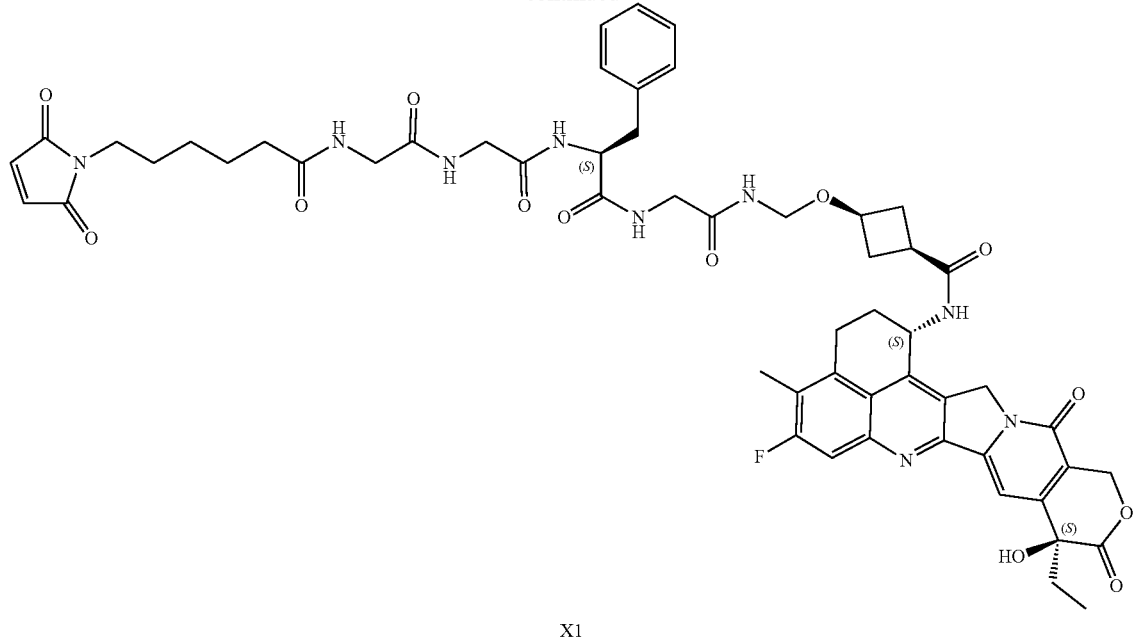

X1

Step 1

Benzyl bromide (11.0 g, 64.6 mmol) was added dropwise to a solution of 27a (5.00 g, 43.0 mmol), NaHCO$_3$ (10.9 g, 129 mmol) in DMF (50 mL) under nitrogen, and the mixture was reacted at 25° C. for 17 h. After the reaction was completed as shown by TLC (PE/EA=2/1) (PE is an abbreviation for petroleum ether; EA is an abbreviation for ethyl acetate), the reaction mixture was added to water (500 mL) and extracted twice with EA (250 mL). The organic phase was separated, washed with saturated aqueous sodium chloride solution (500 mL), dried over anhydrous Na$_2$SO$_4$, concentrated, and purified by column chromatography (PE: EA=3:2) to give a colorless liquid (5.1 g, 57.1% yield).

Step 2

A solution of 27b (4.50 g, 21.8 mmol) in THF (10 mL) was added dropwise to a solution of KI2 (4.00 g, 10.9 mmol) and TsOH (800 mg, 4.65 mmol) in THF (30 mL) at 0° C. under nitrogen, and the mixture was reacted at 25° C. for 2 h. After the reaction was completed as shown by TLC (PE/EA=1/2), the reaction mixture was added to water (200 mL) and extracted twice with EA (200 mL). The organic phase was separated, dried over anhydrous Na$_2$SO$_4$, concentrated, and purified by column chromatography (PE/EA=3/2) to give a white solid (1.56 g, 26% yield).

Step 3

Pd/C (80 mg) was added to a solution of 27c (800 mg, 1.55 mmol) in a mixture of EtOH (8 mL) and EA (8 mL) at 0° C. under hydrogen, and the resulting mixture was stirred at 0° C. for 2.5 h. After the reaction was completed as shown by LCMS, the reaction mixture was filtered through celite, and the filter cake was washed with EA (200 mL). The filtrate was concentrated and dissolved in THF (20 mL), and the resulting solution was concentrated to dryness by rotary evaporation to give a white solid (600 mg, 91% yield).

Step 4

DIEA (152 mg, 1.18 mmol) was added to a solution of 27d (220 mg, 0.515 mmol), KI4 (250 mg, 0.47 mmol) and HATU (214 mg, 0.56 mmol) in DMF (6 mL) at 0° C. under nitrogen, and the mixture was reacted at 0° C. for 2 h. After the reaction was completed as shown by LCMS, the reaction mixture was added to an aqueous citric acid solution (pH=4) (150 mL), and the resulting mixture was filtered. The filter cake was washed with water (175 mL), drained, and dried with an oil pump to give a brown solid (260 mg, 66% yield).

Step 5

Diethylamine (8 mL) was added dropwise to a solution of 27e (260 mg, 0.309 mmol) in dichloromethane (DCM) (30 mL) at 0° C. under nitrogen, and the mixture was reacted at 0° C. for 3 h. After the reaction was completed as shown by LCMS, the reaction mixture was added to a petroleum ether solution (600 mL) at 0° C., and a solid precipitated. The mixture was let stand until the solid adhered to the bottom of the flask, and the solution was poured out. The residue was dried with an oil pump to give a brown solid (90 mg, 47.1% yield).

Step 6

HATU (74 mg, 0.19 mmol) was added to a solution of 27f (90 mg, 0.13 mmol), KI-1 (92 mg, 0.19 mmol) and DIEA (50 mg, 0.39 mmol) in DMF (2.5 mL) at 0° C. under nitrogen, and the mixture was reacted at 0° C. for 2 h. After the reaction was completed as detected by LCMS, the reaction mixture was added to a pH 4 aqueous citric acid solution (30 mL) at 0° C., and a flocculent solid precipitated. The solid was collected by filtration and purified by preparative thin-layer chromatography (DCM/MecOH=10/1) to give X1 as a pale yellow solid (9.2 mg, 6% yield).

MS m/z (ESI): 1074 [M+1]

H—NMR (400 MHz, MeOD): 7.65 (d, 1H), 7.62 (s, 1H), 7.30-7.21(m, 5H), 6.79 (s, 2H), 5.69-5.65 (m, 1 H), 5.57 (d, 1H), 5.43-5.10 (m, 3H), 4.70 (d, 2H), 4.48-4.39 (m, 2H), 4.10-4.05 (m, 1H), 4.01-3.75 (m, 5H),3.46 (t, 2H), 3.22-3.15 (m, 2H), 3.07-3.00 (m, 1H), 2.75 (m, 1H), 2.62 (m, 1H), 2.45 (s, 3H), 2.37-2.20 (m, 6H), 2.10-2.02 (m, 2H), 2.00-1.92 (m, 2H) 1.68-1.57 (m, 6H), 1.01 (t, 3H)

2.1.2. Preparation of Linker-Payload X2
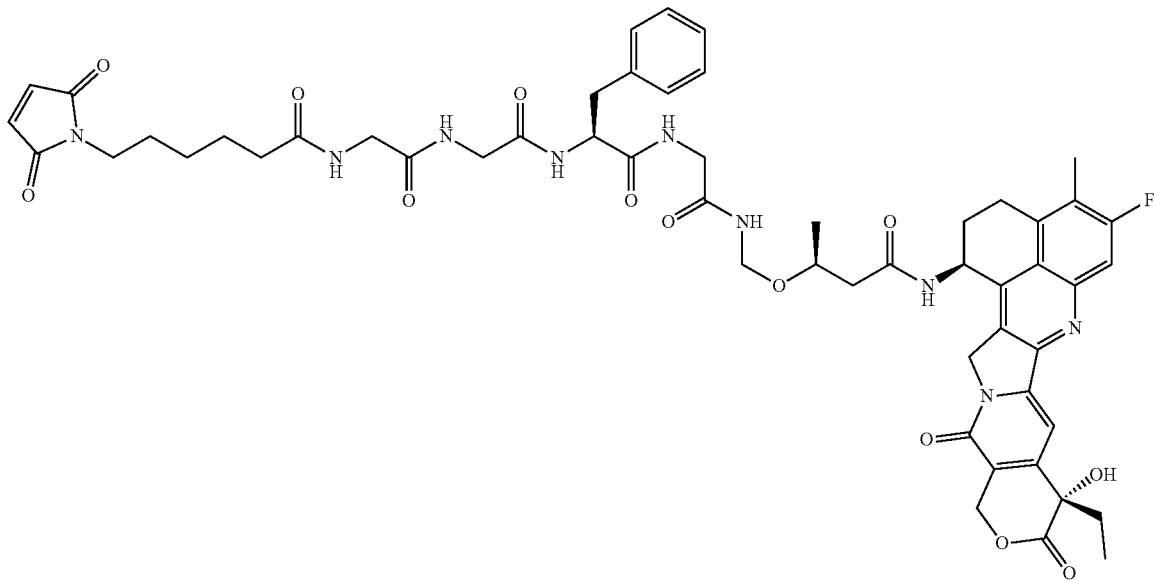
The protocol for the preparation of linker-payload X2 was as follows:
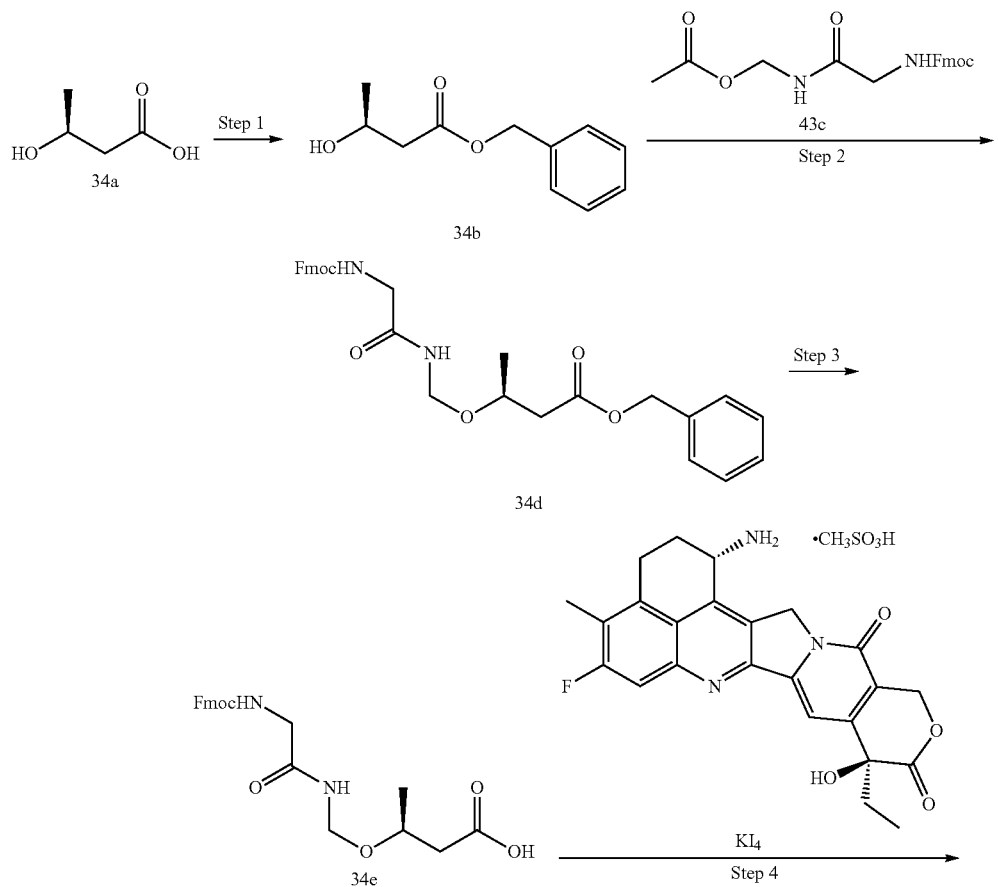

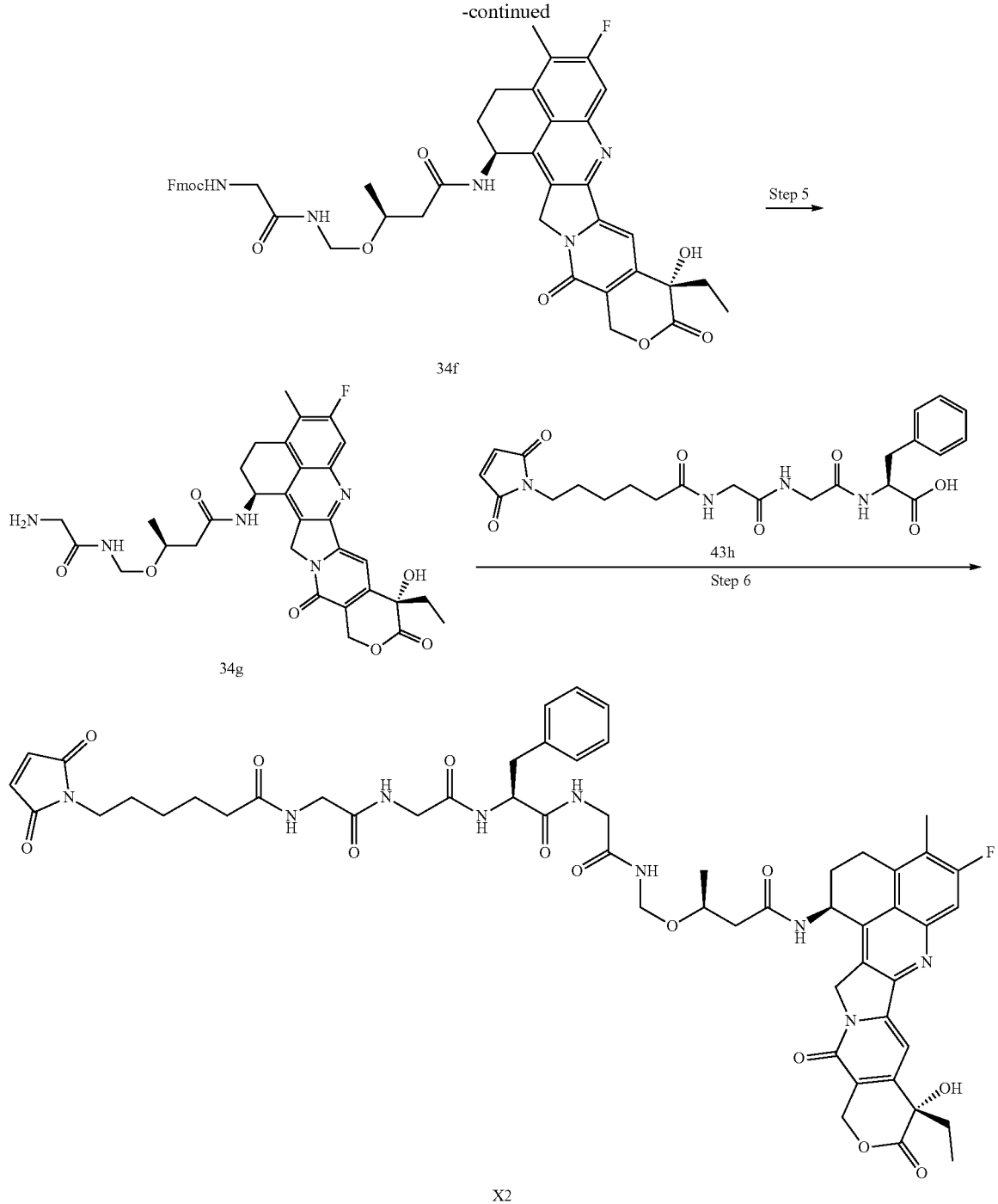

Step 1

34a (5 g, 48.0 mmol) and K₂CO₃ (19.9 g, 144.0 mmol) were dissolved in DMF (20 mL), and the resulting solution was added dropwise to benzyl bromide (12.3 g, 72.0 mmol). The mixture was reacted at 25° C. for 17 h. After the starting material was consumed completely as detected by TLC (PE/EA=3/1), the reaction mixture was added to water (200 mL) and extracted with EA (250 mL). The organic phase was separated, washed with saturated NaCl, dried over anhydrous Na₂SO₄, concentrated, and purified by column chromatography (PE:EA=2:1) to give 34b as a colorless liquid (8.7 g, 93% yield).

MS-ESI: m/z 195.1 [M+H]+.

Step 2

43c (7.3 g, 19.8 mmol) and TsOH (1.46 g, 8.5 mmol) were dissolved in THF (20 mL), and the resulting solution was cooled to 0° C. under nitrogen. A solution of 34b (7.7 g, 39.6 mmol) in THF (10 mL) was added dropwise, and after the addition, the mixture was reacted at 0° C. for 2 h. After most of the starting material was consumed as shown by TLC (PE/EA=2/1), the reaction mixture was poured into water (100 mL) and extracted with DCM (100 mL). The organic phase was separated, washed with saturated NaCl, dried over anhydrous Na₂SO₄, and purified by column chromatography (PE/EA=1/1) to give 34d as a colorless sticky substance (3.9 g, 39% yield). MS-ESI: m/z 503.3 [M+H]+.

Step 3

Pd/C (1 g, 10 wt.%) was added to a solution of 34d (1.9 g, 3.78 mmol) in a mixture of EtOH (100 mL) and EA (100 mL) was added at 0° C. under hydrogen, and the resulting mixture was reacted at 0° C. for 3 h. After the reaction was completed as shown by TLC (PE/EA=2/1), the reaction mixture was filtered through celite, and the filter cake was washed with EA/EtOH (1:1, 100 mL×3). The filtrate was concentrated. The residue was dissolved in THF (50 mL×3), and the resulting solution was concentrated to dryness by rotary evaporation; the procedure was repeated three times to give 34e as a gray solid (1 g, 64% yield). MS-ESI: m/z 435.2 [M+Na]+.

Step 4

DIEA (303 mg, 2.35 mmol) was added dropwise to a solution of 34e (426 mg, 1.03 mmol), KI4 (500 mg, 0.94 mmol) and HATU (429 mg, 1.13 mmol) in DMF (20 mL) at 0° C. under nitrogen, and after the addition, the mixture was reacted at 0° C. for 2 h. After the reaction was completed as shown by LCMS, the reaction mixture was added dropwise to water (300 mL). The resulting mixture was stirred, then let stand for 5 min, and filtered, and the filter cake was dissolved in DCM/MeOH (10:1, 100 mL) solution. The resulting solution was dried and concentrated to dryness by rotary evaporation, and the residue was mixed with silica gel and purified by column chromatography (EA:MeOH=30:1) to give 34f as a yellow solid (600 mg, 77% yield). MS-ESI: m/z 830.3 [M+H]+.

Step 5

Diethylamine (5 mL) was added dropwise to a solution of 34f (150 mg, 0.18 mmol) in DCM (5 mL) at 0° C. under nitrogen, and the mixture was reacted at 0° C. for 2 h. After the reaction was completed as shown by LCMS, a petroleum ether solution (100 mL×6) was added to the reaction mixture, and a solid precipitated. The resulting mixture was let stand until the solid settled, and the solution was poured out. The residue was dried with an oil pump to give 34g as a white powder (120 mg, 76% yield), with a product content of 70% as determined by LCMS. MS-ESI: m/z 608.3 [M+H]+.

Step 6

A solution of HATU (45 mg, 0.118 mmol) in DMF (1 mL) was added to a solution of 34g (60 mg, 0.099 mmol), 43h (51 mg, 0.108 mmol) and DIEA (32 mg, 0.25 mmol) in DMF (1 mL) at 0° C. under nitrogen, and the mixture was reacted at 0° C. for 2 h. After the starting material was consumed completely as shown by LCMS, the reaction mixture was directly purified by reversed-phase column chromatography (eluent: (MeCN/MeOH=1/1):H2O=60%:40%) to give X2 as a yellow solid (14.8 mg, 14% yield).

MS-ESI: m/z 1062.4 [M+H]+.

1H NMR (400 MHz, Methanol-d4) δ 7.69-7.61 (m, 2H), 7.22-7.16 (m, 2H), 7.16-7.09 (m, 3H), 6.76 (s, 2H), 5.70-5.64 (m, 1H), 5.60 (d, J=16.4 Hz, 1H), 5.40-5.31 (m, 2H), 5.26 (d, J=19.0 Hz, 1H), 4.65-4.50 (m, 7H), 4.25-4.16 (m, 1H), 3.87 (d, J=16.7 Hz, 1H), 3.83-3.76 (m, 3H), 3.72 (d, J=17.0 Hz, 2H), 3.44 (t, J=7.1 Hz, 2H), 3.25-3.17 (m, 2H), 3.10-3.02 (m, 1H), 2.92-2.83 (m, 1H), 2.45-2.39 (m, 5H), 2.32-2.20 (m, 5H), 1.97-1.89 (m, 2H), 1.63-1.50 (m, 4H), 1.34-1.20 (m, 6H), 0.99 (t, J=7.3 Hz, 3H).

2.1.3. Preparation of Linker-Payload X3

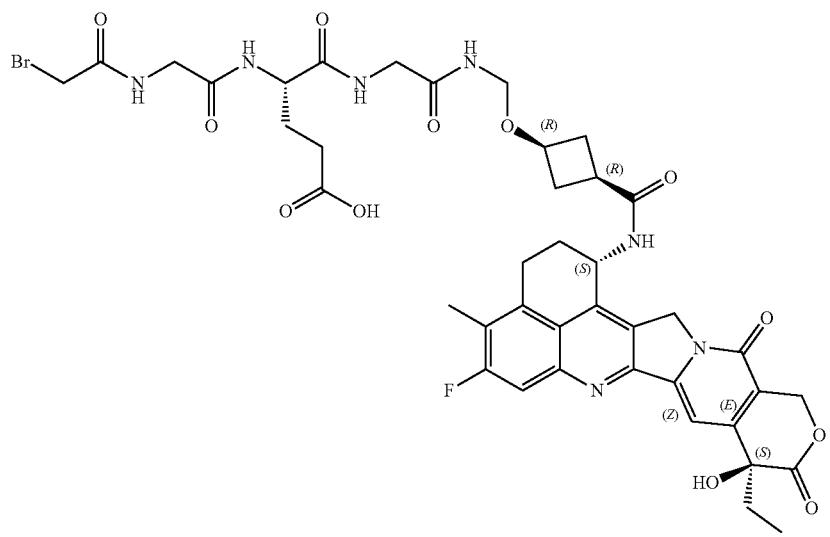

X3

The protocol for the preparation of linker-payload X3 was as follows:
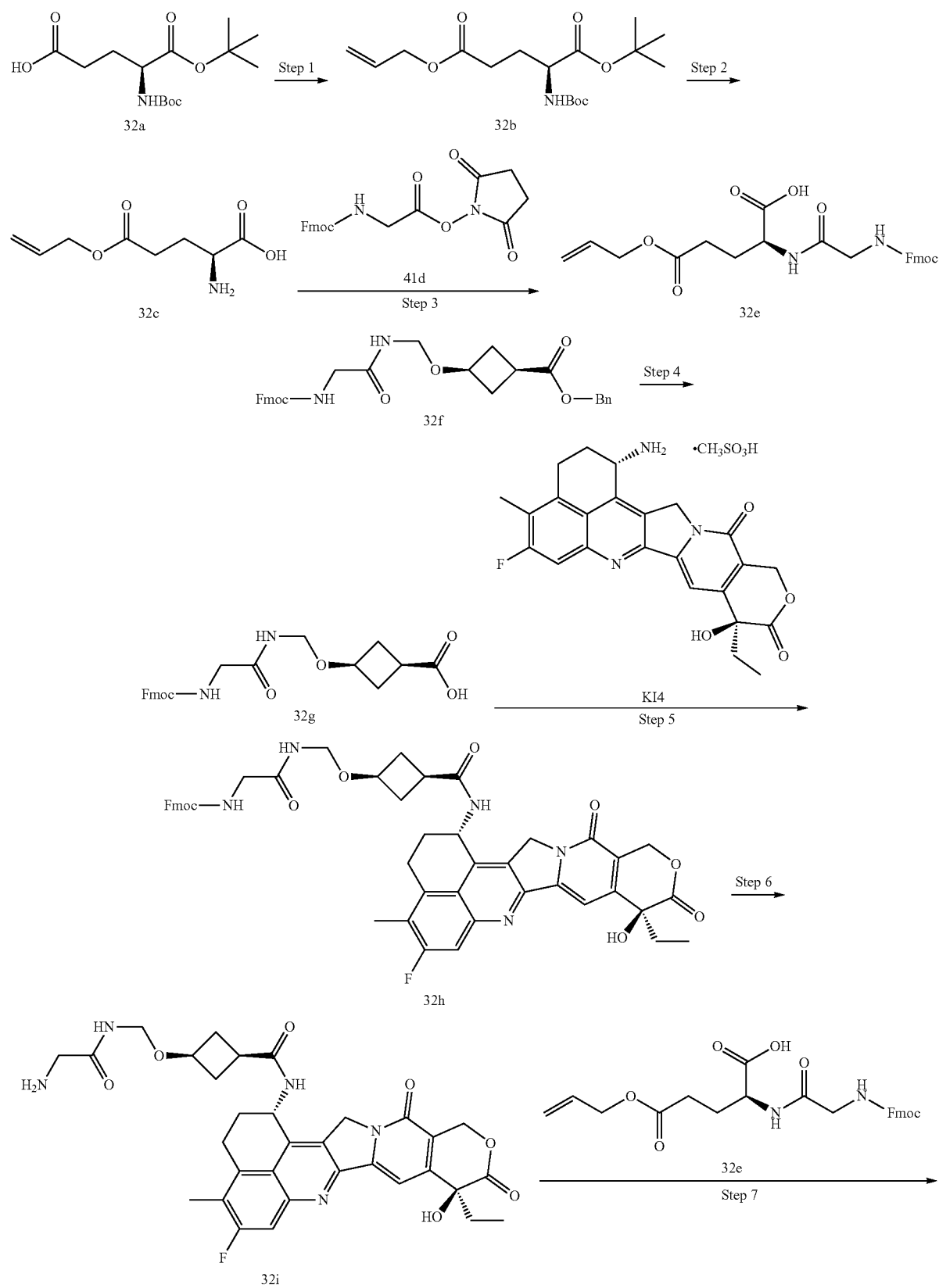

-continued
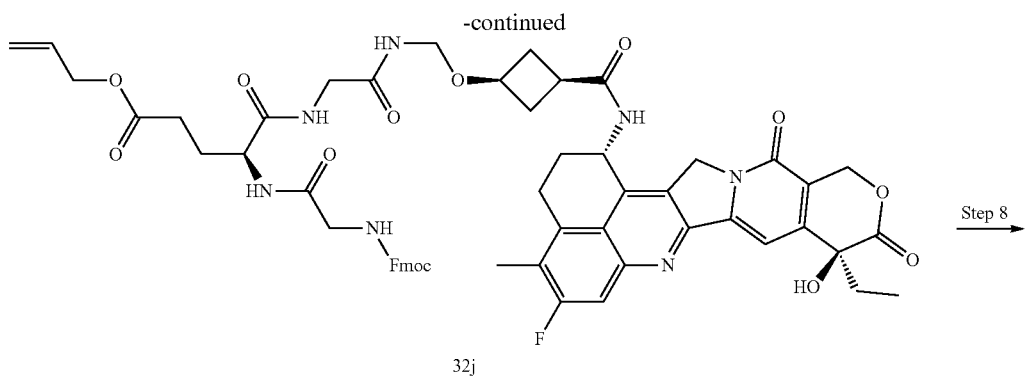
32j
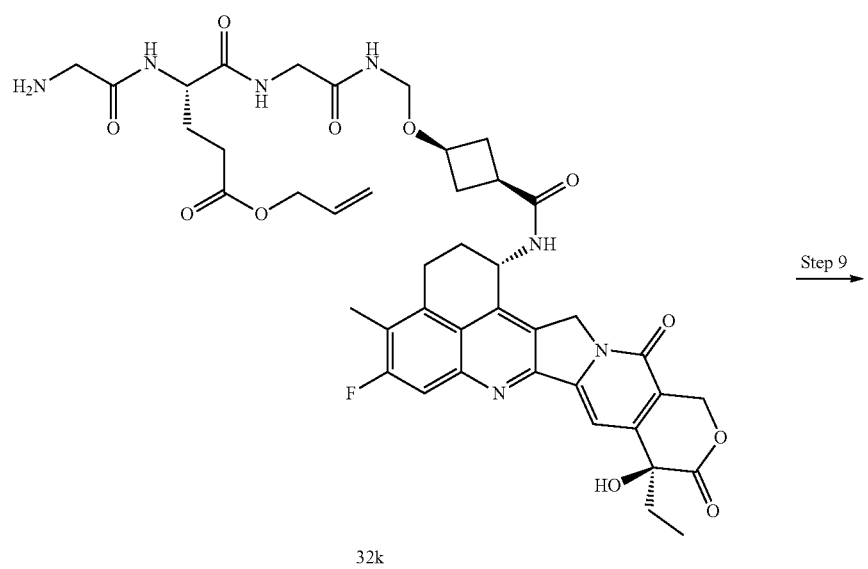
32k
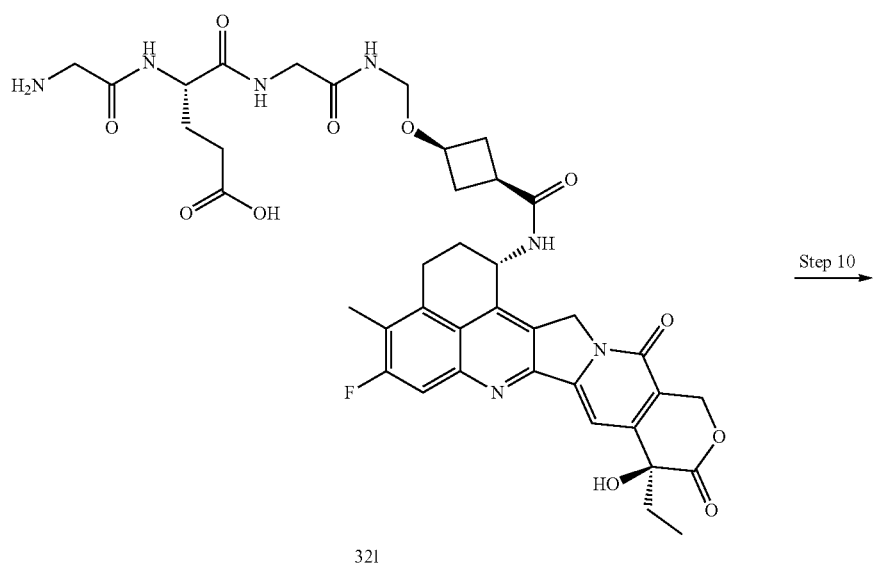
32l

-continued

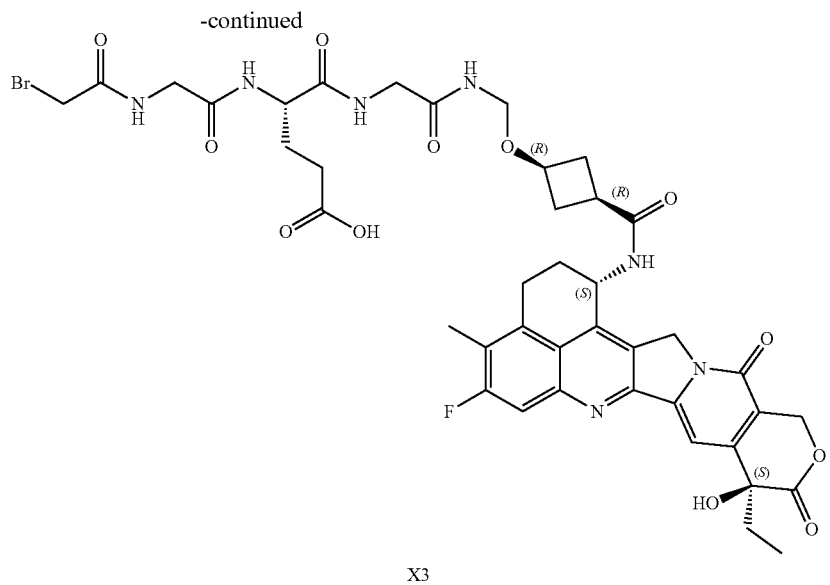

X3

Step 1

Bromopropene (960 mg, 7.92 mmol) was added to 32a (2.00 g, 6.6 mmol) and K₂CO₃ (1.82 g, 13.2 mmol) in MeCN (20 mL), and the mixture was stirred at 20° C. for 5 h. After the reaction was completed as shown by TLC (PE/EA=1/2), the reaction mixture was poured into water (100 mL), adjusted to pH 5, and extracted three times with EA (100 mL). The organic phase was dried over anhydrous sodium sulfate and concentrated to dryness by rotary evaporation, and the residue was purified by column chromatography (PE/EA=2/1) to give 32b as a white solid (1.83 g, 81% yield).

Step 2

TFA (10 mL) was added to 32b (1.38 g, 4.02 mmol) in DCM (10 mL), and the mixture was stirred at 25° C. for 17 h. After the reaction was completed as shown by TLC (PE/EA=1/3), the reaction mixture was concentrated to dryness by rotary evaporation to give 32c as a yellow sticky substance (0.91 g, yield not calculated).

Step 3

41d (1.92 g, 4.87 mmol) was added to 32c (910 mg, 4.87 mmol) and NaHCO₃ (613 mg, 7.3 mmol) in DME/H₂O (20 mL/10 mL), and the mixture was stirred at 25° C. for 3 h. After the reaction was completed as shown by TLC (DCM/MeOH=1/1), the reaction mixture was poured into water (100 mL), adjusted to pH 5 with aq. HCl (1 N), and extracted twice with EA (150 mL). The organic phase was dried over anhydrous sodium sulfate and concentrated to dryness by rotary evaporation, and the residue was purified by column chromatography (DCM/MeOH=20/1) to give 32e as a white solid (1.53 g, 67% yield). MS-ESI: m/z 467.4 [M+H]+.

Step 4

Pd/C (600 mg) was added to 32f (3 g, 5.83 mmol) in MeOH (50 mL), and the mixture was stirred under hydrogen at 25° C. for 5 h. After the reaction was completed as shown by TLC (EA), the reaction mixture was filtered, and the filtrate was concentrated to dryness by rotary evaporation to give 32g as a white solid (1.9 g, 77% yield).

Step 5

HATU (707 mg, 1.86 mmol) was added to 32g (789 mg, 1.86 mmol), KI4 (900 mg, 1.69 mmol) and triethylamine (342 mg, 3.38 mmol) in DMF (10 mL), and the mixture was stirred at 0° C. for 3.5 h. After the reaction was completed as shown by TLC (EA), the reaction mixture was poured into H₂O (80 mL) and extracted twice with EA (100 mL). The organic phase was dried over anhydrous sodium sulfate and concentrated to dryness by rotary evaporation, and the residue was purified by column chromatography (EA) to give 32h as a white solid (1.186 g, 83% yield). MS-ESI: m/z 842.3 [M+H]+.

Step 6

32h (1.186 g, 1.41 mmol) in DCM/diethylamine (20 mL, 20/1) was stirred at 25° C. for 17 h. After the reaction was completed as shown by TLC (DCM/MeOH=10/1), the reaction mixture was poured into petroleum ether (200 mL), and the resulting mixture was filtered to give 32i as a white solid (768 mg, 88% yield). MS-ESI: m/z 620.3 [M+H]+.

Step 7

HATU (414 mg, 1.09 mmol) was added to 32i (676 mg, 1.09 mmol), 32e (508 mg, 1.09 mmol) and DIEA (423 mg, 3.27 mmol) in DMF (10 mL), and the mixture was stirred at 20° C. for 17 h. After the reaction was completed as shown by TLC (PE/EA=1/5), the reaction mixture was poured into water (30 mL). The resulting mixture was filtered, and the filter cake was purified by column chromatography (DCM/MeOH=50/1) to give 32j as a white solid (511 mg, 44% yield). MS-ESI: m/z 1068.3 [M+H]+.

Step 8

A solution of 32j (482 mg, 0.451 mmol) in diethylamine/DCM (10 mL, 1/5) was stirred at 10° C. for 17 h. After the reaction was completed as shown by TLC (EA), the reaction mixture was poured into PE (300 mL), and the resulting mixture was filtered to give 32k as a white solid (301 mg, yield not calculated).

Step 9

Morpholine (93 mg, 1.07 mmol) was added to 32k (301 mg, 0.356 mmol) and Pd(PPh3)₄ (82 mg, 0.071 mmol) in THF (5 mL), and the mixture was stirred at 25° C. for 5 h. After the reaction was completed as shown by LCMS, the reaction mixture was purified by preparative chromatography to give 32l as a white solid (108 mg, 38% yield). MS-ESI: m/z 806.3 [M+H]+.

Step 10

Bromoacetyl bromide (27 mg, 0.134 mmol) was added to 321 (108 mg, 0.134 mmol) and triethylamine (41 mg, 0.402 mmol) in THF (2 mL) and DMF (2 mL), and the mixture was stirred at 0° C. for 1 h. After the reaction was completed as shown by TLC (DCM/MeOH=10/1), the reaction mixture was directly purified by preparative chromatography to give X3 as a white solid (15 mg, 12% yield).

MS-ESI: m/z 926.3 [M+H]+.

1H NMR (400 MHz, DMSO-d6) δ 12.11 (s, 1H), 8.54-8.42 (m, 3H), 8.27-8.16 (m, 2H), 7.78 (d, J=11.0 Hz, 1H), 7.30 (s, 1H), 6.53 (s, 1H), 5.61-5.51 (m, 1H), 5.42 (s, 2H), 5.20-5.05 (m, 2H), 4.56-4.42 (m, 2H), 4.32-4.22 (m, 1H), 3.96-3.87 (m, 3H), 3.79 (d, J=5.6 Hz, 2H), 3.70 (d, J=5.9 Hz, 2H), 3.25-3.08 (m, 2H), 2.61-2.53 (m, 2H), 2.45-2.36 (m, 4H), 2.36-2.22 (m, 3H), 2.20-2.03 (m, 4H), 1.99-1.68 (m, 4H), 0.87 (t, J=7.3 Hz, 3H).

2.1.4. Preparation of Linker-Payload X4

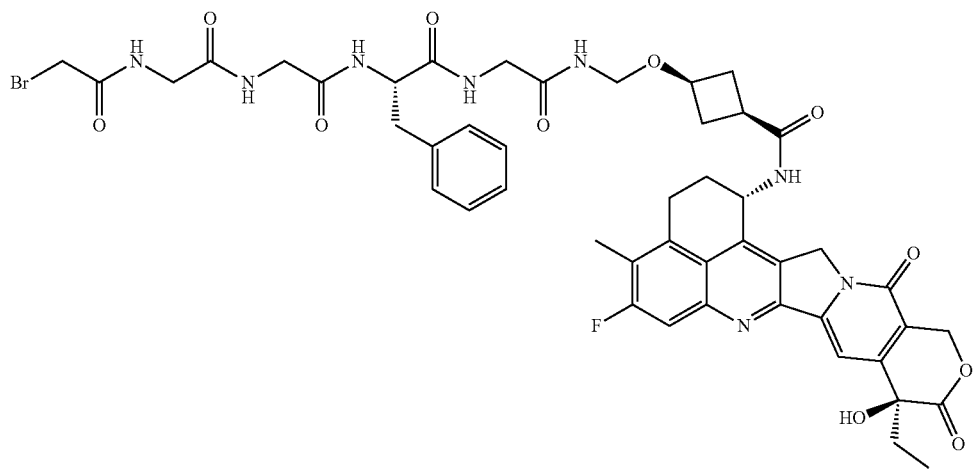

The protocol for the preparation of linker-payload X4 was as follows:

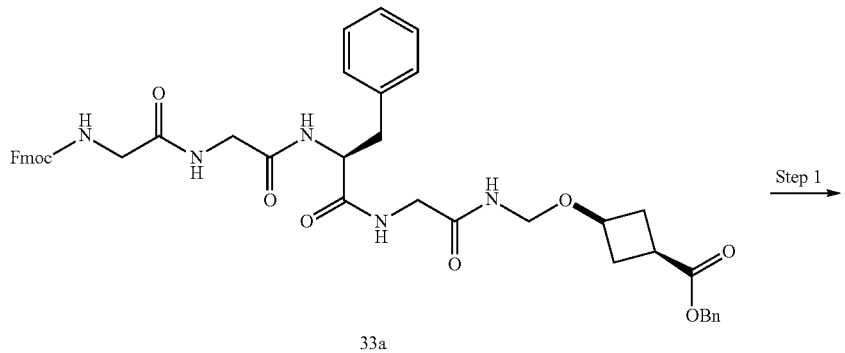

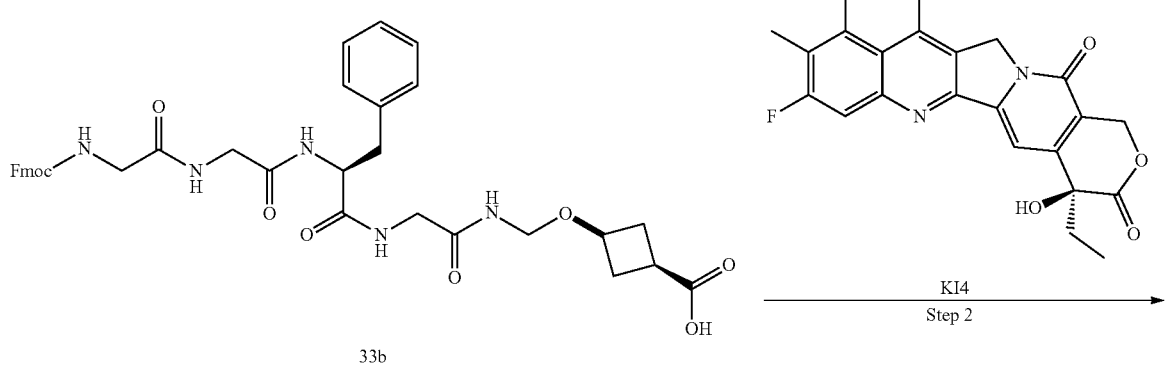

-continued
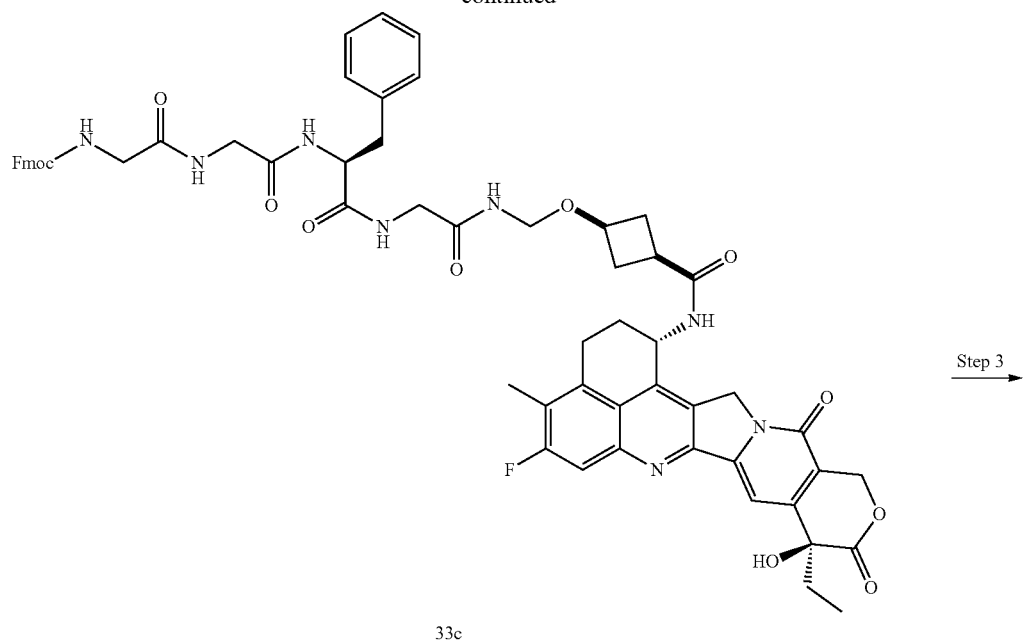
33c
Step 3
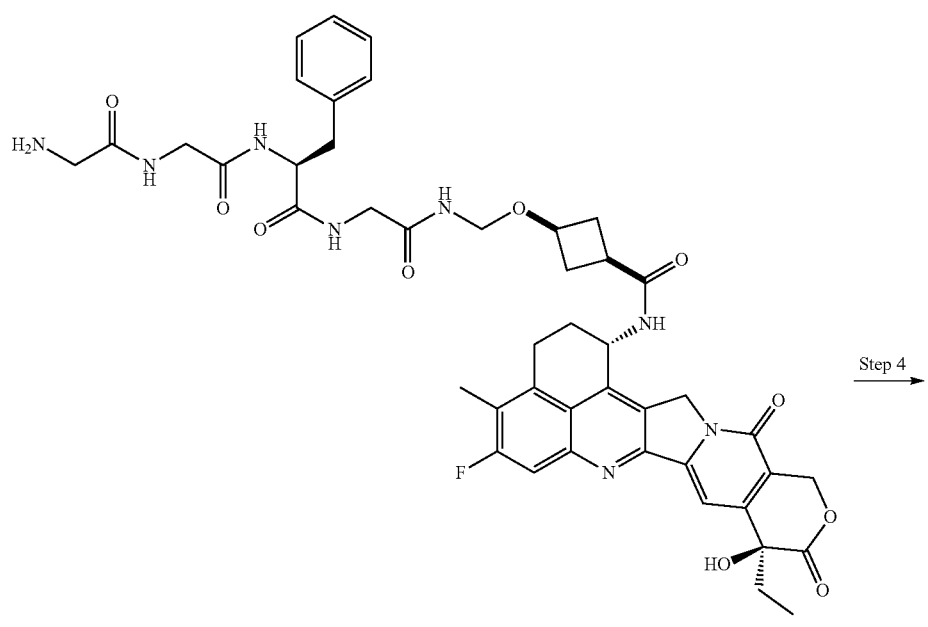
33d
Step 4

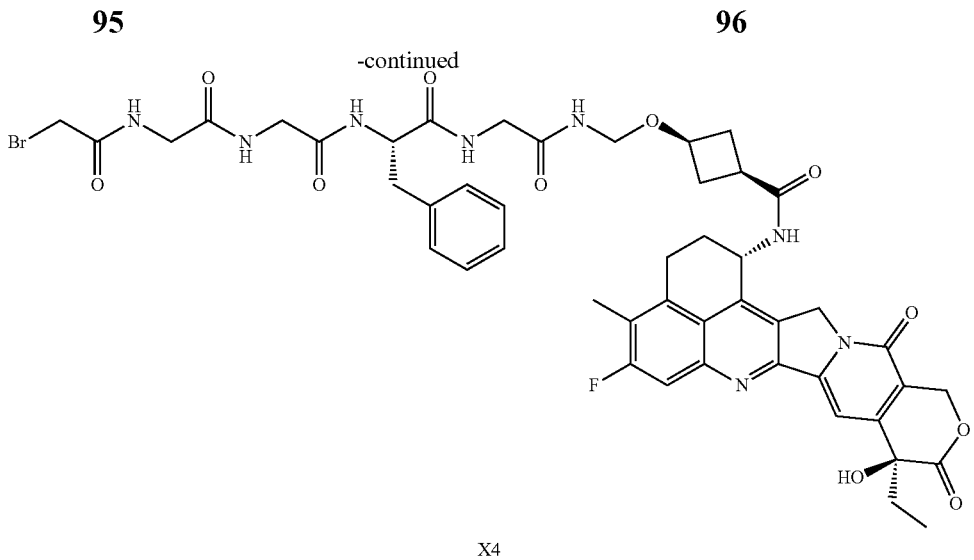

X4

Step 1

Pd/C (400 mg, 10 wt. %) was added to 33a (2.00 g, 2.58 mmol) in MeOH (20 mL), and the mixture was stirred at 20° C. for 5 h. After the reaction was completed as shown by TLC (EA), the reaction mixture was filtered, and the filtrate was concentrated to dryness by rotary evaporation to give 33b as a white solid (1.3 g, 74% yield).

Step 2

HATU (305 mg, 0.802 mmol) was added to 33b (0.55 g, 0.802 mmol), KI4 (427 mg, 0.802 mmol) and DIPEA (310 mg, 2.40 mmol) in DMF (5 mL), and the mixture was stirred at 0° C. for 2 h. After the reaction was completed as shown by TLC (DCM/MeOH=1/10), the reaction mixture was poured into water (40 mL). The resulting mixture was filtered, and the filter cake was purified by column chromatography (DCM/MeOH=20/1) to give 33c as a yellow solid (360 mg, 41% yield).

Step 3

Diethylamine (2 mL) was added to 33c (360 mg, 0.326 mmol) in DCM (10 mL), and the mixture was stirred at 25° C. for 17 h. After the reaction was completed as shown by TLC (DCM/MeOH=5/1), the reaction mixture was poured into PE (100 mL), and the resulting mixture was filtered to give 33d as a white solid (205 mg, 71% yield). MS-ESI: m/z 881.3 [M+H]+.

Step 4

A solution of bromoacetyl bromide (94 mg, 0.446 mmol) in THF (2 mL) was added to 33d (205 mg, 0.233 mmol) and triethylamine (118 mg, 1.17 mmol) in DMF (1 mL) and water (1 mL), and the mixture was stirred at 0° C. for 1 h. The reaction mixture was directly purified by preparative chromatography to give X4 as a white solid (15 mg, 6% yield).

MS-ESI: m/z 1001.2 [M+H]+.

1H NMR (400 MHz, DMSO-d6) δ 8.57-8.50 (m, 1H), 8.50-8.43 (m, 2H), 8.35-8.29 (m, 1H), 8.19-8.12 (m, 2H), 7.80 (d, J=10.8 Hz, 1H), 7.27-7.14 (m, 7H), 6.53 (s, 1H), 5.59-5.51 (m, 1H), 5.44-5.39 (m, 2H), 5.20-5.07 (m, 2H), 4.56-4.44 (m, 3H), 3.92 (s, 3H), 3.80-3.68 (m, 5H), 3.41 (s, 1H), 3.21-3.12 (m, 2H), 2.83-2.74 (m, 1H), 2.58-2.55 (m, 3H), 2.39 (s, 4H), 2.18-2.03 (m, 4H), 1.93-1.78 (m, 2H), 0.87 (t, J=7.3 Hz, 3H).

2.2. Preparation of Anti-B7H3 Antibody-Drug Conjugates 2.2.1. Preparation of reference ADC-1 (Daiichi Sankyo, DS7300)

DS-7300 is composed of a humanized anti-B7-H3 IgG1 monoclonal antibody conjugated to a topoisomerase I inhibitor payload, an exatecan derivative deruxtecan, via a tetrapeptide-based cleavable linker.

A reducing agent and a protective agent were formulated using ultrapure water: a 2 mg/mL aqueous solution of TCEP (tris-2-carboxyethyl-phosphine, manufacturer: Thermo) and a 100 mmol/L aqueous solution of EDTA (disodium ethylenediaminetetraacetate, manufacturer: Sigma).

Linker-payload (deruxtecan) was dissolved in anhydrous DMA (N,N-dimethylacetamide, manufacturer: Sinopharm) to prepare a 10 mg/mL solution of linker-payload in DMA.

16 mg of 7.4 mg/mL reference monoclonal antibody (the antibody sequence comprised a heavy chain set forth in sequence No. 9 and a light chain set forth in sequence No. 16 in the patent "CN104755494B"; the antibody was produced by transfection of CHO cells followed by routine antibody expression and purification, with >95% purity) was weighed into a 50 mL centrifuge tube and diluted to 5 mg/mL by adding 30 mM His-HAc, pH 5.5 buffer. The 100 mM aqueous solution of EDTA was added in an amount of 5% of the total volume of the reaction mixture, and the resulting mixture was well mixed by shaking. Then the antibody was reduced by adding the 2 mg/mL aqueous solution of TCEP in a TCEP-to-antibody molar ratio of 2.7:1, and the resulting mixture was well mixed by shaking and reacted on a cooling thermomixer at 37° C. for 2 h. The above solution of Linker-payload in DMA was added in a drug-to-antibody final concentration molar ratio of 9:1, and additional DMA was added in an amount of 10% of the total volume of the reaction mixture. The resulting mixture was well mixed by shaking and reacted on a cooling thermomixer at 4° C. for 1 h. Sample preservation buffer exchanges were performed using ultrafiltration tubes (MWCO 30 KD, manufacturer: Millipore). First, ultrafiltration was performed three times using a 30 mM His-HAc, pH 5.5 buffer containing 10% DMSO, then ultrafiltration was performed six times using a 30 mM DMSO-free His-HAc, pH 5.5 buffer, and finally, filtration was performed through a 0.2 μm PES membrane to remove bacteria to give an antibody-drug conjugate reference ADC-1 (11 mg, at a concentration of 5.825 mg/mL, 68.75% yield).

Tests showed that the antibody-drug conjugate reference ADC-1's drug loading (DAR) was 4.59 and the SEC purity was 99.64%.

2.2.2. Preparation of Antibody-Drug Conjugate WBP301088-X2

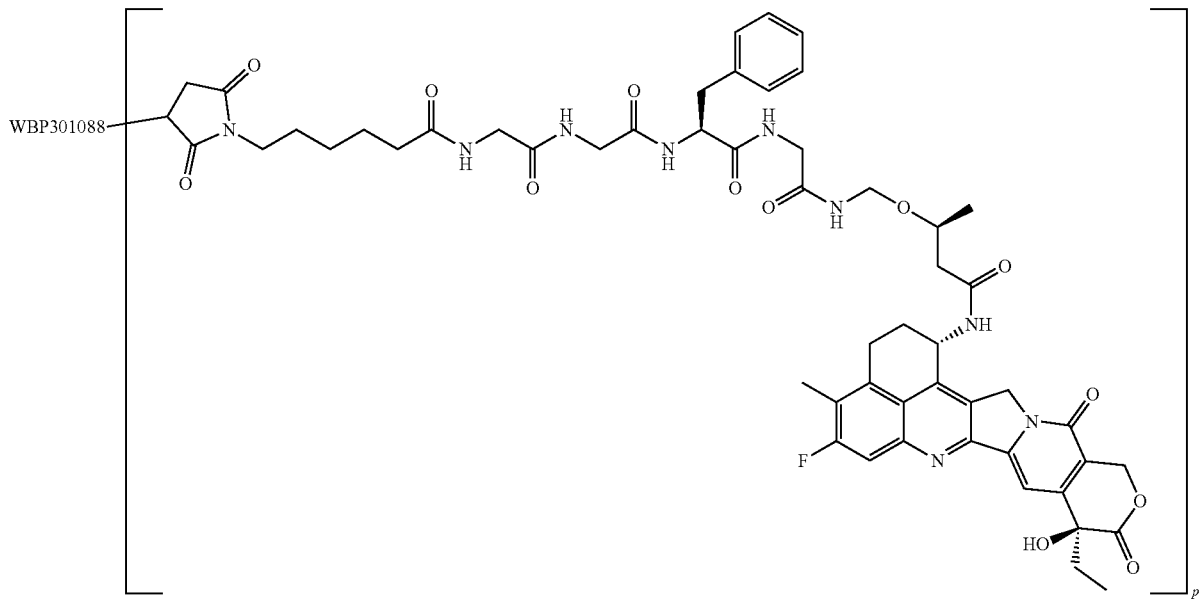

A reducing agent and a protective agent were formulated using ultrapure water: a 2 mg/mL aqueous solution of TCEP (tris-2-carboxyethyl-phosphine, manufacturer: Thermo) and a 100 mmol/L aqueous solution of EDTA (disodium ethylenediaminetetraacetate, manufacturer: Sigma).

Linker-payload X2 prepared in Example 2.1.2 was dissolved in anhydrous DMA (N,N-dimethylacetamide, manufacturer: Sinopharm) to prepare a 10 mg/mL solution of linker-payload in DMA.

1) An antibody-drug conjugate WBP301088-X2 (DAR4) was prepared as follows:
  20 mg of 11.3 mg/mL WBP301088 monoclonal antibody was weighed into a 50 mL centrifuge tube and diluted to 5 mg/mL by adding 30 mM His-HAc, pH 5.5 buffer. The 100 mM aqueous solution of EDTA was added in an amount of 5% of the total volume of the reaction mixture, and the resulting mixture was well mixed by shaking. Then the antibody was reduced by adding the 2 mg/mL aqueous solution of TCEP in a TCEP-to-antibody molar ratio of 4.5:1, and the resulting mixture was well mixed by shaking and reacted on a cooling thermomixer at 37° C. for 2 h. The above solution of Linker-payload in DMA was added in a drug-to-antibody final concentration molar ratio of 12:1, and additional DMA was added in an amount of 10% of the total volume of the reaction mixture. The resulting mixture was well mixed by shaking and reacted on a cooling thermomixer at 4° C. for 1 h. Sample preservation buffer exchanges were performed using ultrafiltration tubes (MWCO 30 KD, manufacturer: Millipore). First, ultrafiltration was performed three times using a 30 mM His-HAc, pH 5.5 buffer containing 10% DMSO, then ultrafiltration was performed six times using a 30 mM DMSO-free His-HAc, pH 5.5 buffer, and finally, filtration was performed through a 0.2 μm PES membrane to remove bacteria to give an antibody-drug conjugate WBP301088-X2 (DAR4) (15 mg, at a concentration of 7.162 mg/mL, 75% yield).

Tests showed that the antibody-drug conjugate WBP301088-X2 (DAR4)'s drug loading (DAR) was 4.02 and the SEC purity was 99.20%.

2) An antibody-drug conjugate WBP301088-X2 (DAR6) was prepared as follows:
  20 mg of 11.3 mg/mL WBP301088 monoclonal antibody was weighed into a 50 mL centrifuge tube and diluted to 5 mg/mL by adding 30 mM His-HAc, pH 5.5 buffer. The 100 mM aqueous solution of EDTA was added in an amount of 5% of the total volume of the reaction mixture, and the resulting mixture was well mixed by shaking. Then the antibody was reduced by adding the 2 mg/mL aqueous solution of TCEP in a TCEP-to-antibody molar ratio of 8:1, and the resulting mixture was well mixed by shaking and reacted on a cooling thermomixer at 37° C. for 2 h. The above solution of Linker-payload in DMA was added in a drug-to-antibody final concentration molar ratio of 12:1, and additional DMA was added in an amount of 10% of the total volume of the reaction mixture. The resulting mixture was well mixed by shaking and reacted on a cooling thermomixer at 4° C. for 1 h. Sample preservation buffer exchanges were performed using ultrafiltration tubes (MWCO 30 KD, manufacturer: Millipore). First, ultrafiltration was performed three times using a 30 mM His-HAc, pH 5.5 buffer containing 10% DMSO, then ultrafiltration was performed six times using a 30 mM DMSO-free His-HAc, pH 5.5 buffer, and finally, filtration was performed through a 0.2 μm PES membrane to remove bacteria to give an antibody-drug conjugate WBP301088-X2 (DAR6) (10.8 mg, at a concentration of 4.933 mg/mL, 54% yield).

Tests showed that the antibody-drug conjugate WBP301088-X2 (DAR6)'s drug loading (DAR) was 5.68 and the SEC purity was 99.57%.

3) An antibody-drug conjugate WBP301088-X2 (DAR8) was prepared as follows:

20 mg of 11.3 mg/mL WBP301088 monoclonal antibody was weighed into a 50 mL centrifuge tube and diluted to 5 mg/mL by adding 30 mM His-HAc, pH 5.5 buffer. The 100 mM aqueous solution of EDTA was added in an amount of 5% of the total volume of the reaction mixture, and the resulting mixture was well mixed by shaking. Then the antibody was reduced by adding the 2 mg/mL aqueous solution of TCEP in a TCEP-to-antibody molar ratio of 15:1, and the resulting mixture was well mixed by shaking and reacted on a cooling thermomixer at 37° C. for 2 h. The above solution of Linker-payload in DMA was added in a drug-to-antibody final concentration molar ratio of 18:1, and additional DMA was added in an amount of 10% of the total volume of the reaction mixture. The resulting mixture was well mixed by shaking and reacted on a cooling thermomixer at 4° C. for 1 h. Sample preservation buffer exchanges were performed using ultrafiltration tubes (MWCO 30 KD, manufacturer: Millipore). First, ultrafiltration was performed three times using a 30 mM His-HAc, pH 5.5 buffer containing 10% DMSO, then ultrafiltration was performed six times using a 30 mM DMSO-free His-HAc, pH 5.5 buffer, and finally, filtration was performed through a 0.2 μm PES membrane to remove bacteria to give an antibody-drug conjugate WBP301088-X2 (DAR8) (10.2 mg, at a concentration of 4.278 mg/mL, 51.0% yield).

Tests showed that the antibody-drug conjugate WBP301088-X2 (DAR8)'s drug loading (DAR) was 7.45 and the SEC purity was 98.73%.

2.3. Preparation of Cytotoxin (Payload)

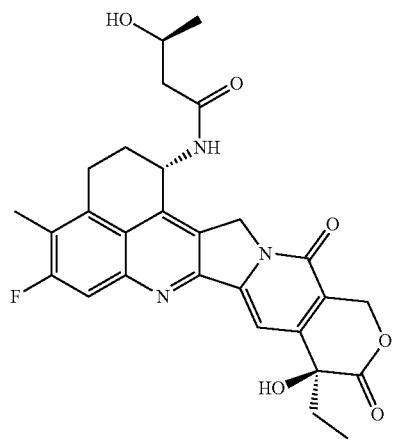

P-III-30

The protocol for the preparation of payload P-III-30 was as follows:

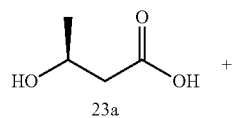

23a

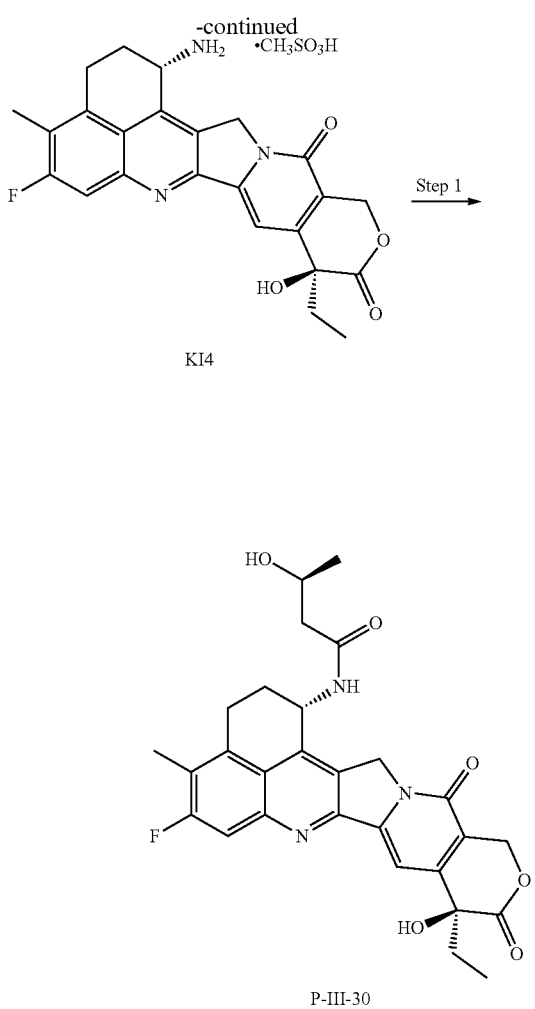

KI4

P-III-30

Step 1

DIEA (60.6 mg, 0.47 mmol) was added dropwise to a solution of KI4 (100 mg, 0.19 mmol), HATU (85.7 mg, 0.23 mmol) and 23a (21.5 mg, 0.21 mmol) in DMF (2 mL) under nitrogen, and after the addition, the mixture was reacted at 0° C. for 2 h. After the starting material was consumed completely as shown by LCMS, the reaction mixture was added dropwise to water (20 mL) and stirred, and a solid was precipitated. The resulting mixture was filtered to give P-III-30 as a gray solid (60.2 mg, 61% yield). MS-ESI: m/z 522.2 [M+H]+.

1H NMR (400 MHz, DMSO-d6) δ 8.42 (d, J=8.7 Hz, 1H), 7.79 (d, J=11.0 Hz, 1H), 7.30 (s, 1H), 6.53 (s, 1H), 5.62-5.53 (m, 1H), 5.42 (s, 2H), 5.30-5.16 (m, 2H), 4.63 (d, J=4.6 Hz, 1H), 4.09-3.99 (m, 1H), 3.22-3.11 (m, 2H), 2.40 (s, 3H), 2.28 (dd, J=13.7, 7.2 Hz, 1H), 2.22-2.08 (m, 3H), 1.94-1.78 (m, 2H), 1.08 (d, J=6.1 Hz, 3H), 0.87 (t, J=7.3 Hz, 3H).

2.4. Detection of Binding Activity of Antibody-Drug Conjugate and Unconjugated Antibody Thereof to Human B7H3 Antigen Based on ELISA In this example, whether there was a change in specific binding of the antibody to B7H3 antigen protein before and after conjugation to the drug was determined using ELISA. The information on the antigens and the test antibody used was as follows.

| Material | Supplier | Cat. No. | Batch No. |
|---|---|---|---|
| Human PD-L1, His Tag | ACRO | PD1-H5229 | 449-214EF1-142 |
| Human B7-H2, His Tag | ACRO | B72-H5221 | 741-71AF1-XX |
| Human B7-H3(4Ig), His Tag ("recombinant human B7H3 antigen" in this example) | ACRO | B7B-H52E7 | 2856C-2047F1-ZR |
| Human B7-H4 protein, His Tag | ACRO | B74-H5222 | 1042-21B5F1-123 |
| Human B7-H5, His Tag | ACRO | B75-H52H0 | 1760-20CAF1-ZL |
| Human B7-H6 | ACRO | B76-H52H8 | 2058b-89MF1-VD |
| Human B7-1 protein, His Tag | ACRO | B71-H5228 | 2408-209HF2-111 |
| Human B7-2 protein, His Tag | ACRO | CD6-H5223 | 743-208VF1-YH |
| Human PD-L2, His Tag (confirmed by SPR) | ACRO | PD2-H5220 | 1040-2143F1-W7 |
| Human B7-H7, His Tag | ACRO | B77-H52H5 | 2060b-219DF1-11B |
| Human BTNL2 protein, His Tag | AtaGenix | ATMP02212HU | 64306 |
| Anti-human IgG (Fab-specific)-peroxidase, antibody produced in goat | SIGMA | A0293 | 0000106803 |

2.4.1. Detection of Binding Activity Based on ELISA

A 96-well ELISA plate was coated with 2 µg/mL recombinant human B7H3 antigen (see the table above) at 30 µL/well and kept at 4° C. overnight. The following day, the well plate was washed 3 times with PBST and then blocked with 5% skim milk for 2 h. After the plate was washed 3 times with PBST, serially-diluted antibody WBP301088, antibody-drug conjugate WBP301088-X2 (DAR6), or isotype control antibody hIgG1 isotype was added and incubated for 1 h. The plate was then washed 3 times with PBST, and an HRP-labeled anti-human secondary antibody diluted in a 1:5000 ratio was then added at 100 µL/well and incubated for 1 h. After the incubation was complete, the plate was washed six times with PBST, and TMB (SurModics, TMBS-1000-01) was added for color development. Based on the results of the color development, the reaction was stopped by adding 2M HCl, and the plate was read by a microplate reader (Molecular Devices, SpecterMax 190) at OD450. The results are shown in FIG. 13, which indicate that there was no significant change in the binding activity of the antibody to the human B7H3 antigen protein before and after conjugation to the drug.

2.4.2. Detection of Binding Activity to B7 Family Proteins Based on ELISA

Human PD-L1 protein (see the table above), human B7-H2 protein, human B7-H3 protein, human B7-H4 protein, human B7-H5 protein, human B7-H6 protein, human B7-1 protein, human B7-2 protein, human PD-L2 protein, human B7-H7 protein, and human BTNL2 protein were separately immobilized on 96-well plates by incubation at 4° C. overnight. The 96-well plates were then blocked by incubation with 1% BSA in PBS at 37° C. for 1 h. After blocking, the 96-well plates were washed 3 times with PBST (PBS containing 0.05% Tween 20). Serially-diluted antibody WBP301088, antibody-drug conjugate WBP301088-X2 (DAR6), or isotype control antibody hIgG1 isotype was prepared in binding buffer (PBS containing 0.05% Tween 20 and 0.5% BSA) and incubated with the B7 family proteins immobilized on the 96-well plates at 37° C. for 1 h. After incubation, the 96-well plates were washed 3 times with PBST, incubated with a secondary antibody (see the table above) in binding buffer at 37° C. for 1 h, and then washed again. TMB was added for color development, and the reaction was stopped by 1 M $H_2SO_4$. The results are shown in FIG. 14.

Figure 14:
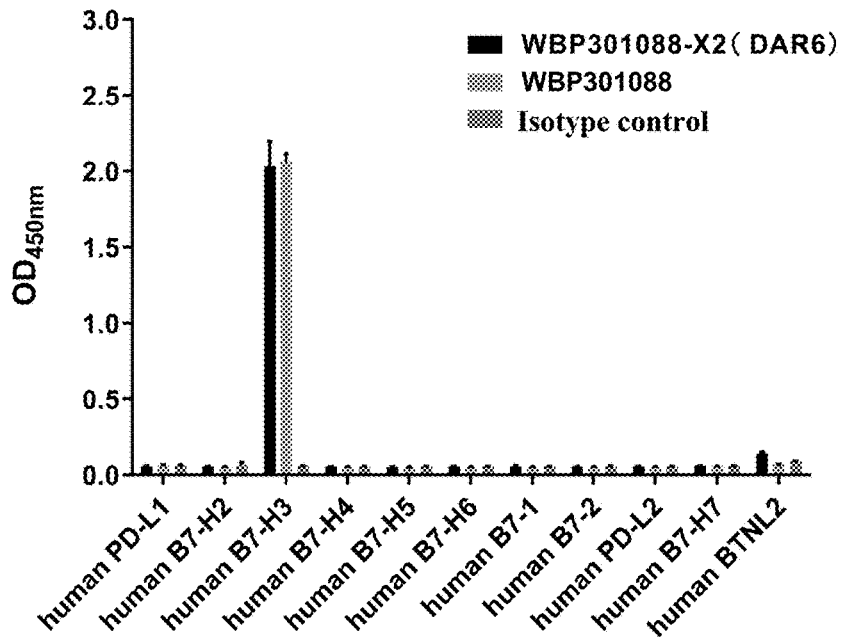
FIG. 14 shows detection of the binding of an antibody-drug conjugate and an unconjugated antibody thereof to each B7 family protein. In the figure, "WBP301088" represents the unconjugated antibody W301088-1.145.16-z3-p1-uIgG1KV320.

As can be seen from FIG. 14, there was no significant change in the binding activity of the antibody to the human B7H3 antigen protein before and after conjugation to the drug, and the antibody and the antibody-drug conjugate bound specifically only to the human B7-H3 and not to any of the other B7 family proteins.

Example 3. Test for Inhibitory Effect of Antibody-Drug Conjugates on in Vitro Tumor Cell Proliferation Anti-B7H3 ADC WBP301088-X2 (DAR6) and reference molecule ADC-1 were incubated with human tumor cells that positively expressed B7H3 for 7 days, and the inhibitory effect thereof on cell proliferation was assessed through a CellTiter-Glo® chemiluminescence cell viability assay (i.e., the CTG method).

Cells growing at log phase were collected and plated at a density of 1000-3000 cells/well, and the cell plate was incubated in a 37° C., 5% $CO_2$ incubator overnight. On day two of the experiment, after WBP301088-X2 (DAR6) was diluted 3-fold with a complete medium to obtain 9 concentration gradients (starting at the highest concentration of 1000 nM) of the drug, the drug was added to the cell culture plate at 50 µL/well. The complete medium was used as a blank control, and 3 replicate wells were set. The plate was incubated in the 37° C., 5% $CO_2$ incubator for another 5 days. After the incubation, the cell culture plate was taken out and equilibrated to room temperature. To each well, 50 µL of a CTG assay reagent was added, and after the mixtures were well mixed by shaking, the plate was let stand in the dark for 10 min. Then the signals were detected and their values were read using a microplate reader. A sigmoidal dose-response curve was plotted using a non-linear regression model in the GraphPad Prism software, and the $IC_{50}$ value was calculated. The cell viability was calculated as $(Lum_{test\ drug} - Lum_{blank\ control})/(Lum_{solvent\ blank\ control} - Lum_{blank\ control}) \times 100\%$.

The experimental results are shown in the table below, in which CAL-120 was derived from DSMZ and the other cell lines were derived from ATCC.

TABLE 17

Inhibitory activity of antibody-drug conjugates against human tumor cell proliferation

| Cell | Cell type | WBP301088-X2 ($IC_{50}$ (nM)) | Reference ADC-1 ($IC_{50}$ (nM)) |
|---|---|---|---|
| NCI-H1568 | Lung cancer | 4.8 | 32.8 |
| NCI-H358 | Lung cancer | 11.4 | 122.9 |
| Calu-6 | Lung cancer | 52.3 | 428.5 |
| MCF-7 | Breast cancer | 55.5 | 435.2 |

TABLE 17-continued

Inhibitory activity of antibody-drug conjugates
against human tumor cell proliferation

| Cell | Cell type | WBP301088-X2 ($IC_{50}$ (nM)) | Reference ADC-1 ($IC_{50}$ (nM)) |
|---|---|---|---|
| U87 MG | Brain cancer | 86.5 | 354.3 |
| HT-29 | Colorectal cancer | 446 | 1144 |
| A375 | Melanoma | 164.7 | 314.7 |
| A549 | Lung cancer | 369.3 | 378.5 |
| PC-3 | Prostate cancer | 180.8 | 958.9 |
| CAL-120 | Breast cancer | 268.8 | NA |

As can be seen from the results in Table 17, the antibody-drug conjugate WBP301088-X2 (DAR6) of the present application exhibited inhibitory activity against the proliferation of a variety of tumor cells that positively expressed B7H3, which was better than that of the reference ADC-1.

Example 4. Evaluation of Efficacy of Antibody-Drug Conjugates in Mice Bearing Calu-6 Human Lung Cancer Cell Tumors To investigate the inhibitory effect of WBP301088-X2 (DAR6) on in vivo tumor formation, xenograft tumors were formed in mice using Calu-6 human lung cancer cells that positively expressed B7H3, and then the in vivo anti-tumor effect of WBP301088-X2 (DAR6) was evaluated.

6- to 8-week-old female BALB/c Nude mice (purchased from Zhejiang Vital River Laboratory Animal Technology Co., Ltd.) were used as test animals. $10 \times 10^6$ Calu-6 lung cancer cells were inoculated subcutaneously into the right dorsa of 6- to 8-week-old female BALB/c Nude mice. The growth of tumors in mice was observed. When the volume of the tumors reached about 139 mm³, the tumor-bearing mice were randomized into groups with 6 mice in each of the blank control group and the treatment groups. Intravenous (i.v.) injection of WBP301088-X2 or reference ADC-1 was administered on the day of grouping (day 0), and a total of one injection was administered. Doses administered were 1 mg/kg and 3 mg/kg. The experiment ended on day 28. Experimental grouping and dosing were as follows. The tumor volume and weight of mice were measured twice a week, and the data were recorded.

Blank control (negative control group): normal saline
WBP301088-X2 (treatment group): 1 mg/kg
WBP301088-X2 (treatment group): 3 mg/kg
Reference ADC-1 (treatment group, positive control group): 1 mg/kg
Reference ADC-1 (treatment group, positive control group): 3 mg/kg All samples were prepared by dilution with normal saline.

At the end of the experiment, mice were euthanized and tumor inhibition rate TGI was calculated as follows:

$$TGI(\%) = [1 - (T_i - T_0)/(V_i - V_0)] \times 100$$

$T_i$: mean tumor volumes of the treatment groups and the positive control group on day i of administration;

$T_0$: mean tumor volumes of the treatment groups and the positive control group on day 0 of administration;

$V_i$: mean tumor volume of the negative control group on day i of administration;

$V_0$: mean tumor volume of the negative control group on day 0 of administration.

Figure 15:
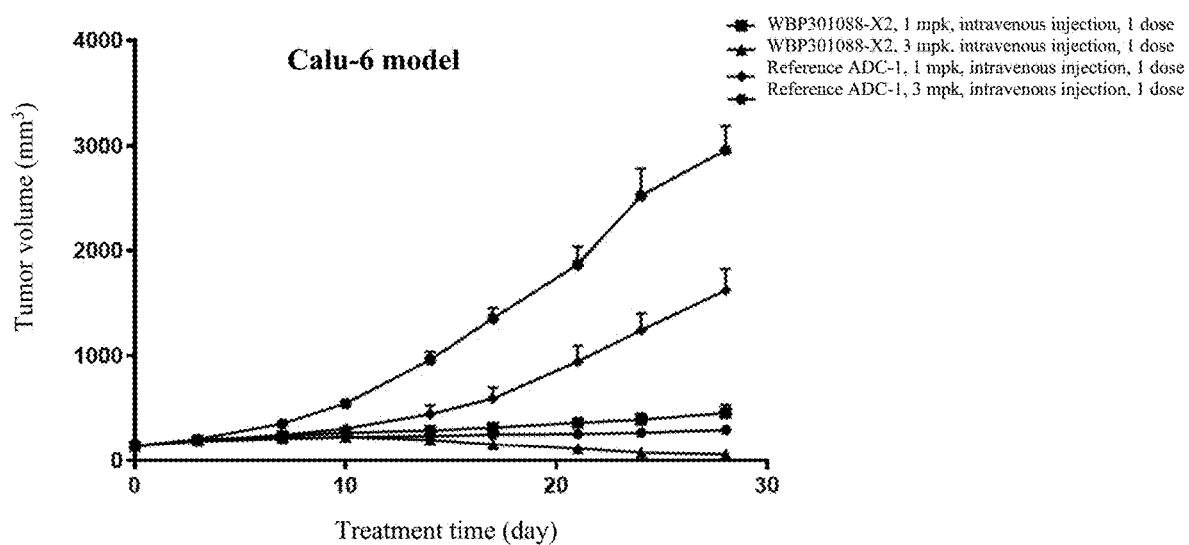
FIG. 15 shows evaluation of the efficacy of antibody-drug conjugates in Calu-6 tumor-bearing mice.

The experimental results are shown in FIG. 15, Table 18 and Table 19.

TABLE 18

The tumor volume (mm³) of each group at different time points

| | Group | | | | |
|---|---|---|---|---|---|
| Days (day) | 1 Blank control Tumor volume (mm³) | 2 Reference ADC-1, 1 mg/kg Tumor volume (mm³) | 3 Reference ADC-1, 3 mg/kg Tumor volume (mm³) | 4 WBP301088-X2, 1 mg/kg Tumor volume (mm³) | 5 WBP301088-X2, 3 mg/kg Tumor volume (mm³) |
| 0 | 139 ± 10 | 139 ± 14 | 139 ± 16 | 140 ± 14 | 140 ± 20 |
| 3 | 207 ± 18 | 195 ± 20 | 184 ± 20 | 196 ± 17 | 192 ± 27 |
| 7 | 355 ± 27 | 245 ± 28 | 210 ± 23 | 238 ± 21 | 219 ± 28 |
| 10 | 547 ± 44 | 309 ± 44 | 225 ± 27 | 267 ± 22 | 227 ± 30 |
| 14 | 963 ± 74 | 446 ± 82 | 237 ± 29 | 290 ± 29 | 198 ± 22 |
| 17 | 1357 ± 97 | 595 ± 103 | 252 ± 31 | 317 ± 35 | 156 ± 15 |
| 21 | 1866 ± 169 | 946 ± 151 | 254 ± 28 | 363 ± 47 | 116 ± 3 |
| 24 | 2521 ± 257 | 1241 ± 160 | 267 ± 32 | 394 ± 56 | 75 ± 9 |
| 28 | 2956 ± 233 | 1623 ± 201 | 296 ± 37 | 457 ± 76 | 61 ± 9 |

Notes:
tumor volumes are expressed as means ± standard errors; days are the number of days from administration.

TABLE 19

Evaluation of anti-tumor efficacy of test antibody-drug conjugates in Calu-6 cell subcutaneous xenograft tumor-bearing mouse model (calculations based on tumor volumes on day 24 after administration)

| Group | Tumor volume (mm³) (day 24) | T/C (%) | TGI (%) | p value |
|---|---|---|---|---|
| Blank control | 2521 ± 257 | — | — | — |
| Reference ADC-1, 1 mg/kg | 1241 ± 160 | 49.25 | 53.72 | 0.056 |
| Reference ADC-1, 3 mg/kg | 267 ± 32 | 10.61 | 94.62 | 0.005 |
| WBP301088-X2, 1 mg/kg | 394 ± 56 | 15.61 | 89.37 | 0.005 |
| WBP301088-X2, 3 mg/kg | 75 ± 9 | 2.99 | 102.73 | 0.003 |

Notes:
tumor volumes are expressed as means ± standard errors; tumor growth inhibition was reflected by T/C (T/C (%) = $T_i/V_i \times 100$) and TGI (TGI (%) = $[1 - (T_i - T_0)/(V_i - V_0)] \times 100$); and p values were calculated from tumor volumes (p > 0.05 indicates no statistical difference, and p < 0.01 indicates a significant difference).

The results in FIG. 15, Table 18 and Table 19 indicate that the antibody-drug conjugate WBP301088-X2 of the present application showed significant dose-dependent anti-tumor activity after the administration of a single dose and its anti-tumor effect was significantly better than that of reference ADC-1 at both the dose of 1 mg/kg and the dose of 3 mg/kg.

Example 5. Evaluation of Efficacy of Antibody-Drug Conjugates in Mice Bearing A375 Human Melanoma Cell Tumors To investigate the inhibitory effect of WBP301088-X2 (DAR6) on in vivo tumor formation, xenograft tumors were formed in mice using A375 human melanoma cells that positively expressed B7H3, and then the in vivo anti-tumor effect of WBP301088-X2 (DAR6) was evaluated.

6- to 8-week-old female NOD/SCID mice (purchased from Jiangsu GemPharmatech Co., Ltd.) were used as test animals. $5 \times 10^6$ A375 human melanoma cells were inoculated subcutaneously into the right dorsa of 6- to 8-week-old female NOD/SCID mice. The growth of tumors was observed. When the volume of the tumors reached about 89 mm³, the tumor-bearing mice were randomized into groups with 6 mice in each of the blank control group and the treatment groups. Intravenous (i.v.) injection of WBP301088-X2 or reference ADC-1 was administered on the day of grouping (day 0), and a total of one injection was administered. Doses administered were 1 mg/kg, 3 mg/kg and 10 mg/kg. The experiment ended on day 20. The tumor volume and weight of mice were measured twice a week, and the data were recorded.

Blank control (negative control group): normal saline
WBP301088-X2 (treatment group): 1 mg/kg
WBP301088-X2 (treatment group): 3 mg/kg
WBP301088-X2 (treatment group): 10 mg/kg
Reference ADC-1 (treatment group): 3 mg/kg
Reference ADC-1 (treatment group): 10 mg/kg All samples were prepared by dilution with normal saline.

At the end of the experiment, mice were euthanized and $TGI_{TV}$ (relative tumor inhibition rate) was calculated. The $TGI_{TV}$ (relative tumor inhibition rate) was calculated by the following formula:

$$TGI_{TV} = \left(1 - \frac{\text{mean } RTV_{treat}}{\text{mean } RTV_{vehicle}}\right) \times 100\%$$

wherein, mean $RTV_{treat}$: mean RTV of dosing group;
mean $RTV_{vehicle}$: mean RTV of vehicle group (in this example, the vehicle group is the group in which only normal saline was administered);
The RTV was calculated by the following formula:

$$RTV_n = \frac{V_{nt}}{V_{n0}}$$

wherein, $V_{nt}$: tumor volume in n-numbered mouse on day t;
$V_{n0}$: tumor volume in n-numbered mouse on day 0;
$RTV_n$: relative tumor volume in n-numbered mouse on day t.

Figure 16:
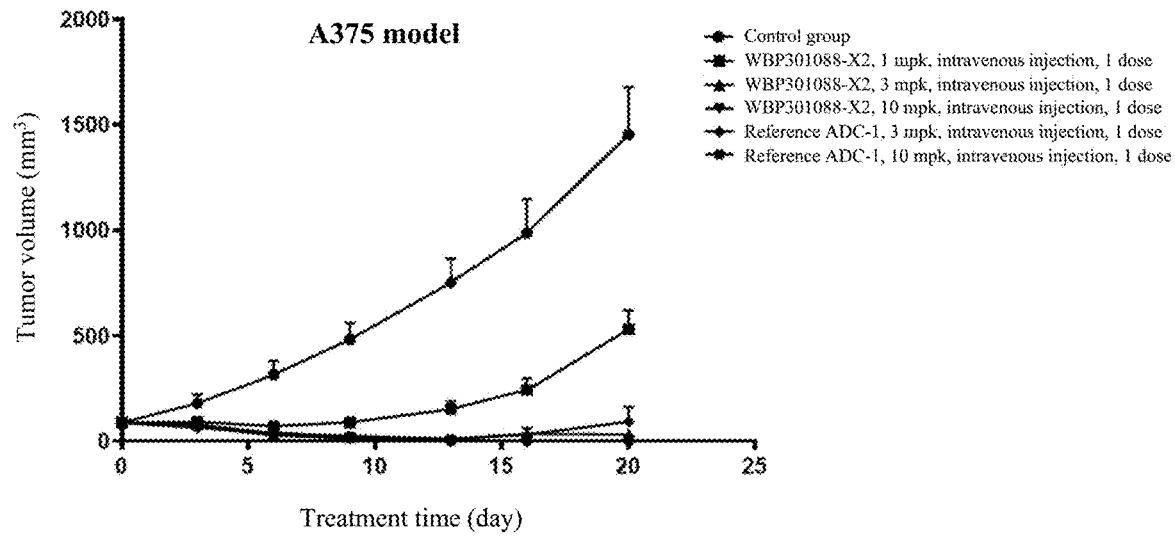
FIG. 16 shows evaluation of the efficacy of antibody-drug conjugates in A375 tumor-bearing mice.

The experimental results are shown in FIG. 16, Table 20 and Table 21.

TABLE 20

Changes in tumor volume in different groups

| Group | Tumor volume (mm³) | | | | | | |
|---|---|---|---|---|---|---|---|
| | D 0 | D 3 | D 6 | D 9 | D 13 | D 16 | D 20 |
| Blank control | 88.55 ± 9.79 | 179.90 ± 40.56 | 317.78 ± 66.27 | 484.12 ± 77.65 | 753.85 ± 112.97 | 987.29 ± 159.48 | 1453.17 ± 226.44 |
| WBP301088-X2, 1 mpk | 88.92 ± 8.64 | 91.83 ± 5.88 | 71.71 ± 11.17 | 89.8 ± 17 | 152.36 ± 36.98 | 244.50 ± 55.84 | 533.31 ± 87.51 |
| WBP301088-X2, 3 mpk | 88.77 ± 9.27 | 78.50 ± 20.22 | 36.83 ± 9.16 | 17.21 ± 6.87 | 9.25 ± 6.46 | 35.24 ± 26.23 | 32.16 ± 22.79 |
| WBP301088-X2, 10 mpk | 88.87 ± 9.18 | 69.55 ± 11.66 | 27.76 ± 4.21 | 14.4 ± 1.39 | 1.08 ± 1.08 | 0.00 ± 0.00 | 0.00 ± 0.00 |
| Reference ADC-1, 3 mpk | 88.67 ± 8.85 | 64.19 ± 8.68 | 40.14 ± 10.24 | 24.81 ± 7.51 | 11.04 ± 4.20 | 31.20 ± 18.76 | 93.10 ± 68.47 |
| Reference ADC-1, 10 mpk | 88.89 ± 8.57 | 78.21 ± 12.7 | 29.82 ± 4.55 | 16.94 ± 2.89 | 2.37 ± 1.55 | 0.00 ± 0.00 | 0.00 ± 0.00 |

Note:
data are expressed as means ± standard errors.

TABLE 21

Relative tumor inhibition rates ($TGI_{TV}$) in different groups

| Group | D 0 | D 3 | D 6 | D 9 | D 13 | D 16 | D 20 |
|---|---|---|---|---|---|---|---|
| WBP301088-X2 1 mpk | 0.00% | 45.31% | 75.46% | 80.52% | 79.33% | 74.28% | 62.21% |
| WBP301088-X2 3 mpk | 0.00% | 55.27% | 88.25% | 96.69% | 98.95% | 96.22% | 98.17% |
| WBP301088-X2 10 mpk | 0.00% | 59.93% | 90.91% | 96.91% | 99.89% | 100.00% | 100.00% |
| Reference ADC-1 3 mpk | 0.00% | 62.43% | 87.68% | 95.00% | 98.56% | 97.13% | 94.69% |

TABLE 21-continued

| | Relative tumor inhibition rates ($TGI_{TV}$) in different groups | | | | | | |
|---|---|---|---|---|---|---|---|
| Group | D 0 | D 3 | D 6 | D 9 | D 13 | D 16 | D 20 |
| Reference ADC-1 10 mpk | 0.00% | 55.14% | 90.28% | 96.51% | 99.75% | 100.00% | 100.00% |

The results in FIG. 16, Table 20 and Table 21 indicate that the antibody-drug conjugate WBP301088-X2 of the present application showed significant dose-dependent anti-tumor activity after the administration of a single dose.

Example 6. Evaluation of Efficacy of Antibody-Drug Conjugates in Mice Bearing U87 Human Brain Cancer Cell Tumors To investigate the inhibitory effect of WBP301088-X2 (DAR6) on in vivo tumor formation, xenograft tumors were formed in mice using U87 human brain cancer cells that positively expressed B7H3, and then the in vivo anti-tumor effect of WBP301088-X2 (DAR6) was evaluated.

6- to 8-week-old female NCG mice (purchased from Jiangsu GemPharmatech Co., Ltd.) were used as test animals. 5×10$^6$ U87 human brain cancer cells were inoculated subcutaneously into the right sides of the necks or dorsa of 6- to 8-week-old female NCG mice. The growth of tumors in mice was observed. When the volume of the tumors reached about 187 mm$^3$, the tumor-bearing mice were randomized into groups with 6 mice in each of the blank control group and the treatment groups. Intravenous (i.v.) injection of WBP301088-X2 or reference ADC-1 was administered on the day of grouping (day 0), and a total of one injection was administered. Doses administered were 1 mg/kg and 3 mg/kg. The experiment ended on day 20. Experimental grouping and dosing were as follows. The tumor volume and weight of mice were measured twice a week, and the data were recorded.

Blank control (negative control group): normal saline
WBP301088-X2 (treatment group): 1 mg/kg
WBP301088-X2 (treatment group): 3 mg/kg
Reference ADC-1 (treatment group, positive control group): 1 mg/kg
Reference ADC-1 (treatment group, positive control group): 3 mg/kg All samples were prepared by dilution with normal saline.

At the end of the experiment, mice were euthanized and tumor inhibition rate TGI was calculated as follows:

$$TGI(\%) = [1-(T_i-T_0)/(V_i-V_0)] \times 100$$

$T_i$: mean tumor volumes of the treatment groups and the positive control group on day i of administration;

$T_0$: mean tumor volumes of the treatment groups and the positive control group on day 0 of administration;

$V_i$: mean tumor volume of the negative control group on day i of administration;

$V_0$: mean tumor volume of the negative control group on day 0 of administration.

Figure 17:
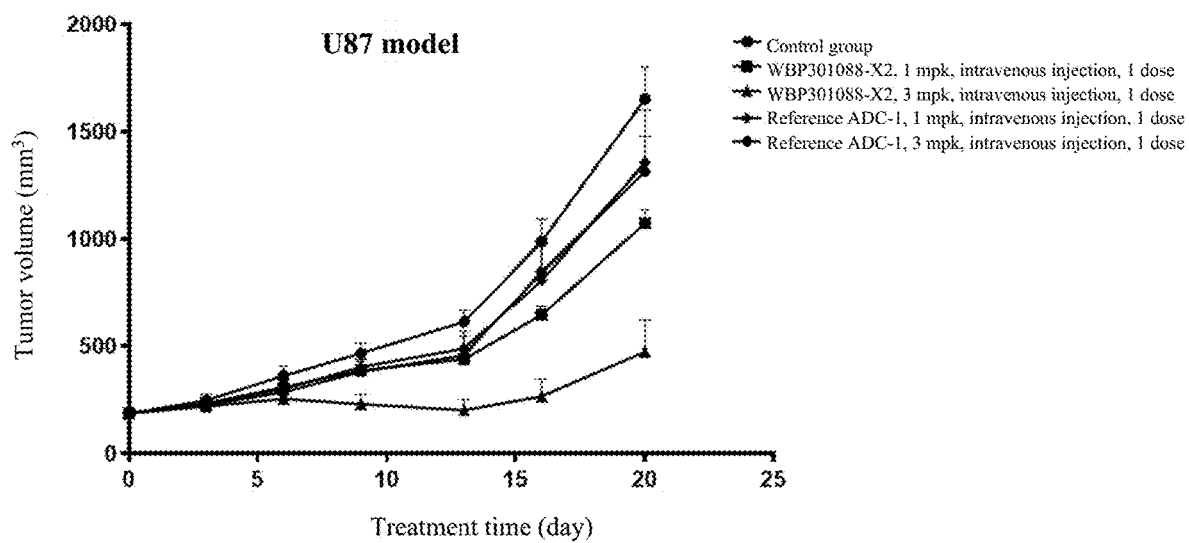
FIG. 17 shows evaluation of the efficacy of antibody-drug conjugates in U87 tumor-bearing mice.

The experimental results are shown in FIG. 17, Table 22 and Table 23.

TABLE 22

The tumor volume (mm$^3$) of each group at different time points

| | | Days | | | | | | |
|---|---|---|---|---|---|---|---|---|
| Group | | Day 0 | Day 3 | Day 6 | Day 9 | Day 13 | Day 16 | Day 20 |
| 1 | Blank control | 188 ± 25 | 247 ± 29 | 362 ± 46 | 466 ± 47 | 614 ± 54 | 988 ± 105 | 1651 ± 149 |
| 2 | Reference ADC-1 1 mg/kg Tumor volume (mm$^3$) | 187 ± 25 | 231 ± 31 | 301 ± 42 | 403 ± 61 | 489 ± 80 | 808 ± 171 | 1355 ± 247 |
| 3 | Reference ADC-1 3 mg/kg Tumor volume (mm$^3$) | 187 ± 22 | 226 ± 25 | 285 ± 36 | 381 ± 57 | 457 ± 90 | 846 ± 137 | 1314 ± 162 |
| 4 | WBP301088-X2 1 mg/kg Tumor volume (mm$^3$) | 187 ± 25 | 234 ± 27 | 308 ± 49 | 387 ± 42 | 439 ± 51 | 646 ± 42 | 1074 ± 64 |
| 5 | WBP301088-X2 3 mg/kg Tumor volume (mm$^3$) | 188 ± 20 | 220 ± 25 | 254 ± 43 | 231 ± 45 | 202 ± 49 | 266 ± 80 | 474 ± 148 |

Notes:
tumor volumes are expressed as means ± standard errors; days are the number of days from administration.

TABLE 23

Evaluation of anti-tumor efficacy of test antibody-drug conjugates in U87 MG cell subcutaneous xenograft tumor-bearing mouse model (calculations based on tumor volumes on day 20 after administration)

| Group | Tumor volume (mm$^3$) (day 20) | T/C (%) | TGI (%) | p value |
|---|---|---|---|---|
| Blank control | 1651 ± 149 | — | — | — |
| Reference ADC-1, 1 mg/kg | 1355 ± 247 | 82.08 | 20.21 | 0.969 |
| Reference ADC-1, 3 mg/kg | 1314 ± 162 | 79.63 | 22.96 | 0.819 |
| WBP301088-X2, 1 mg/kg | 1074 ± 64 | 65.06 | 39.40 | 0.138 |
| WBP301088-X2, 3 mg/kg | 474 ± 148 | 28.70 | 80.49 | 0.008 |

Notes:
tumor volumes are expressed as means ± standard errors; tumor growth inhibition was reflected by T/C (T/C (%) = $T_i/V_i$ × 100) and TGI (TGI (%) = [1 − ($T_i$ − $T_0$)/($V_i$ − $V_0$)] × 100); and p values were calculated from tumor volumes (p > 0.05 indicates no statistical difference, and p < 0.01 indicates a significant difference).

The results in FIG. 17, Table 22 and Table 23 indicate that the antibody-drug conjugate WBP301088-X2 of the present application showed significant dose-dependent anti-tumor activity after the administration of a single dose and the anti-tumor effect of the antibody-drug conjugate WBP301088-X2 was significantly better than that of reference ADC-1 at the dose of 3 mg/kg.

Example 7. Evaluation of Efficacy of Antibody-Drug Conjugates in Mice Bearing PC-3 Human Prostate Cancer Cell Tumors To investigate the inhibitory effect of WBP301088-X2 (DAR6) on in vivo tumor formation, xenograft tumors were formed in mice using PC-3 human prostate cancer cells that positively expressed B7H3, and then the in vivo anti-tumor effect of WBP301088-X2 (DAR6) was evaluated.

6- to 8-week-old female BALB/c Nude mice (purchased from Zhejiang Vital River Laboratory Animal Technology Co., Ltd.) were used as test animals. $5 \times 10^6$ PC-3 human prostate cancer cells were inoculated subcutaneously into the right sides of the necks or dorsa of 6- to 8-week-old female BALB/c Nude mice. The growth of tumors was observed. When the volume of the tumors reached about 155 mm$^3$, the tumor-bearing mice were randomized into groups with 6 mice in each of the blank control group and the treatment groups. Intravenous (i.v.) injection of WBP301088-X2 or reference ADC-1 was administered on the day of grouping (day 0), and a total of one injection was administered. Doses administered were 2 mg/kg and 6 mg/kg. The experiment ended on day 21. Experimental grouping and dosing were as follows. The tumor volume and weight of mice were measured twice a week, and the data were recorded.

Blank control (negative control group): normal saline
WBP301088-X2 (treatment group): 2 mg/kg
WBP301088-X2 (treatment group): 6 mg/kg
Reference ADC-1 (treatment group, positive control group): 2 mg/kg
Reference ADC-1 (treatment group, positive control group): 6 mg/kg All samples were prepared by dilution with normal saline.
At the end of the experiment, mice were euthanized and tumor inhibition rate TGI was calculated as follows:

$$TGI(\%) = [1 - (T_i - T_0)/(V_i - V_0)] \times 100$$

$T_i$: mean tumor volumes of the treatment groups and the positive control group on day i of administration;
$T_0$: mean tumor volumes of the treatment groups and the positive control group on day 0 of administration;
$V_i$: mean tumor volume of the negative control group on day i of administration;
$V_0$: mean tumor volume of the negative control group on day 0 of administration.

Figure 18:
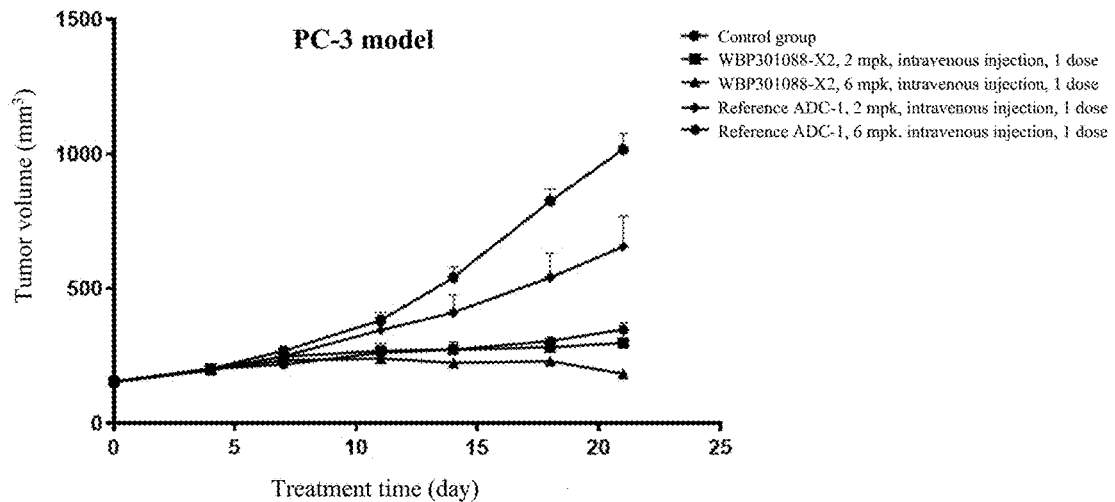
FIG. 18 shows evaluation of the efficacy of antibody-drug conjugates in PC-3 tumor-bearing mice.

The experimental results are shown in FIG. 18, Table 24 and Table 25.

TABLE 24

The tumor volume (mm$^3$) of each group at different time points

| Group | | Days | | | | | | |
|---|---|---|---|---|---|---|---|---|
| | | 0 | 4 | 7 | 11 | 14 | 18 | 21 |
| 1 | Blank control Tumor volume (mm$^3$) | 154 ± 8 | 202 ± 10 | 269 ± 14 | 382 ± 29 | 540 ± 40 | 826 ± 44 | 1017 ± 59 |
| 2 | Reference ADC-1, 2 mg/kg Tumor volume (mm$^3$) | 154 ± 7 | 196 ± 10 | 249 ± 17 | 346 ± 45 | 410 ± 65 | 540 ± 91 | 655 ± 115 |
| 3 | Reference ADC-1, 6 mg/kg Tumor volume (mm$^3$) | 154 ± 6 | 203 ± 9 | 218 ± 12 | 262 ± 12 | 273 ± 14 | 305 ± 16 | 349 ± 23 |
| 4 | WBP301088-X2, 2 mg/kg Tumor volume (mm$^3$) | 155 ± 7 | 202 ± 8 | 248 ± 23 | 268 ± 27 | 274 ± 28 | 282 ± 32 | 298 ± 37 |
| 5 | WBP301088-X2, 6 mg/kg Tumor volume (mm$^3$) | 155 ± 9 | 199 ± 11 | 233 ± 6 | 241 ± 6 | 225 ± 14 | 231 ± 15 | 184 ± 11 |

Notes:

tumor volumes are expressed as means ± standard errors; days are the number of days from administration.

TABLE 25

Evaluation of anti-tumor efficacy of test antibody-drug conjugates in PC-3 cell subcutaneous xenograft tumor-bearing mouse model (calculations based on tumor volumes on day 21 after administration)

| Group | Tumor volume (mm$^3$) (day 21) | T/C (%) | TGI (%) | p value |
|---|---|---|---|---|
| Vehicle | 1017 ± 59 | — | — | — |
| Reference ADC-1, 2 mg/kg | 655 ± 115 | 64.40 | 41.96 | <0.001 |
| Reference ADC-1, 6 mg/kg | 349 ± 23 | 34.26 | 77.46 | <0.001 |
| WBP301088-X2, 2 mg/kg | 298 ± 37 | 29.30 | 83.41 | <0.001 |
| WBP301088-X2, 6 mg/kg | 184 ± 11 | 18.06 | 96.62 | <0.001 |

Notes:
tumor volumes are expressed as means ± standard errors; tumor growth inhibition was reflected by T/C (T/C (%) = $T_i/V_i$ × 100) and TGI (TGI (%) = [1 − ($T_i$ − $T_0$)/($V_i$ − $V_0$)] × 100); and p values were calculated from tumor volumes (p > 0.05 indicates no statistical difference, and p < 0.01 indicates a significant difference).

The results in FIG. 18, Table 24 and Table 25 indicate that the antibody-drug conjugate WBP301088-X2 of the present application showed significant dose-dependent anti-tumor activity after the administration of a single dose and its anti-tumor effect was significantly better than that of reference ADC-1 at both the dose of 2 mg/kg and the dose of 6 mg/kg.

Example 8. Evaluation of Efficacy of Antibody-Drug Conjugate in Prostate Cancer Patient-Derived Xenograft (PDX) Model To investigate the efficacy of WBP301088-X2 (DAR6) in a prostate cancer patient-derived xenograft model, patient-derived prostate cancer PR9586 and PR9587 tumor tissues (obtained from Crown Biotechnology (Zhongshan) Co., Ltd.) was subcutaneously xenografted into NPG and NOG male mice, and the anti-tumor effect of WBP301088-X2 (DAR6) was evaluated.
1. Test compounds and materials
Blank control (control group): normal saline
WBP301088-X2 (treatment group): 10 mg/kg
2. Preparation method for test compounds: all samples were prepared by dilution with normal saline.
3. Experimental animals: NPG mice were purchased from Beijing Vitalstar Biotechnology Co., Ltd., and NOG mice were purchased from Beijing Vital River Laboratory Animal Technology Co., Ltd.
4. Procedures:
Patient-derived prostate cancer PR9586 and PR9587 tumor tissues were separately inoculated subcutaneously into NPG or NOG mice. When the tumors grew to about 500-800 mm$^3$, the tumor tissues were collected and the mice were euthanized. The collected tumor tissues were cut into tumor masses of a diameter of 2-3 mm and then inoculated subcutaneously into the right anterior scapula of the NPG or NOG mice. When the mean tumor volume of the tumor mass-inoculated NPG or NOG mice reached about 100-200 mm$^3$, the mice were randomized into groups with 6 mice in each of the blank control group and the treatment group.

Intravenous (i.v.) injection of WBP301088-X2 was administered on the day of grouping (day 0), the administration was performed once every two weeks for a total of two injections at a single dose of 10 mg/kg. The experiment ended on day 25 (for mice inoculated with PR9586) or on day 48 (for mice inoculated with PR9587). After the administration was started, the body weight and tumor size of the mice were measured twice a week. Calculation formula for tumor volume: Tumor volume (mm$^3$)=1/2×(a×b$^2$) (where a represents long diameter and b represents short diameter).

Figure 19A:
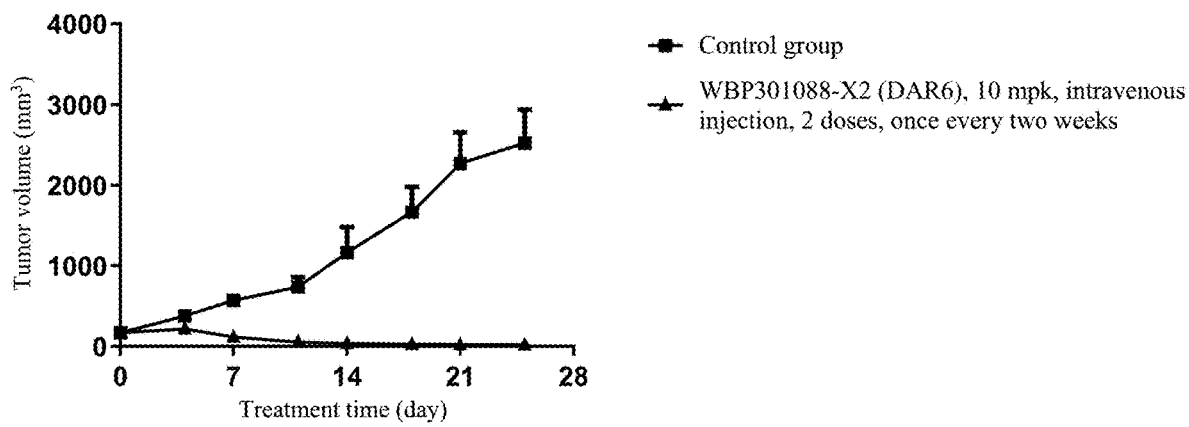
FIGS. 19A and 19B show evaluation of the efficacy of an antibody-drug conjugate in a prostate cancer patient-derived xenograft model.
Figure 19B:
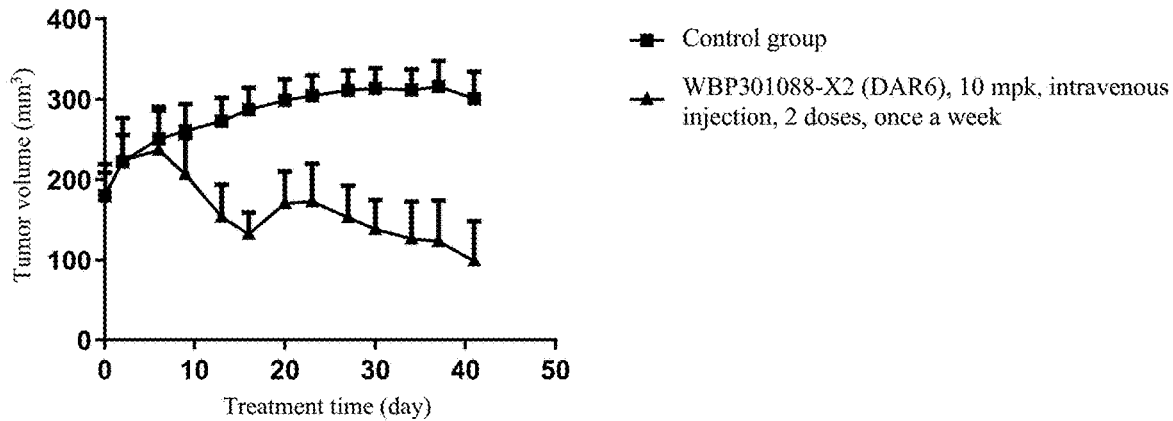

At the end of the experiment, mice were euthanized and tumor inhibition rate TGI was calculated as follows:

$$TGI(\%)=[1-(T_i-T_0)/(V_i-V_0)]\times100$$

wherein,
$T_i$: mean tumor volume of the treatment group on day i of administration;
$T_0$: mean tumor volume of the treatment group on day 0 of administration;
$V_i$: mean tumor volume of the negative control group on day i of administration;
$V_0$: mean tumor volume of the negative control group on day 0 of administration.
5. Experimental results:
The experimental results are shown in FIG. 19A, FIG. 19B, Table 26 and Table 27.

TABLE 26

Evaluation of anti-tumor efficacy of test antibody-drug conjugate in PR9586 patient-derived xenograft model (calculations based on tumor volumes on day 25 after first administration)

| | | | Day 25 | | | |
|---|---|---|---|---|---|---|
| Group | Administration | Dose (mg/kg) | Tumor volume (mean ± SEM) | T/C (%) | TGI (%) | p value |
| 1 | Control group | — | 2524.01 ± 411.33 | — | — | — |
| 2 | WBP301088-X2 | 10 | 17.08 ± 6.02 | 0.68 | 99.32 | 0.00562 |

Note:
p values were calculated from tumor volumes (p > 0.05 indicates no statistical difference, and p < 0.01 indicates a significant difference).

TABLE 27

Evaluation of anti-tumor efficacy of test antibody-drug conjugate in PR9587 patient-derived xenograft model (calculations based on tumor volumes on day 48 after first administration)

| | | | Day 48 | | | |
|---|---|---|---|---|---|---|
| Group | Administration | Dose (mg/kg) | Tumor volume (mean ± SEM) | T/C (%) | TGI (%) | p value |
| 1 | Control group | — | 292.06 ± 31.00 | — | — | — |
| 2 | WBP301088-X2 | 10 | 90.29 ± 39.21 | 30.91 | 69.09 | 0.00261 |

Note:
p values were calculated from tumor volumes (p > 0.05 indicates no statistical difference, and p < 0.01 indicates a significant difference).

The results indicate that the antibody-drug conjugate WBP301088-X2 of the present application showed significant anti-tumor activity after the administration.

Example 9. Evaluation of Efficacy of Antibody-Drug Conjugate in Prostate Cancer Micro Patient-Derived Xenograft Model To investigate the efficacy of WBP301088-X2 (DAR6) in a prostate cancer patient-derived xenograft model, the anti-tumor effect of WBP301088-X2 (DAR6) was evaluated in a prostate cancer micro patient-derived xenograft mouse model.
1. Test compounds and materials
Blank control (control group): normal saline
WBP301088-X2 (treatment group): 10 mg/kg
Collagenase digest:

| Name | Supplier | Cat. No. |
|---|---|---|
| DNase | SIGMA | D5025-375KU |
| Hyaluronidase | SIGMA | H6254-500MG |
| Type II collagenase | GIBCO | 17101-015 |
| Type IV collagenase | GIBCO | 17104-019 |

The components in the table were mixed according to the manufacturer's instructions to prepare a collagenase digest.
2. Preparation method for test compounds: all samples were prepared by dilution with normal saline.
3. Experimental animals: CB17 SCID mice, male, aged 6-8 weeks, weighing about 18-22 g, purchased from Beijing Vital River Laboratory Animal Technology Co., Ltd.
4. Procedures:
Tumor tissues of patient-derived prostate cancer transplantation models LD1-2027-410644 and LD1-2034-362055 (obtained from Shanghai LIDE Biotech., Co. Ltd.) were inoculated subcutaneously into mice. When the tumors grew to 500-800 $mm^3$, the tumor tissues were surgically and aseptically removed from the mice, and non-tumor tissues and necrotic tissues were removed in a biosafety cabinet to ensure the purity of the inoculated tumor tissues. The mice were euthanized. The treated tumor tissues were cut into small tumor masses of 1-3 $mm^3$, and the tumor masses were digested with the collagenase digest at 37° C. for 1-2 h. The supernatant was removed by centrifugation at 1200 rpm for 3 min, and the cells were resuspended in 10 mL of PBS containing 1% FBS and counted on a hemocytometer. Murine cells were removed, and the supernatant was removed by centrifugation at 1200 rpm for 3 min. The cells were resuspended in an RPMI1640 cell culture medium and counted on a hemocytometer. The cell density was adjusted.

The cell suspension was placed into capsules. CB17 SCID mice were randomized into groups based on the weight, with 3 mice in each of the blank control group and the treatment group. Each mouse was inoculated subcutaneously with one capsule on each of the left and right sides, with a total of 6 capsules per group. Each of the capsules contained 5000 tumor cells. The day of inoculation was recorded as day 0, and the animals were subjected to a single administration by tail vein injection. The experiment was conducted for 10 days.

Figure 20A:
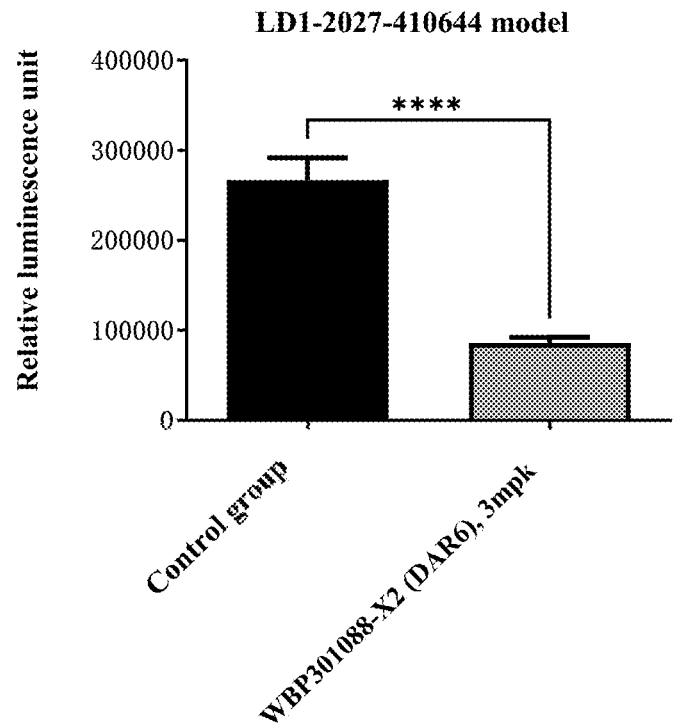
FIGS. 20A and 20B show evaluation of the efficacy of an antibody-drug conjugate in a prostate cancer micro patient-derived xenograft model.
Figure 20B:
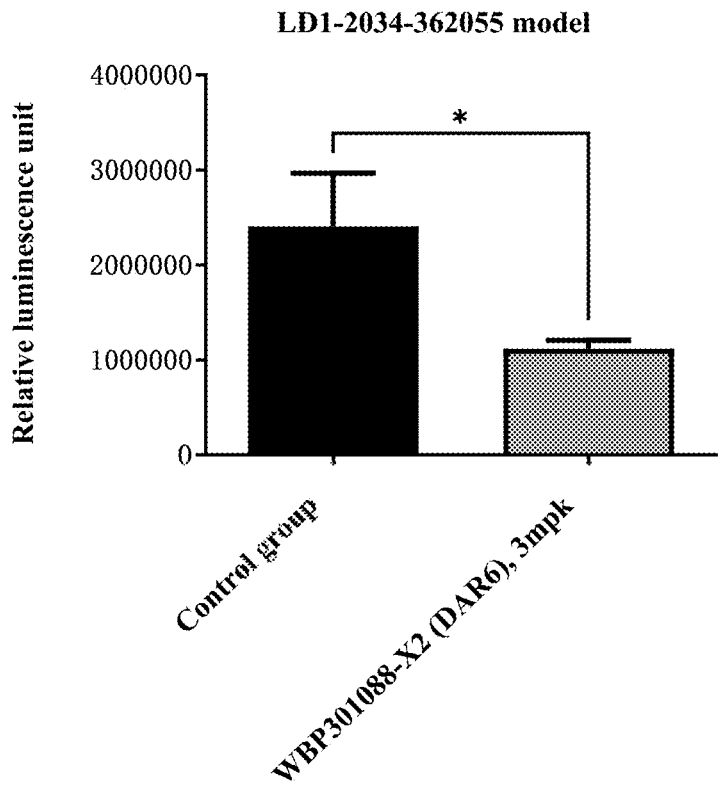

At the end of the experiment, the mice were euthanized. The capsules were removed and cell viability assay was performed with CellTiter-Glo, i.e., the capsules were cut into pieces, PBS and CellTiter-Glo™ reagent with the same volume were added, and the luminescence value was measured. In the optical signal and system, the luminescence value is in direct proportion to the amount of ATP, which is positively correlated with the number of living cells, so the cell viability can be informed by detecting the ATP content.
5. Experimental results:
The experimental results are shown in FIG. 20A, FIG. 20B and Table 28.

TABLE 28

Results of cell viability assay at the endpoint of the experiment

| | | LD1-2027-410644 model | | LD1-2034-362055 model | |
|---|---|---|---|---|---|
| Group | Test substance | Mean signal value | Standard error | Mean signal value | Standard error |
| 1 | Control group | 266766.78 | 24960.75 | 2403679.39 | 563363.25 |
| 2 | WBP301088-X2, 10 mg/kg | 85868.38 | 6086.40 | 1118020.86 | 90799.15 |

The results in FIG. 20A, FIG. 20B, Table 28 show that WBP301088-X2 had significant anti-tumor effect.

Example 10. Pharmacokinetic Study of Antibody-Drug Conjugate in Single Administration Objective After a single intravenous infusion of antibody-drug conjugate WBP301088-X2 (DAR6) in cynomolgus monkeys, the concentrations of WBP301088-X2 (DAR6), WBP301088-total antibody, and payload P-III-30 in serum were measured at different time points, and pharmacokinetic parameters of the WBP301088-X2 (DAR6), WBP301088-total antibody, and payload P-III-30 were calculated, providing a basis for preclinical and clinical studies.

Procedures 18 cynomolgus monkeys (half female and half male) were weighed one day before administration, stratified based on the weight, and then randomly divided into 3 groups (3 females and 3 males/group): a low dose group (1 mg/kg), a medium dose group (3 mg/kg), and a high dose group (10 mg/kg). Each animal was administered WBP301088-X2 solution by intravenous infusion.

Blood was collected from the forelimb veins of cynomolgus monkeys in each group, and treated samples of the blood collected at 0 h before and 0.5 h, 1 h, 4 h, 8 h, 24 h, 48 h, 72 h, 96 h, 168 h, 240 h, 336 h, 504 h, and 672 h after the administration were used as PK samples. After the blood collection at each time point was completed, serum was obtained by centrifugation for sample analysis.

The concentrations of WBP301088-total antibody and WBP301088-X2 in the serum samples of cynomolgus monkeys were quantitatively detected by ELISA method, and the concentration of P-III-30 in the serum samples of cynomolgus monkeys was quantitatively detected by LC-MS/MS method.

The experimental results are shown in Table 29.

indicating that the ADC was slowly released in monkeys, the conjugation mode was stable, the systemic exposure of P-III-30 was low, and WBP301088-X2 had high safety.

Example 11. Pharmacokinetic and Toxicity Studies of Antibody-Drug Conjugate in Multiple Administrations Objective Cynomolgus monkeys were intravenously administered WBP301088-X2 (DAR6) once every 3 weeks for a total of 2 administrations. The nature, the degree, and the dose-effect and time-effect relationships of possible toxic reactions caused by the antibody-drug conjugate were observed, and the target organ or tissue of toxicity was determined, providing reference for subsequent studies.

Procedures 6 cynomolgus monkeys (half female and half male) weighing 2.3-3.4 kg were divided into groups: a low dose group (30 mg/kg) and a high dose group (80 mg/kg). Each animal was administered in an administration volume of 5 mL/kg once every 3 weeks for a total of 2 administrations. The tolerance of animals and drug-related toxicity toxic manifestation were investigated in multiple aspects such as clinical observation, body weight and food intake, hematology, blood biochemistry, urine and gross anatomy.

Conclusion

Cynomolgus monkeys were intravenously administered WBP301088-X2 (DAR6) at 30 mg/kg and 80 mg/kg once every 3 weeks for a total of 2 administrations, and dissected 4 days after the 2nd administration (i.e., day 25 after the start of administration).

The results show that the antibody-drug conjugate was well tolerated by all animals during the test period, and no abnormalities were observed in body weight, food consumption, electrocardiographic parameters, coagulation parameters, and gross anatomy, indicating that the antibody-drug conjugate had good safety.

TABLE 29

Exposure parameters of single intravenous infusion of WBP301088-X2 (DAR6) at different doses in cynomolgus monkeys

| Test substance | PK parameters | Unit | Mean value of parameters | | |
|---|---|---|---|---|---|
| | | | Low dose group (1 mg/kg) | Medium dose group (3 mg/kg) | High dose group (10 mg/kg) |
| WBP301088-X2 | $C_{max}$ | µg/mL | 22.6 | 71.9 | 246 |
| | $AUC_{0-t}$ | h · µg/mL | 403 | 2070 | 11000 |
| | $AUC_{0-\infty}$ | h · µg/mL | 430 | 2110 | 11100 |
| WBP301088-total antibody | $C_{max}$ | µg/mL | 22.4 | 70.8 | 253 |
| | $AUC_{0-t}$ | h · µg/mL | 319 | 1760 | 10200 |
| | $AUC_{0-\infty}$ | h · µg/mL | 323 | 1770 | 10200 |
| P-III-30 | $C_{max}$ | ng/mL | NA | 0.133 | 0.573 |
| | $AUC_{0-t}$ | h · ng/mL | NA | 1.07 | 44.5 |

Conclusion

Under the conditions of this experiment, after a single intravenous administration of WBP301088-X2 at 1, 3 and 10 mg/kg in cynomolgus monkeys, there was no significant pharmacokinetic difference between the antibody-drug conjugate and the total antibody (antibody WBP301088), and all showed a dose-dependent increase, indicating that WBP301088-X2 had good stability in plasma in vivo. Also, P-III-30 was detected to have a low concentration in plasma, Although certain representative embodiments and details have been shown for the purpose of illustrating the present invention, it will be apparent to those skilled in this art that various variations and modifications can be made to these embodiments and details without departing from the scope of the subject matter of the present invention. In this respect, the scope of the present invention is limited only by the claims.

SEQUENCE LISTING

```
Sequence total quantity: 18
SEQ ID NO: 1                    moltype = AA   length = 11
FEATURE                         Location/Qualifiers
source                          1..11
                                mol_type = protein
                                organism = synthetic construct
SEQUENCE: 1
DYSITGDYAW N                                                                11

SEQ ID NO: 2                    moltype = AA   length = 16
FEATURE                         Location/Qualifiers
source                          1..16
                                mol_type = protein
                                organism = synthetic construct
SEQUENCE: 2
YISYSGSTSY NPSLQS                                                           16

SEQ ID NO: 3                    moltype = AA   length = 10
FEATURE                         Location/Qualifiers
source                          1..10
                                mol_type = protein
                                organism = synthetic construct
SEQUENCE: 3
SLGRRWYFVV                                                                  10

SEQ ID NO: 4                    moltype = AA   length = 17
FEATURE                         Location/Qualifiers
source                          1..17
                                mol_type = protein
                                organism = synthetic construct
SEQUENCE: 4
KSSQSLLQSS NQKNYLA                                                          17

SEQ ID NO: 5                    moltype = AA   length = 7
FEATURE                         Location/Qualifiers
source                          1..7
                                mol_type = protein
                                organism = synthetic construct
SEQUENCE: 5
FASTRES                                                                     7

SEQ ID NO: 6                    moltype = AA   length = 9
FEATURE                         Location/Qualifiers
source                          1..9
                                mol_type = protein
                                organism = synthetic construct
SEQUENCE: 6
QQHYSAPWT                                                                   9

SEQ ID NO: 7                    moltype = AA   length = 17
FEATURE                         Location/Qualifiers
source                          1..17
                                mol_type = protein
                                organism = synthetic construct
SEQUENCE: 7
KSSQSLLNSS NQKNYLA                                                          17

SEQ ID NO: 8                    moltype = AA   length = 119
FEATURE                         Location/Qualifiers
source                          1..119
                                mol_type = protein
                                organism = synthetic construct
SEQUENCE: 8
DVQLQESGPG LVKPSQSLSL TCTVTDYSIT GDYAWNWIRQ FPGNKLEWMG YISYSGSTSY           60
NPSLQSRISI TRDTSKNQFF LQLNSVTSED TATYFCARSL GRRWYFVVWG AGTTVTVSA            119

SEQ ID NO: 9                    moltype = AA   length = 113
FEATURE                         Location/Qualifiers
source                          1..113
                                mol_type = protein
                                organism = synthetic construct
SEQUENCE: 9
DIVMTQSPSS LAMSVGQKVT MSCKSSQSLL NSSNQKNYLA WYQQKPGQSP KLLIYFASTR           60
ESGVPDRFIG SGSGTDFTLT ISSVQAEDLT DYFCQQHYSA PWTFGGGTKL EIK                  113

SEQ ID NO: 10                   moltype = AA   length = 119
FEATURE                         Location/Qualifiers
source                          1..119
```

```
                            mol_type = protein
                            organism = synthetic construct
SEQUENCE: 10
QVQLQESGPG LVKPSQTLSL TCTVTDYSIT GDYAWNWIRQ HPGKGLEWIG YISYSGSTSY    60
NPSLQSRVTI SRDTSKNQFS LKLSSVTAAD TAVYFCARSL GRRWYFVVWG QGTTVTVSS    119

SEQ ID NO: 11           moltype = AA  length = 113
FEATURE                 Location/Qualifiers
source                  1..113
                        mol_type = protein
                        organism = synthetic construct
SEQUENCE: 11
DIVMTQSPDS LAVSLGERAT INCKSSQSLL QSSNQKNYLA WYQQKPGQPP KLLIYFASTR    60
ESGVPDRFSG SGSGTDFTLT ISSLQAEDVA VYYCQQHYSA PWTFGGGTKV EIK          113

SEQ ID NO: 12           moltype = AA  length = 449
FEATURE                 Location/Qualifiers
source                  1..449
                        mol_type = protein
                        organism = synthetic construct
SEQUENCE: 12
QVQLQESGPG LVKPSQTLSL TCTVTDYSIT GDYAWNWIRQ HPGKGLEWIG YISYSGSTSY    60
NPSLQSRVTI SRDTSKNQFS LKLSSVTAAD TAVYFCARSL GRRWYFVVWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 13           moltype = AA  length = 220
FEATURE                 Location/Qualifiers
source                  1..220
                        mol_type = protein
                        organism = synthetic construct
SEQUENCE: 13
DIVMTQSPDS LAVSLGERAT INCKSSQSLL QSSNQKNYLA WYQQKPGQPP KLLIYFASTR    60
ESGVPDRFSG SGSGTDFTLT ISSLQAEDVA VYYCQQHYSA PWTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                        220

SEQ ID NO: 14           moltype = AA  length = 448
FEATURE                 Location/Qualifiers
source                  1..448
                        mol_type = protein
                        organism = synthetic construct
SEQUENCE: 14
DVQLQESGPG LVKPSQSLSL TCTVTDYSIT GDYAWNWIRQ FPGNKLEWMG YISYSGSTSY    60
NPSLQSRISI TRDTSKNQFF LQLNSVTSED TATYFCARSL GRRWYFVVWG AGTTVTVSAA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 15           moltype = AA  length = 220
FEATURE                 Location/Qualifiers
source                  1..220
                        mol_type = protein
                        organism = synthetic construct
SEQUENCE: 15
DIVMTQSPSS LAMSVGQKVT MSCKSSQSLL NSSNQKNYLA WYQQKPGQSP KLLIYFASTR    60
ESGVPDRFIG SGSGTDFTLT ISSVQAEDLT DYFCQQHYSA PWTFGGGTKL EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                        220

SEQ ID NO: 16           moltype = AA  length = 119
FEATURE                 Location/Qualifiers
source                  1..119
                        mol_type = protein
                        organism = synthetic construct
SEQUENCE: 16
DVQLQESGPG LVKPSQSLSL TCTVTDYSIT GDYAWNWIRQ FPGNKLEWMG YISYSGSTSY    60
NPSLQSRISI TRDTSKNQFF LQLNSVTSED TATYFCARSL GRRWYFVVWG AGTTVTVSA   119

SEQ ID NO: 17           moltype = AA  length = 113
FEATURE                 Location/Qualifiers
source                  1..113
```

```
                        mol_type = protein
                        organism = synthetic construct
SEQUENCE: 17
DIVMTQSPSS LAMSVGQKVT MSCKSSQSLL NSSNQKNYLA WYQQKPGQSP KLLIYFASTR    60
ESGVPDRFIG SGSGTDFTLT ISSVQAEDLT DYFCQQHYSA PWTFGGGTKL EIK          113

SEQ ID NO: 18          moltype = AA  length = 17
FEATURE                Location/Qualifiers
source                 1..17
                        mol_type = protein
                        organism = synthetic construct
SEQUENCE: 18
KSSQSLLNPS NQKNYLA                                                   17
```

25. The antibody-drug conjugate according to claim 1, wherein the linker unit L is
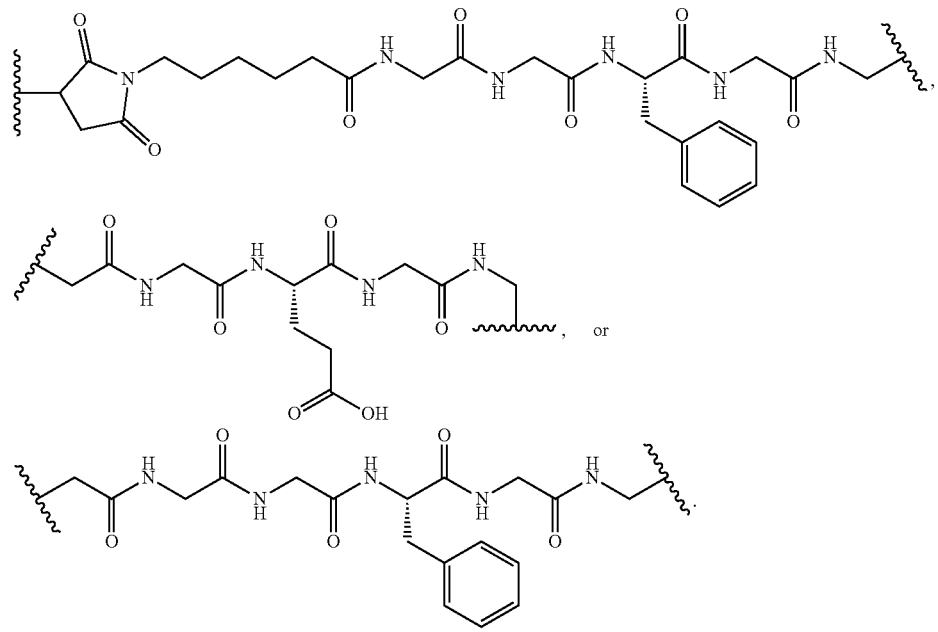

The invention claimed is:

1. An antibody-drug conjugate, comprising: a B7H3-targeting antibody or an antigen-binding fragment thereof, a linker unit and a cytotoxic drug, wherein the B7H3-targeting antibody or the antigen-binding fragment thereof comprises: HCDR1 comprising an amino acid sequence as set forth in SEQ ID NO: 1, HCDR2 comprising an amino acid sequence as set forth in SEQ ID NO: 2, HCDR3 comprising an amino acid sequence as set forth in SEQ ID NO: 3, LCDR1 comprising an amino acid sequence as set forth in SEQ ID NO: 4 or 7, LCDR2 comprising an amino acid sequence as set forth in SEQ ID NO: 5, and LCDR3 comprising an amino acid sequence as set forth in SEQ ID NO: 6; wherein the antibody drug conjugate is of formula (A-2);

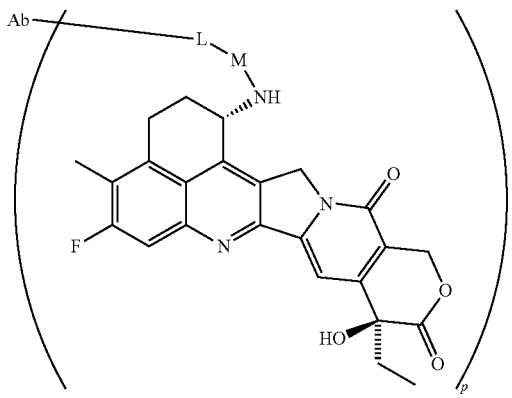

(A-2)

wherein
Ab is the B7H3-targeting antibody or antigen-binding fragment thereof;
p represents a connection number, and p is selected from the group consisting of integers from 1 to 10;
M is —$L^2$—$L^1$—C(O)—;
$L^2$ is —O— or —S—;
$L^1$ is —(C($R^{1a}$)($R^{1b}$))$_m$—CH$_2$—, C$_3$-C$_6$ saturated cycloalkyl, or 3- to 6-membered saturated heterocyclyl, wherein the C$_3$-C$_6$ saturated cycloalkyl and the 3- to 6-membered saturated heterocyclyl are each independently optionally substituted with one or more $R^{2a}$;
m is selected from the group consisting of 1, 2, 3, and 4;
the 3- to 6-membered saturated heterocyclyl comprises 1-3 heteroatoms selected from the group consisting of N, O, and S;
$R^{1a}$, $R^{1b}$ and $R^{2a}$ are each independently selected from the group consisting of hydrogen, halogen, hydroxy, amino, and C$_1$-C$_6$ alkyl, wherein the C$_1$-C$_6$ alkyl is optionally substituted with one or more R;
each R is independently hydrogen or halogen;
L is a linker unit —$L_a$—$L_b$—$L_c$—, wherein
—$L_a$— is

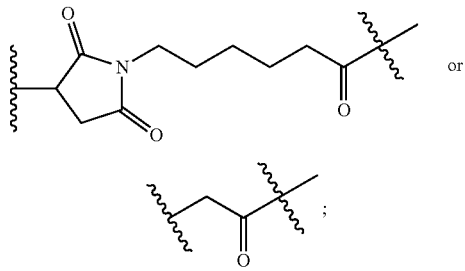

—$L_b$— is selected from the group consisting of:

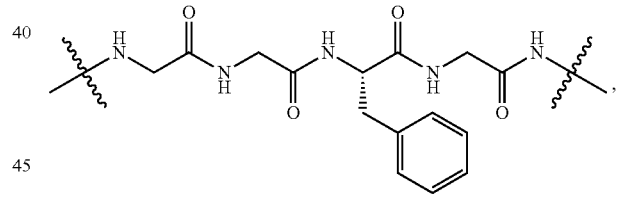

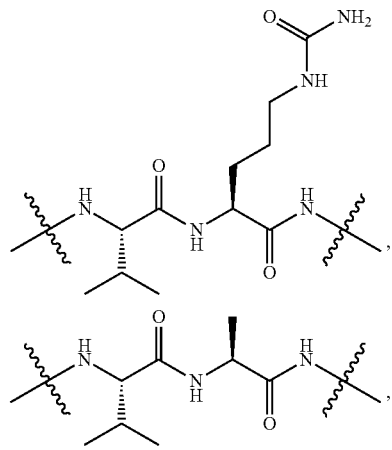

-continued

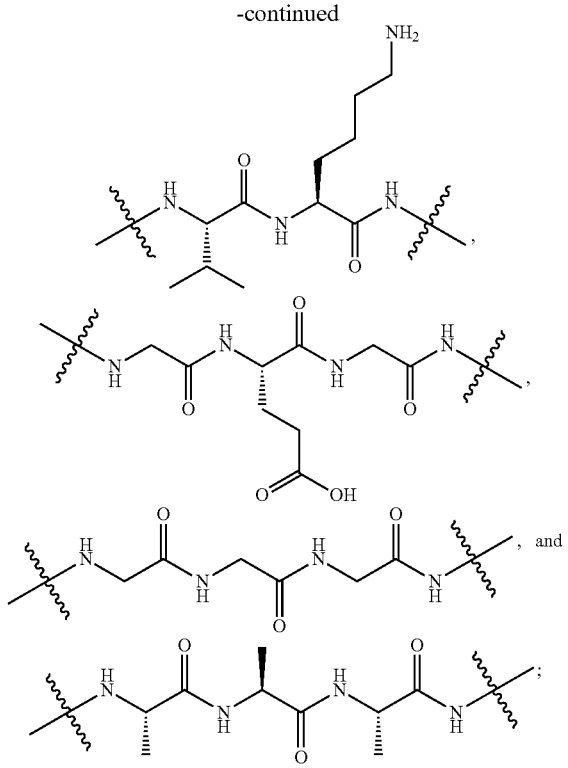

—L$_c$— is:

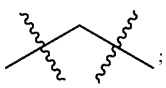

or a tautomer, an enantiomer, a diastereoisomer thereof, or a pharmaceutically acceptable salt or a solvate thereof.

2. The antibody-drug conjugate according to claim 1, wherein the antibody or the antigen-binding fragment thereof comprises:
(I) a heavy chain variable region comprising an amino acid sequence as set forth in SEQ ID NO: 8 and a light chain variable region comprising an amino acid sequence as set forth in SEQ ID NO: 9; or a heavy chain variable region comprising an amino acid sequence as set forth in SEQ ID NO: 10 and a light chain variable region comprising an amino acid sequence as set forth in SEQ ID NO: 11.

3. The antibody-drug conjugate according to claim 1, wherein the antibody is selected from the group consisting of: a human antibody, a humanized antibody, a chimeric antibody, a multispecific antibody, a monoclonal antibody, and a polyclonal antibody.

4. The antibody-drug conjugate according to claim 1, wherein the antigen-binding fragment is selected from the group consisting of: an Fab, an Fab', an F(ab')$_2$, an Fv, an ScFv, an Fab'-SH, a bispecific antibody, and a linear antibody.

5. The antibody-drug conjugate according to claim 1, wherein the antibody comprises an immunoglobulin constant region, the immunoglobulin constant region being a human IgG constant region.

6. The antibody-drug conjugate according to claim 1, wherein the antibody or the antigen-binding fragment thereof comprises:
(I) a heavy chain comprising an amino acid sequence as set forth in SEQ ID NO: 12 and a light chain comprising an amino acid sequence as set forth in SEQ ID NO: 13; or a heavy chain comprising an amino acid sequence as set forth in SEQ ID NO: 14 and a light chain comprising an amino acid sequence as set forth in SEQ ID NO: 15.

7. An antibody-drug conjugate having a formula:

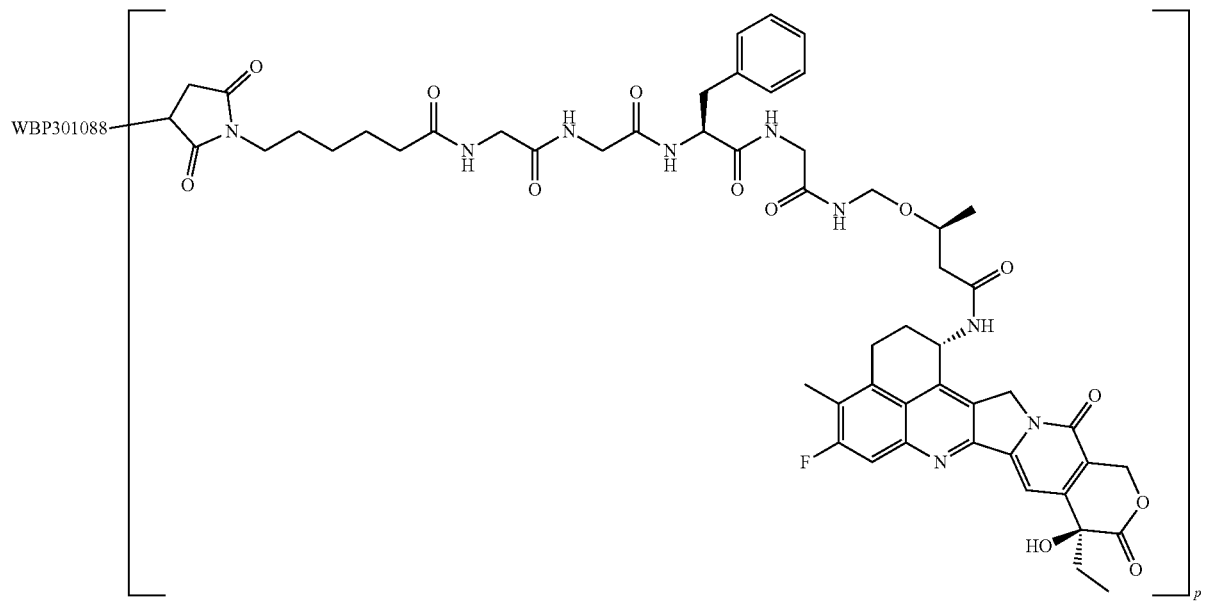

or a pharmaceutically acceptable salt thereof,
wherein:
WBP301088 is an anti-B7H3 antibody comprising a heavy chain amino acid sequence as set forth in SEQ ID NO: 12 and a light chain amino acid sequence as set forth in SEQ ID NO: 13; and
p represents a connection number, and p is 2 to 8.

8. The antibody-drug conjugate of claim 7, wherein p is 4 to 8, or a pharmaceutically acceptable salt thereof.

9. The antibody-drug conjugate of claim 7, wherein p is 5 to 7, or a pharmaceutically acceptable salt thereof.

10. The antibody-drug conjugate of claim 7, wherein p is 6, or a pharmaceutically acceptable salt thereof.

11. A method for producing the antibody-drug conjugate of claim 7, comprising reacting:
an anti-B7H3 antibody WBP301088 comprising a heavy chain amino acid sequence as set forth in SEQ ID NO: 12 and a light chain amino acid sequence as set forth in SEQ ID NO: 13;
with a compound of formula X2:

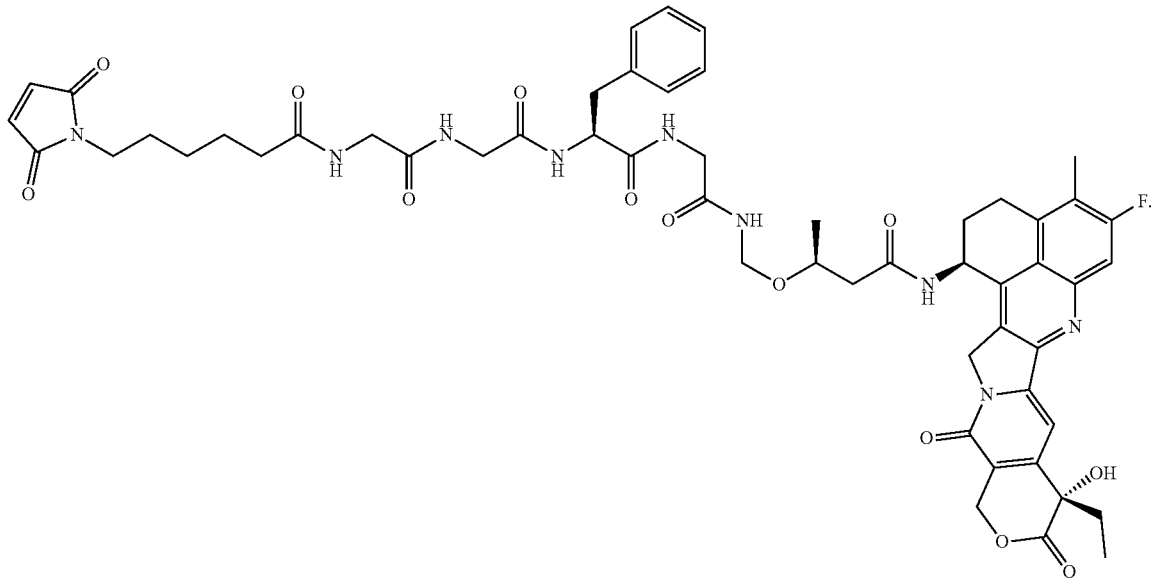

12. A pharmaceutical composition, comprising the antibody-drug conjugate according to claim 1, or a pharmaceutically acceptable salt thereof, and a pharmaceutically acceptable carrier or excipient.

13. A method for treating cancer, comprising administering to a subject in need the antibody-drug conjugate according to claim 1, or pharmaceutically acceptable salt thereof.

14. The method of claim 13, wherein the cancer is selected from the group consisting of breast cancer, neurological tumors, melanoma, lung cancer, head and neck cancer, colorectal cancer, pancreatic cancer, gastric cancer, renal cancer, bladder cancer, prostate cancer, ovarian cancer, cervical cancer, glioblastoma, esophageal cancer, renal cell carcinoma, endometrial cancer, skin cancer, testicular cancer, thyroid cancer, urothelial cancer, lymphoma (such as non-Hodgkin lymphoma), chronic lymphocytic leukemia, diffuse large B-cell lymphoma, and multiple myeloma.

15. The method of claim 13, wherein the cancer is selected from the group consisting of breast cancer, neurological tumors, melanoma, lung cancer, colorectal cancer, and prostate cancer.

16. The method of claim 14, wherein the cancer is lung cancer.

17. A method for treating cancer, comprising administering to a subject in need the pharmaceutical composition according to claim 12.

18. The method of claim 17, wherein the cancer is selected from the group consisting of breast cancer, neurological tumors, melanoma, lung cancer, head and neck cancer, colorectal cancer, pancreatic cancer, gastric cancer, renal cancer, bladder cancer, prostate cancer, ovarian cancer, cervical cancer, glioblastoma, esophageal cancer, renal cell carcinoma, endometrial cancer, skin cancer, testicular cancer, thyroid cancer, urothelial cancer, lymphoma (such as non-Hodgkin lymphoma), chronic lymphocytic leukemia, diffuse large B-cell lymphoma, and multiple myeloma.

19. The method of claim 17, wherein the cancer is selected from the group consisting of breast cancer, neurological tumors, melanoma, lung cancer, colorectal cancer, and prostate cancer.

20. The method of claim 17, wherein the cancer is lung cancer.

21. A method for treating cancer, comprising administering to a subject in need an antibody-drug conjugate including an anti-B7H3 antibody comprising a heavy chain amino acid sequence as set forth in SEQ ID NO: 12 and a light chain amino acid sequence as set forth in SEQ ID NO: 13.

22. The antibody-drug conjugate of claim 7, wherein p is 4, or a pharmaceutically acceptable salt thereof.

23. The antibody-drug conjugate of claim 7, wherein p is 8, or a pharmaceutically acceptable salt thereof.

24. The antibody-drug conjugate according to claim 1, wherein $L^1$ is —$(C(R^{1a})(R^{1b}))_m$—$CH_2$—, wherein m is 1 or 2.